(12) United States Patent
Jugde et al.

(10) Patent No.: US 8,859,848 B2
(45) Date of Patent: Oct. 14, 2014

(54) PHLORETIN GLYCOSYLTRANSFERASES, POLYNUCLEOTIDES ENCODING THESE AND METHODS OF USE

(75) Inventors: Helene Jugde, Allonnes (FR); Ross Atkinson, Auckland (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 735 days.

(21) Appl. No.: 12/818,725

(22) Filed: Jun. 18, 2010

(65) Prior Publication Data

US 2011/0030098 A1 Feb. 3, 2011

Related U.S. Application Data

(63) Continuation of application No. PCT/NZ2008/000341, filed on Dec. 19, 2008.

(30) Foreign Application Priority Data

Dec. 21, 2007 (NZ) .......................... 564691

(51) Int. Cl.

| | | |
|---|---|---|
| C12N 15/82 | (2006.01) | |
| C12N 15/87 | (2006.01) | |
| A01H 1/00 | (2006.01) | |
| A01H 9/00 | (2006.01) | |
| A01H 11/00 | (2006.01) | |
| C12N 15/00 | (2006.01) | |
| C12N 5/04 | (2006.01) | |
| C12N 5/10 | (2006.01) | |
| C12N 15/74 | (2006.01) | |
| C12N 9/10 | (2006.01) | |

(52) U.S. Cl.
CPC ............ *C12N 15/825* (2013.01); *C12N 9/1048* (2013.01); *C12N 15/8243* (2013.01)
USPC ........ 800/278; 800/284; 800/295; 435/320.1; 435/419; 435/468; 435/471

(58) Field of Classification Search
USPC ....................................................... 800/278
See application file for complete search history.

(56) References Cited

U.S. PATENT DOCUMENTS

| | | | |
|---|---|---|---|
| 4,795,855 A | 1/1989 | Fillatti et al. | |
| 5,004,863 A | 4/1991 | Umbeck | |
| 5,159,135 A | 10/1992 | Umbeck | |
| 5,177,010 A | 1/1993 | Goldman et al. | |
| 5,187,073 A | 2/1993 | Goldman et al. | |
| 5,188,958 A | 2/1993 | Moloney et al. | |
| 5,416,011 A | 5/1995 | Hinchee et al. | |
| 5,463,174 A | 10/1995 | Moloney et al. | |
| 5,563,455 A | 10/1996 | Cheng | |
| 5,569,834 A | 10/1996 | Hinchee et al. | |
| 5,591,616 A | 1/1997 | Hiei et al. | |
| 5,750,871 A | 5/1998 | Moloney et al. | |
| 5,792,935 A | 8/1998 | Arntzen et al. | |
| 5,824,877 A | 10/1998 | Hinchee et al. | |
| 5,846,797 A | 12/1998 | Strickland | |
| 5,952,543 A | 9/1999 | Firoozabady et al. | |
| 5,968,830 A | 10/1999 | Dan et al. | |
| 5,981,840 A | 11/1999 | Zhao et al. | |
| 6,020,539 A | 2/2000 | Goldman et al. | |
| 6,037,522 A | 3/2000 | Dong et al. | |
| 6,074,877 A | 6/2000 | D'Halluin et al. | |
| 7,041,322 B2 * | 5/2006 | Gaudout et al. ............. | 424/765 |
| 7,214,786 B2 | 5/2007 | Kovalic et al. | |
| 2003/0233670 A1 * | 12/2003 | Edgerton et al. ............ | 800/278 |
| 2004/0031072 A1 | 2/2004 | La Rosa et al. | |
| 2004/0034888 A1 | 2/2004 | Liu et al. | |
| 2004/0123343 A1 | 6/2004 | La Rosa et al. | |
| 2004/0172684 A1 | 9/2004 | Kovalic et al. | |
| 2004/0214272 A1 | 10/2004 | La Rosa et al. | |
| 2004/0216190 A1 | 10/2004 | Kovalic et al. | |
| 2005/0208643 A1 * | 9/2005 | Schmidt-Dannert et al. ................... | 435/252.31 |
| 2006/0048240 A1 | 3/2006 | Alexandrov et al. | |
| 2006/0123505 A1 | 6/2006 | Kikuchi et al. | |
| 2006/0150283 A1 | 7/2006 | Alexandrov et al. | |
| 2006/0236419 A1 | 10/2006 | La Rosa et al. | |
| 2007/0033674 A1 * | 2/2007 | Brugliera et al. ............ | 800/282 |
| 2007/0214517 A1 | 9/2007 | Alexandrov et al. | |
| 2010/0077503 A1 | 3/2010 | Laing et al. | |
| 2010/0306875 A1 | 12/2010 | Rikkerink et al. | |

FOREIGN PATENT DOCUMENTS

| | | |
|---|---|---|
| WO | 03/057877 | 7/2003 |
| WO | 2008/108668 | 9/2008 |
| WO | 2009/058030 | 5/2009 |

OTHER PUBLICATIONS

A. Tuskan et al., The Genome of Black Cottonwood, Populus trichocarpa 313 Science 1596-1604 (2006).*

Genbank Accession No. BAG31947.1 [online]. [retrieved on Aug. 9, 2012]. Retrieved from the Internet: <http://www.ncbi.nlm.nih.gov/protein/BAG31947.1>.*

Koes et al., The chalcone synthase multigene family of Petunia hybrid (V30): differential, light-reulgated expression during flower development and UV light induction, 12 Plant Molecular Biology, 213-225 (1989).*

(Continued)

*Primary Examiner* — Cynthia Collins
*Assistant Examiner* — Rebecca Coobs
(74) *Attorney, Agent, or Firm* — Lathrop & Gage LLP

(57) ABSTRACT

The invention provides method for producing a plant cell or plant with increased phlorizin or phloretin glycosyltransferase activity, the method comprising transformation of a plant cell or plant with a polynucleotide encoding a polypeptide with phloretin glycosyltransferase activity. The invention also provides host cells, plant cells and plants, genetically modified to contain and or express the polynucleotides.

32 Claims, 11 Drawing Sheets

(56) References Cited

OTHER PUBLICATIONS

Li et al., Analysis of the UDP-glycosyltransferase Multigene Family of *Arabidopsis thaliana*, 276 Journal of Biological Chemistry No. 6, 4338-4343 (2001).*
Valasco et al., The genome of the domesticated apple (*Malus* x *domestica* Borkh.), 42 Nature Genetics No. 10, 833-839 (2010)).*
Guo et al., Protein tolerance to random amino acid change, 101 PNAS No. 25, 9205-9210 (2004).*
Lindlöf (Gene identification through large-scale EST sequence processing, 2 Applied Bioinformatics No. 3, 123-129 (2003)).*
Roemmelt et al., Formation of novel flavonoids in apple (*Malus* x *domestica*) treated with the 2-oxoglutarate-dependent dioxygenase inhibitor prohexadione-Ca, 64 Phytochemistry, 700-716 (2003).*
Lewinsohn et al., Flavanone Glycoside Biosynthesis in Citrus, 91 Plant Physiology, 1323-1328 (1989).*
Gosch et al., Phloridzin: Biosynthesis, distribution and physiological relevance in plants, 71 Phytochemistry, 838-843 (2010).*
van der Krol et al. (FlavonoidGenes in Petunia: Addition of a Limited Number of Gene Copies May Lead to a Suppression of Gene Expression, 2 Plant Cell, 291-299 (1990)).*
Werner et al. (Expression of a Dianthus flavonoid glucosyltransferase in *Saccharomyces cerevisiae* for whole-cell bioctalysis, 142 Journal of Biotechnology, 233-241 (2009)).*
Ogata et al. (Cloning and heterologous expression of cDNAs encoding flavonoid glucosyltransferases from *Dianthus caryophyllus*, 21 Plant Biotechnology No. 5, 367-375 (2004)).*
International Preliminary Report on Patentability, corresponding to International Application No. PCT/NZ2008/000341 (filed Dec. 19, 2008), parent of the present application, dated Dec. 10, 2009, 12 pp.
Search Report corresponding to International Application No. PCT/NZ2008/000341 (filed Dec. 19, 2008), parent of the present application, dated Sep. 7, 2009, 4 pp.
Written Opinion corresponding to International Application No. PCT/NZ2008/000341 (filed Dec. 19, 2008), parent of the present application, dated Sep. 7, 2009, 8 pp.
NCBI Database Accession No. NM_128529.2 (Apr. 20, 2007) "*Arabidopsis thaliana* UGT71C1 (UDP-Glucosyl Transferase 71C1); UDP-glycosyltransferase/ quercetin 3'-O-glucosyltransferase/ quercetin 7-O-glucosyltr> (UGT71O1) mRNA, complete cds".
NCBI Database Accession No. NP_192016.1 (Aug. 21, 2009) "GT72B1; UDP-glucosyltransferase/ UDP-glycosyltransferase/ transferase, transferring glycosyl groups [*Arabidopsis thaliana*]".
NCBI Database Accession No. NP_195395 (Aug. 21, 2009) "UDP-glycosyltransferase/ transferase, transferring glycosyl groups [*Arabidopsis thaliana*]".
NCBI Database Accession No. NM_179647.2 (Apr. 19, 2010) "*Arabidopsis thaliana* UDP-glucoronosyl/UDP-glucosyl transferase family protein (AT2G18570) mRNA, complete cds".
NCBI Database Accession No. NP_188812.1 (Apr. 19, 2010) "UGT71B1 (UDP-Glucosyl Transferase 71B1); UDPglycosyltransferase/ quercetin 3-O-glucosyltransferase/ transferase, transferring glycosyl groups [*Arabidopsis thaliana*]".
Achnine et al. (Mar. 7, 2005) NCBI Database Accession No. AY747627, "*Medicago truncatula* triterpene UDP-glucosyl transferase UGT71G1 mRNA, complete cds".
Afunian, M.R. (Jan. 5, 2004) NCBI Database Accession No. AJ581791, "*Pyrus communis* partial gene for putative nucleotide binding site leucine-rich repeat disease resistance protein, clone RGA04".
Gleave, A. (Apr. 2006) GenBank Database Accession No. EB128371.1, "010914AVBC014011PG (AVBC) Royal Gala young shoot *Malus x domestica* cDNA clone AVBC014011, mRNA sequence".
Gleave, A. (Apr. 2006) GenBank Database Accession No. EB153724.1, "021119ABMA001719HT (ABMA) M9 phloem *Malus x domestica* cDNA clone ABMA001719, mRNA sequence".

Gleave, A. (Apr. 2006) GenBank Database Accession No. EB134664.1, "010512AAXA001232HT (AAXA) Royal Gala 126 DAFB fruit core *Malus x domestica* cDNA clone AAXA001232, mRNA sequence".
Iida et al. (Apr. 21, 2009), NCBI Database Accession No. BAH19474, "AT3G16520 [*Arabidopsis thaliana*]".
Jugde et al. (Jul. 31, 2008) NCBI Database Accession No. ABY73540, "*Malus pumila* glycosyltransferase UGT88A1 mRNA, complete cds".
Jugde et al. (Jul. 31, 2008) GenBank Database Accession No. EU246349.1, "*Malus pumila* glycosyltransferase UGT88A1 mRNA, complete cds".
Mato et al. (Feb. 5, 1999) NCBI Database Accession No. BAA36412, "UDP-glycose:flavonoid glycosyltransferase [*Vigna mungo*]".
Richman et al. (Dec. 28, 2004) NCBI Database Accession No. AAR06919, "UDP-glycosyltransferase 88B1 [*Stevia rebaudiana*]".
Rikkerink et al. (Jun. 19, 2006), NCBI Database Accession No. DQ644205, "*Malus x domestica* clone ABFA005053CT putative NBS-LRR disease resistance protein gene, partial cds".
Sasaki et al. (Feb. 16, 2008) NCBI Database Accession No. BAC10743, "glucosyltransferase-like [*Oryza sativa* Japonica Group]".
Shinn et al. (May 6, 2003) NCBI Database Accession No. BT006599, "*Arabidopsis thaliana* At2g29730 mRNA, complete cds".
Shinn et al. (Oct. 2, 2004) NCBI Database Accession No. AAU90060, "At3g50740 [*Arabidopsis thaliana*]".
Taguchi et al. (Mar. 19, 2009) NCBI Database Accession No. AB052557, "*Nicotiana tabacum* NTGT1a mRNA for glucosyltransferase, complete cds".
Taguchi et al. (Mar. 19, 2009) NCBI Database Accession No. AB072918, "*Nicotiana tabacum* NtGT3 mRNA for glucosyltransferase, complete cds".
Velasco, et al. (Jan. 19, 2007) GenBank Database Accession No. AM443784.1, "*Vitis vinifera*, whole genome shotgun sequence, contig VV78X106239.29, clone ENTAV 115".
Abbott et al. (2002) "Simultaneous Suppression of Multiple Genes by Single Transgenes. Down-Regulation of Three Unrelated Lignin Biosynthetic Genes in Tobacco," Plant Physiol. 128(3):844-853.
Achnine et al. (2005) "Genomics-based selection and functional characterization of triterpene glycosyltransferases from the model legume *Medicago truncatula*," Plant Journal 41:875-887.
Alam et al. (1999) "Transgenic insect-resistant maintainer line (IR68899B) for improvement of hybrid rice," Plant Cell Reports 18:572-575.
Altschul et al. (1997) "Gapped BLAST and PSI-BLAST: A New Generation of Protein Database Search Programs," Nucleic Acids Res. 25(17):3389-3402.
Awad et al. (2000) "Flavonoid and chlorogenic acid levels in apple fruit: characterisation of variation," Scientia Horticulturae 83:249-263.
Bairoch and Bucher (1994) "PROSITE: Recent Developments," Nucleic Acids Res. 22(17):3583-3589.
Barth et al. (2005) "Cloudy apple juice decreases DNA damage, hyperproliferation and aberrant crypt foci development in the distal colon of DMH-initiated rats," Carcinogenesis 26(8):1414-1421.
Baxevanis, A.D. (2001) "The Molecular Biology Database Collection: an updated compilation of biological database resources," Nucleic Acids Research 29(1):1-10.
Boccia et al. (1999) "Phlorizin, a Competitive Inhibitor of Glucose Transport, Facilitates Memory Storage in Mice," Neurobiology of Learning and Memory 71:104-112.
Cox et al. (2005) "Antioxidant activity in Australian native sarsaparilla (*Smilax glyciphylla*,"Journal of Ethnopharmacology 101:162-168.
Dan et al. (2006) "MicroTom—a high-throughput model transformation system for functional genomics," Plant Cell Reports 25:432-441, online publication Dec. 9, 2005.
De Carvalho Niebel et al. (1995) "Post Transcriptional Cosuppression of β-1,3-Glucanase Genes Does Not Affect Accumulation of Transgene Nuclear mRNA," Plant Cell 7:347-358.
Dong et al. (Mar. 20, 2007) "Preparative Separation and Identification of the Flavonoid Phlorhizin from the Crude Extract of *Lithocarpus Polystachyus* Rehd," Molecules 12:552-562.

(56) References Cited

OTHER PUBLICATIONS

Dragovic-Uzelac et al. (2005) "The study of phenolic profiles of raw apricots and apples and their purees by HPLC for the evaluation of apricot nectars and jams authenticity," Food Chemistry 91:373-383.
Ehrenkranz et al. (2005) "Phlorizin: a review," Diabetes/Metabolism Research and Reviews 21:31-38.
Falquet et al. (2002) "The PROSITE Database, Its Status in 2002," Nucleic Acids Res. 30(1):235-238.
Feng and Doolittle (1987) "Progressive Sequence Alignment as a Prerequisite to Correct Phylogenetic Trees," J. Mol. Evol. 25:351-360.
Folta et al. (Apr. 14, 2006) "Characterization of LF9, an octoploid strawberry genotype selected for rapid regeneration and transformation," Planta 224:1058-1067.
Fukuchi-Mizutani et al. (2003) "Biochemical and Molecular Characterization of a Novel UDP-Glucose:Anthocyanin 3'-O-Glucosyltransferase, a Key Enzyme for Blue Anthocyanin Biosynthesis, from Gentian," Plant Physiology 132:1652-1663.
Gardiner et al. (2003) "Candidate Resistance Genes from an EST Database Prove a Rich Source of Markers for Major Genes Conferring Resistance to Important Apple Pests and Diseases," Acta Horticulturae 622:141-151.
Gessler et al. (Nov. 2006) "*Venturia inaequalis* Resistance in Apple," Critical Reviews in Plant Sciences 25:473-503.
Gonzalez Padilla et al. (2003) "Early antibiotic selection and efficient rooting and acclimatization improve the production of transgenic plum plants (*Prunus domestica* L.)," Plant Cell Rep. 22(1):38-45.
Graham et al. (1995) "*Agrobacterium*-Mediated Transformation of Soft Fruit *Rubus, Ribes*, and *Fragaria*," Methods Mol Biol. 44:129-33.
Hall, T.A. (1999) "BioEdit: a user-friendly biological sequence alignment editor and analysis program for Windows 95/98/NT," Nucleic Acids Symposium Series 41:95-98.
Hansen et al. (2003) "The in vitro substrate regiospecificity of recombinant UGT85B1, the cyanohydrin glucosyltransferase from *Sorghum bicolor*," Phytochemistry 64:143-151.
Hefner et al. (2003) "Probing suggested catalytic domains of glycosyltransferases by site-directed mutagenesis," Eur. J. of Biochem. 270:533-538.
Hellens et al. (2005) "Transient expression vectors for functional genomics, quantification of promoter activity and RNA silencing in plants," *Plant Methods* 1:13, pp. 1-14.
Hilt et al. (2003) "Detection of Phloridzin in Strawberries (*Fragaria* x *ananassa* Duch.) by HPLC-PDA-MS/MS and NMR Spectroscopy," Journal of Agricultural and Food Chemistry 51:2896-2899.
Hofmann et al. (1999) "The PROSITE Database, Its Status in 1999," Nucleic Acids Res. 27(1):215-219.
Horsch et al. (1985) "A Simple and General Method for Transferring Genes into Plants," Science 227:1229-1231 with correction of authorship.
Hunter and Hull (Apr. 30, 1993) "Variation in Concentrations of Phloridzin and Phloretin in Apple Foliage," Phytochemistry 34(5):1251-1254.
Jackson et al. (2001) "Identification and Biochemical Characterization of an *Arabidopsis* Indole-3-acetic Acid Glucosyltransferase," Journal of Biological Chemistry 276(6):4350-4356.
Jobling et al. (2003) "Immunomodulation of enzyme function in plants by single-domain antibody fragments," Nature Biotechnology 21(1):77-80.
Jones et al. (1998) "The effect of chimeric transgene architecture on co-ordinated gene silencing," Planta 204:499-505.
Jones et al. (2003) "UGT73C6 and UGT78D1, Glycosyltransferases Involved in Flavonol Glycoside Biosynthesis in *Arabidopsis thaliana*," Journal of Biological Chemistry 278:43910-43918.
Jouvenot et al. (2003) "Targeted Regulation of Imprinted Genes by Synthetic Zinc-Finger Transcription Factors," Gene Therapy 10:513-522.
Jugde et al. (Aug. 2008) "Isolation and characterization of a novel glycosyltransferase that converts phloretin to phlorizin, a potent antioxidant in apple," FEBS Journal 275:3804-3814; first published online Jun. 28, 2008.
Krens et al. (1997) "Transgenic caraway, *Carum carvi* L.: a model species for metabolic engineering," Plant Cell Reports 17:39-43.
Kumar et al. (1996) "Potato plants expressing antisense and sense S-adenosylmethionine decarboxylase (SAMDC) transgenes show altered levels of polyamines and ethylene: antisense plants display abnormal phenotypes," The Plant J. 9(2):147-158.
Li et al. (1996) "Genetic transformation of cassava (*Manihot esculenta* Crantz)," Nature Biotechnology 14:736-740.
Li et al. (2001) "Phylogenetic Analysis of the UDP-glycosyltransferase Multigene Family of *Arabidopsis thaliana*," Journal of Biological Chemistry 276(6):4338-4343.
Li et al. (2001) "A fast neutron deletion mutagenesis-based reverse genetics system for plants," The Plant Journal 27(3):235-242.
Li et al. (2003) "Transgenic rose lines harboring an antimicrobial protein gene, *Ace-AMP1*, demonstrate enhanced resistance to powdery mildew (*Sphaerotheca pannosa*)," Planta 218(2):226-232.
Lim et al. (2002) "The Activity of *Arabidopsis* Glycosyltransferases Toward Salicylic Acid, 4-Hydroxybenzoic Acid, and Other Benzoates," Journal of Biological Chemistry 277(1):586-592.
Lim et al. (2003) "Regioselectivity of glucosylation of caffeic acid by a UDP-glucose:glucosyltransferase is maintained in planta," Biochem. J. 373:987-992.
Lim et al. (2004) "*Arabidopsis* glycosyltransferases as Biocatalysts in Fermentation for Regioselective Synthesis of Diverse Quercetin Glucosides," Biotechnology and Bioengineering 87(5):623-631.
Lim et al. (2004) "A class of plant glycosyltransferases involved in cellular homeostasis," EMBO Journal 23:2915-2922.
Lim et al. (2005) "Identification and characterisation of *Arabidopsis* glycosyltransferases capable of glucosylating coniferyl aldehyde and sinapyl aldehyde," FEBS Letters 579:2802-2806.
Llave et al. (2002) "Cleavage of *Scarecrow-like* mRNA Targets Directed by a Class of *Arabidopsis* miRNA," Science 297:2053-2056.
Lommen et al. (2000) "Application of Directly Coupled HPLC-NMR-MS to the Identification and Confirmation of Quercetin Glycosides and Phloretin Glycosides in Apple Peel," Anal. Chem. 72:1793-1797.
Loutre et al. (2003) "Isolation of a glucosyltransferase from *Arabidopsis thaliana* active in the metabolism of the persistent pollutant 3,4-dichloroaniline," The Plant Journal 34:485-493.
Mato et al. (1998) "Isolation and Characterization of a cDNA Clone of UDP-Galactose: Flavonoid 3-*O*-Galactosyltransferase (UF3GaT) Expressed in *Vigna mungo* Seedlings," Plant Cell Physiol. 39(11):1145-1155.
Matsuda et al. (2005) "Development of an *Agrobacterium*-mediated transformation method for pear (*Pyrus communis* L.) with leaf-section and axillary shoot-meristem explants," Plant Cell Rep. 24(1):45-51.
McIntyre et al. (1996) "Strategies for the suppression of peroxidase gene expression in tobacco. I. Designing efficient ribozymes," Transgenic Research 5:257-262.
Messner et al. (2003) "*Arabidopsis* glucosyltransferases with activities toward both endogenous and xenobiotic substrates," Planta 217:138-146.
Michelmore et al. (Sep. 3, 1987) "Transformation of lettuce (*Lactuca sativa*) mediated by *Agrobacterium tumefaciens*," Plant Cell Rep. 6:439-442.
Napoli et al. (1990) "Introduction of a Chimeric Chalcone Synthase Gene into Petunia Results in Reversible Co-Suppression of Homologous in trans," The Plant Cell 2:279-289.
Newcomb et al. (May 2006) "Analyses of Expressed Sequence Tags from Apple," Plant Physiology 141:147-166.
Nieuwenhuizen et al. (Aug. 7, 2007) "Identification and characterisation of acidic and novel basic forms of actinidin, the highly abundant cysteine protease from kiwifruit," Functional Plant Biology 34:946-961.
Niu et al. (1998) "Transgenic peppermint (*Mentha* x *piperita* L.) plants obtained by cocultivation with *Agrobacterium tumefaciens*," Plant Cell Reports 17:165-171.

(56) References Cited

OTHER PUBLICATIONS

Notredame et al. (2000) "T-Coffee: A Novel Method for Fast and Accurate Multiple Sequence Alignment," J. Mol. Biol. 302:205-217.

Oosumi et al. (2006) "High-efficiency transformation of the diploid strawberry (*Fragaria vesca*) for functional genomics," Planta 223(6):1219-1230; published online Dec. 5, 2005.

Ortiz et al. (1996) "Hygromycin resistance as an efficient selectable marker for wheat stable transformation," Plant Cell Reports 15:877-881.

Pena et al. (1995) "High efficiency *Agrobacterium*-mediated transformation and regeneration of citrus," Plant Science 104:183-191.

Puel et al. (2005) "Prevention of Bone Loss by Phloridzin, an Apple Polyphenol, in Ovariectomized Rats under Inflammation Conditions," Calcif Tissue Int 77:311-318.

Ramesh et al. (Mar. 14, 2006) "Improved methods in *Agrobacterium*-mediated transformation of almond using positive (mannose/*pmi*) or negative (kanamycin resistance) selection-based protocols," Plant Cell Rep. 25(8):821-828.

Rezk et al. (2002) "The antioxidant activity of phloretin: the disclosure of a new antioxidant pharmacophore in flavonoids," Biochemical and Biophysical Research Communications 295:9-13.

Richman et al. (2005) "Functional genomics uncovers three glucosyltransferases involved in the synthesis of the major sweet glucosides of *Stevia rebaudiana*," The Plant Journal 41:56-67.

Ridgway et al. (1996) "Potent antioxidant properties of novel apple-derived flavonoids with commercial potential as food additives," Biochemical Society Transactions 24:391S.

Ridgway et al. (1997) "Antioxidant action of novel derivatives of the apple-derived flavonoid phloridzin compared to oestrogen: relevance to potential cardioprotective action," Biochemical Society Transactions 25:106S.

Ridgway et al. (1997) "Phloridzin derivatives; food additives/chemopreventative drugs of the future," Biochemical Society Transactions 25:109S, 109S.

Ross et al. (2001) "Higher plant glycosyltransferases," Genome Biology 2(2):3004.1-3004.6.

Song et al. (2006) "Transformation of Montmorency sour cherry (*Prunus cerasus* L.) and Gisela 6 (*P. cerasus* x *P. canescens*) cherry rootstock mediated by *Agrobacterium tumefaciens*," Plant Cell Rep. 25(2):117-123, online publication Dec. 21, 2005.

Taguchi et al. (2003) "Exogenously added naphthols induce three glucosyltransferases, and are accumulated as glucosides in tobacco cells," Plant Science 164:231-240.

Thompson et al. (1994) "Clustal W: improving the sensitivity of progressive multiple sequence alignment through sequence weighting, position-specific gap penalties and weight matrix choice," Nucleic Acids Research 22:4673-4680.

Till et al. (2003) "High-throughput TILLING for functional genomics," Methods Mol Biol 236:205-220. (Abstract only).

Veeriah et al. (Mar. 2006) "Apple Flavonoids Inhibit Growth of HT29 Human Colon Cancer Cells and Modulate Expression of Genes Involved in the Biotransformation of Xenobiotics," Molecular Carcinogenesis 45:164-174.

Vogt, T. (2000) "Glycosyltransferases involved in plant secondary metabolism," Chapter 10, Evolution of Metabolic Pathways, Romeo et al. (editors), pp. 317-347, Elsevier Science Ltd.

Wang et al. (Jan. 11, 2006) "Transformation of *Actinidia eriantha*: A potential species for functional genomics studies in *Actinidia*," Plant Cell Rep. 25(5):425-431.

Watts et al. (2004) "Exploring recombinant flavonoid Biosynthesis in Metabolically Engineered *Escherichia coli*," Chembiochem 5:500-507.

Wheeler et al. (2001) "Database resources of the National Center for Biotechnology Information," Nucleic Acids Research 29(1):11-16.

Whiting and Coggins (Jul. 1, 1975) "Estimation of the Monomeric Phenolics of Ciders," Journal of the Science of Food and Agriculture 26:1833-1838.

Yao et al. (1995) "Regeneration of transgenic plants from the commercial apple cultivar Royal Gala," Plant Cell Reports 14:407-412.

Zhang et al. (May 2, 2007) "Potential polyphenol markers of phase change in apple (*Malus domestica*)," Journal of Plant Physiology 164:574-580.

\* cited by examiner

Phloretin          Phlorizin

| Polypeptide | Md_88077 | Ms_297292 | Md_87623 | Md_138221 |
|---|---|---|---|---|
| Md_111441 | 99.79 | 99.59 | 98.96 | 82.4 |
| Md_88077 | | 99.38 | 98.76 | 82.19 |
| Ms_297292 | | | 98.96 | 81.99 |
| Md_87623 | | | | 82.4 |

SEQUENCE LISTING

<160> NUMBER OF SEQ ID NOS: 26

<210> SEQ ID NO 1
<211> LENGTH: 483
<212> TYPE: PRT
<213> ORGANISM: Malus domestica

<400> SEQUENCE: 1

```
Met Gly Asp Val Ile Val Leu Tyr Ala Ser Pro Gly Met Gly His Ile
1               5                   10                  15

Val Ser Met Val Glu Leu Gly Lys Phe Ile Val His Arg Tyr Gly Pro
            20                  25                  30

His Lys Phe Ser Ile Thr Ile Leu Tyr Thr Cys Gly Ser Ile Val Asp
        35                  40                  45

Thr Ala Ser Ile Pro Val Tyr Ile Arg Arg Ile Ser His Ser His Pro
    50                  55                  60

Phe Ile Ser Phe Arg Gln Phe Pro Arg Val Thr Asn Asn Ile Thr Arg
65                  70                  75                  80

Asn Ile Ser Val Pro Ala Ile Thr Phe Asp Phe Ile Arg Gln Asn Asp
                85                  90                  95

Pro His Val Arg Ser Ala Leu Gln Glu Ile Ser Lys Ser Ala Thr Val
            100                 105                 110

Arg Ala Phe Ile Ile Asp Leu Phe Cys Thr Ser Ala Leu Pro Ile Gly
        115                 120                 125

Lys Glu Phe Asn Ile Pro Thr Tyr Tyr Phe Cys Thr Ser Gly Ala Ala
    130                 135                 140

Ile Leu Ala Ala Phe Leu Tyr Leu Pro Lys Ile Asp Glu Gln Thr Lys
145                 150                 155                 160

Thr Thr Glu Ser Phe Lys Asp Leu Arg Asp Thr Val Phe Glu Phe Pro
                165                 170                 175

Gly Trp Lys Ser Pro Leu Lys Ala Thr His Met Val Gln Leu Val Leu
            180                 185                 190

Asp Arg Asn Asp Pro Ala Tyr Ser Asp Met Ile Tyr Phe Cys Ser His
        195                 200                 205

Leu Pro Lys Ser Asn Gly Ile Ile Val Asn Thr Phe Glu Glu Leu Glu
    210                 215                 220

Pro Pro Ser Val Leu Gln Ala Ile Ala Gly Gly Leu Cys Val Pro Asp
225                 230                 235                 240

Gly Pro Thr Pro Pro Val Tyr Tyr Val Gly Pro Leu Ile Glu Glu Glu
                245                 250                 255

Lys Glu Leu Ser Lys Asp Ala Asp Ala Ala Glu Lys Glu Asp Cys Leu
            260                 265                 270

Ser Trp Leu Asp Lys Gln Pro Ser Arg Ser Val Leu Phe Leu Cys Phe
        275                 280                 285

Gly Ser Met Gly Ser Phe Pro Ala Ala Gln Leu Lys Glu Ile Ala Asn
    290                 295                 300

Gly Leu Glu Ala Ser Gly Gln Arg Phe Leu Trp Val Val Lys Lys Pro
305                 310                 315                 320

Pro Val Glu Glu Lys Ser Lys Gln Val His Gly Val Asp Asp Phe Asp
                325                 330                 335

Leu Lys Gly Val Leu Pro Glu Gly Phe Leu Glu Arg Thr Ala Asp Arg
            340                 345                 350

Gly Met Val Val Lys Ser Trp Ala Pro Gln Val Val Val Leu Lys Lys
        355                 360                 365
```

```
Glu Ser Val Gly Gly Phe Val Thr His Cys Gly Trp Asn Ser Val Leu
    370                 375                 380

Glu Ala Val Val Ala Gly Val Pro Met Ile Ala Trp Pro Leu Tyr Ala
385                 390                 395                 400

Glu Gln His Met Asn Arg Asn Val Leu Val Thr Asp Met Glu Ile Ala
                405                 410                 415

Ile Gly Val Glu Gln Arg Asp Glu Glu Gly Phe Val Ser Gly Glu
                420                 425                 430

Glu Val Glu Arg Arg Val Arg Glu Leu Met Glu Ser Glu Gly Gly Arg
                435                 440                 445

Val Leu Arg Glu Arg Cys Lys Lys Leu Gly Met Ala Ser Ala Ala
    450                 455                 460

Leu Gly Glu Thr Gly Ser Ser Thr Arg Asn Leu Val Asn Phe Val Ser
465                 470                 475                 480

Ser Ile Thr

<210> SEQ ID NO 2
<211> LENGTH: 483
<212> TYPE: PRT
<213> ORGANISM: Malus sieboldii

<400> SEQUENCE: 2

Met Gly Asp Val Ile Val Leu Tyr Ala Ser Pro Gly Met Gly His Ile
1               5                   10                  15

Val Ala Met Val Glu Leu Gly Lys Phe Ile Val His Arg Tyr Gly Pro
                20                  25                  30

His Lys Phe Ser Ile Thr Ile Leu Tyr Thr Cys Gly Ser Ile Val Asp
            35                  40                  45

Thr Ala Ser Ile Pro Val Tyr Ile Arg Arg Ile Ser His Ser His Pro
    50                  55                  60

Phe Ile Ser Phe Arg Gln Phe Pro Arg Val Thr Asn Asn Ile Thr Arg
65                  70                  75                  80

Asn Ile Ser Val Pro Ala Ile Thr Phe Asp Phe Ile Arg Gln Asn Asp
                85                  90                  95

Pro His Val Arg Ser Ala Leu Gln Glu Ile Ser Lys Ser Ala Thr Val
            100                 105                 110

Arg Ala Phe Ile Ile Asp Leu Phe Cys Thr Ser Ala Leu Pro Ile Gly
        115                 120                 125

Lys Glu Phe Asn Ile Pro Thr Tyr Tyr Phe Cys Thr Ser Gly Ala Ala
    130                 135                 140

Ile Leu Ala Ala Phe Leu Tyr Leu Pro Lys Ile Asp Glu Gln Thr Lys
145                 150                 155                 160

Thr Thr Glu Ser Phe Lys Asp Leu Arg Asp Thr Val Phe Glu Phe Pro
                165                 170                 175

Gly Trp Lys Ser Pro Leu Lys Ala Thr His Met Val Gln Leu Val Leu
            180                 185                 190

Asp Arg Asn Asp Pro Ala Tyr Ser Asp Met Ile Tyr Phe Cys Ser His
        195                 200                 205

Leu Pro Lys Ser Asn Gly Ile Ile Val Asn Thr Phe Glu Glu Leu Glu
    210                 215                 220

Pro Pro Ser Val Leu Gln Ala Ile Ala Gly Gly Leu Cys Val Pro Asp
225                 230                 235                 240

Gly Pro Thr Pro Pro Val Tyr Tyr Val Gly Pro Leu Ile Glu Glu Glu
                245                 250                 255
```

```
Lys Glu Leu Ser Lys Asp Ala Asp Ala Ala Lys Glu Asp Cys Leu
            260                 265                 270

Ser Trp Leu Asp Lys Gln Pro Ser Arg Ser Val Leu Phe Leu Cys Phe
            275                 280                 285

Gly Ser Met Gly Ser Phe Pro Ala Ala Gln Leu Lys Glu Ile Ala Asn
            290                 295                 300

Gly Leu Glu Ala Ser Gly Gln Arg Phe Leu Trp Val Val Lys Lys Pro
305                 310                 315                 320

Pro Val Glu Glu Lys Ser Lys Gln Val His Gly Val Asp Asp Phe Asp
                    325                 330                 335

Leu Lys Gly Val Leu Pro Glu Gly Phe Leu Glu Arg Thr Ala Asp Arg
            340                 345                 350

Gly Met Val Val Lys Ser Trp Ala Pro Gln Val Val Leu Lys Lys
            355                 360                 365

Glu Ser Val Gly Gly Phe Val Thr His Cys Gly Trp Asn Ser Val Leu
            370                 375                 380

Glu Ala Val Val Ala Gly Val Pro Met Ile Ala Trp Pro Leu Tyr Ala
385                 390                 395                 400

Glu Gln His Met Asn Arg Asn Val Leu Val Thr Asp Met Glu Ile Ala
                    405                 410                 415

Ile Gly Val Glu Gln Arg Asp Glu Glu Gly Gly Phe Val Ser Gly Glu
            420                 425                 430

Glu Val Glu Arg Arg Val Arg Glu Leu Met Glu Ser Glu Gly Gly Arg
            435                 440                 445

Ala Leu Arg Glu Arg Cys Lys Lys Leu Gly Glu Met Ala Ser Ala Ala
            450                 455                 460

Leu Gly Glu Thr Gly Ser Ser Thr Arg Asn Leu Val Asn Phe Val Ser
465                 470                 475                 480

Ser Ile Thr

<210> SEQ ID NO 3
<211> LENGTH: 483
<212> TYPE: PRT
<213> ORGANISM: Malus domestica

<400> SEQUENCE: 3

Met Gly Asp Val Ile Val Leu Tyr Ala Ser Pro Gly Met Gly His Ile
1               5                   10                  15

Val Ser Met Val Glu Leu Gly Lys Phe Ile Val His Arg Tyr Gly Pro
            20                  25                  30

His Lys Phe Ser Ile Thr Ile Leu Tyr Thr Cys Gly Ser Ile Val Asp
            35                  40                  45

Thr Ala Ser Ile Pro Val Tyr Ile Arg Arg Ile Ser His Ser His Pro
        50                  55                  60

Phe Ile Ser Phe Arg Gln Phe Pro Arg Val Thr Asn Asn Ile Thr Arg
65              70                  75                  80

Asn Ile Ser Val Pro Ala Ile Thr Phe Asp Phe Ile Arg Gln Asn Asp
                    85                  90                  95

Pro His Val Arg Ser Ala Leu Gln Glu Ile Ser Lys Ser Ala Thr Val
            100                 105                 110

Arg Ala Phe Ile Ile Asp Leu Phe Cys Thr Ser Ala Leu Pro Ile Gly
            115                 120                 125

Lys Glu Phe Asn Ile Pro Thr Tyr Tyr Phe Cys Thr Ser Gly Ala Ala
            130                 135                 140
```

```
Ile Leu Ala Ala Phe Leu Tyr Leu Pro Lys Ile Asp Glu Gln Thr Lys
145                 150                 155                 160

Thr Thr Glu Ser Phe Lys Asp Leu Arg Asp Thr Val Phe Glu Phe Pro
                165                 170                 175

Gly Trp Lys Ser Pro Leu Lys Ala Thr His Met Val Gln Leu Val Leu
            180                 185                 190

Asp Arg Asn Asp Pro Ala Tyr Ser Asp Met Ile Tyr Phe Cys Ser His
        195                 200                 205

Leu Pro Lys Ser Asn Gly Ile Ile Val Asn Thr Phe Glu Glu Leu Glu
    210                 215                 220

Pro Pro Ser Val Leu Gln Ala Ile Ala Gly Gly Leu Cys Val Pro Asp
225                 230                 235                 240

Gly Pro Thr Pro Pro Val Tyr Tyr Val Gly Pro Leu Ile Glu Glu Glu
                245                 250                 255

Lys Glu Leu Ser Lys Asp Ala Asp Ala Ala Glu Lys Glu Asp Cys Leu
            260                 265                 270

Ser Trp Leu Asp Lys Gln Pro Ser Arg Ser Val Leu Phe Leu Cys Phe
        275                 280                 285

Gly Ser Met Gly Ser Phe Pro Ala Ala Gln Leu Lys Glu Ile Ala Asn
    290                 295                 300

Gly Leu Glu Ala Ser Gly Gln Arg Phe Leu Trp Val Val Lys Lys Pro
305                 310                 315                 320

Pro Val Glu Glu Lys Ser Lys Gln Val His Gly Val Asp Asp Phe Asp
                325                 330                 335

Leu Lys Gly Val Leu Pro Glu Gly Phe Leu Glu Arg Thr Ala Asp Arg
            340                 345                 350

Gly Met Val Val Lys Ser Trp Ala Pro Gln Val Val Leu Lys Lys
        355                 360                 365

Glu Ser Val Gly Gly Phe Val Thr His Cys Gly Trp Asn Ser Val Leu
    370                 375                 380

Glu Ala Val Val Ala Gly Val Pro Met Ile Ala Trp Pro Leu Tyr Ala
385                 390                 395                 400

Glu Gln His Met Asn Arg Asn Val Leu Val Thr Asp Met Glu Leu Ala
                405                 410                 415

Ile Gly Val Glu Gln Arg Asp Glu Glu Gly Phe Val Ser Gly Glu
            420                 425                 430

Glu Val Glu Arg Arg Val Arg Glu Leu Met Glu Ser Glu Gly Gly Arg
        435                 440                 445

Val Leu Arg Glu Arg Cys Lys Lys Leu Gly Glu Met Ala Ser Ala Ala
    450                 455                 460

Leu Gly Glu Thr Gly Ser Ser Thr Arg Asn Leu Val Asn Phe Val Ser
465                 470                 475                 480

Ser Ile Thr

<210> SEQ ID NO 4
<211> LENGTH: 483
<212> TYPE: PRT
<213> ORGANISM: Malus domestica

<400> SEQUENCE: 4

Met Gly Asp Val Ile Val Leu Tyr Ala Ser Pro Gly Met Gly His Ile
1               5                   10                  15

Val Ser Met Val Glu Leu Gly Lys Phe Ile Val His Arg Tyr Gly Pro
            20                  25                  30
```

-continued

```
His Lys Phe Ser Ile Thr Ile Leu Tyr Thr Cys Gly Ser Ile Val Asp
             35                  40                  45

Thr Ala Ser Ile Pro Val Tyr Ile Arg Arg Ile Ser His Ser His Pro
 50                  55                  60

Phe Ile Ser Phe Arg Gln Phe Pro Arg Val Thr Asn Asn Ile Thr Arg
 65                  70                  75                  80

Asn Ile Ser Val Pro Ala Ile Thr Phe Asp Phe Ile Arg Gln Asn Asp
                 85                  90                  95

Pro His Val Arg Ser Ala Leu Gln Glu Ile Ser Lys Ser Ala Thr Val
            100                 105                 110

Arg Ala Phe Ile Ile Asp Leu Phe Cys Thr Ser Ala Leu Pro Ile Gly
        115                 120                 125

Lys Glu Phe Asn Ile Pro Thr Tyr Tyr Phe Cys Thr Ser Gly Ala Ala
    130                 135                 140

Ile Leu Ala Ala Phe Leu Tyr Leu Pro Lys Ile Asp Glu Gln Thr Lys
145                 150                 155                 160

Thr Thr Glu Ser Phe Lys Asp Leu Arg Asp Thr Val Phe Glu Phe Pro
                165                 170                 175

Gly Trp Lys Ser Pro Leu Lys Ala Pro His Met Val Gln Leu Val Leu
            180                 185                 190

Asp Arg Asn Asp Pro Ala Tyr Ser Asp Met Ile Tyr Phe Cys Ser His
        195                 200                 205

Leu Pro Lys Ser Asn Gly Ile Ile Val Asn Thr Phe Glu Glu Leu Glu
    210                 215                 220

Pro Pro Ala Val Leu Gln Ala Ile Ala Gly Gly Leu Cys Val Pro Asp
225                 230                 235                 240

Gly Pro Thr Pro Pro Val Tyr Tyr Val Gly Pro Leu Ile Glu Glu Glu
                245                 250                 255

Lys Glu Leu Ser Lys Asp Ala Asp Ala Ala Gly Glu Glu Asp Cys Leu
            260                 265                 270

Ser Trp Leu Asp Lys Gln Pro Ser Arg Ser Val Leu Phe Leu Cys Phe
        275                 280                 285

Gly Ser Met Gly Ser Phe Pro Ala Ala Gln Leu Lys Glu Ile Ala Asn
    290                 295                 300

Gly Leu Glu Ala Ser Gly Gln Arg Phe Leu Trp Val Val Lys Lys Pro
305                 310                 315                 320

Pro Val Glu Glu Lys Ser Lys Gln Val His Gly Val Asp Asp Phe Asp
                325                 330                 335

Leu Lys Gly Val Leu Pro Glu Gly Phe Leu Glu Arg Thr Ala Asp Arg
            340                 345                 350

Gly Met Val Val Lys Ser Trp Ala Pro Gln Val Val Leu Lys Lys
        355                 360                 365

Glu Ser Val Gly Gly Phe Val Thr His Cys Gly Trp Asn Ser Val Leu
    370                 375                 380

Glu Ala Val Val Ala Gly Val Pro Met Ile Ala Trp Pro Leu Tyr Ala
385                 390                 395                 400

Glu Gln His Met Asn Arg Asn Val Leu Val Thr Asp Met Glu Ile Ala
                405                 410                 415

Ile Gly Val Glu Gln Arg Asp Glu Gly Gly Phe Val Ser Gly Glu
            420                 425                 430

Glu Val Glu Arg Arg Val Arg Glu Leu Met Glu Ser Glu Gly Gly Arg
        435                 440                 445

Ala Leu Arg Glu Arg Cys Lys Lys Leu Gly Glu Met Ala Ser Ala Ala
```

450                 455                 460
Leu Gly Glu Thr Gly Ser Ser Thr Arg Asn Leu Val Asn Phe Val Ser
465                 470                 475                 480

Ser Ile Thr

<210> SEQ ID NO 5
<211> LENGTH: 480
<212> TYPE: PRT
<213> ORGANISM: Malus domestica

<400> SEQUENCE: 5

Met Gly Asp Val Ile Val Leu Tyr Ala Ala Pro Gly Met Gly His Val
1               5                   10                  15

Ile Ser Met Val Glu Leu Gly Lys Leu Ile Leu His Arg Tyr Gly Pro
                20                  25                  30

His Lys Phe Ser Ile Thr Ile Leu Tyr Thr Cys Gly Ser Phe Phe Asp
            35                  40                  45

Thr Pro Ser Ile Pro Ala Tyr Ile Arg Arg Ile Ser His Ser His Pro
        50                  55                  60

Ser Ile Ser Phe Arg Gln Phe Pro Arg Val Thr Asn Lys Ile Thr Gln
65                  70                  75                  80

Asn Ile Ser Gly Thr Ala Ile Val Val Asp Phe Val Arg Gln Asn Asp
                85                  90                  95

Pro His Val Arg Arg Ala Leu Gln Asp Ile Ser Lys Ser Ala Val Val
            100                 105                 110

Arg Ala Phe Ile Ile Asp Leu Val Cys Thr Ser Ala Met Thr Ile Ser
        115                 120                 125

Lys Glu Phe Asp Ile Pro Thr Tyr Tyr Phe Tyr Thr Ser Gly Ala Ala
130                 135                 140

Ala Leu Gly Ala Phe Leu Tyr Phe Pro Lys Ile His Glu Gln Thr Thr
145                 150                 155                 160

Gln Ser Phe Lys Asp Leu Thr Asp Thr Val Ile Glu Phe Pro Gly Arg
                165                 170                 175

Lys Ser Pro Leu Lys Ala Ile His Met Ile Glu Pro Leu Leu Asp Arg
            180                 185                 190

Asp Asp Pro Ala Tyr Trp Asp Phe Leu Ser Phe Cys Ser Asp Leu Pro
        195                 200                 205

Lys Ser Lys Gly Ile Ile Val Asn Thr Phe Glu Glu Leu Glu Pro Pro
210                 215                 220

Ala Val Leu His Ala Ile Ala Glu Gly Leu Cys Val Pro Asp Gly Pro
225                 230                 235                 240

Thr Ser Pro Val Tyr Tyr Val Gly Pro Leu Ile Asp Glu Glu Lys Val
                245                 250                 255

Ser Gly Asn Asp Ala Ala Ala Glu Glu Asp Cys Leu Ser Trp Leu
            260                 265                 270

Asp Lys Gln Pro Ser Arg Ser Val Val Phe Leu Cys Phe Gly Ser Arg
        275                 280                 285

Gly Ser Leu Pro Ala Ile Gln Leu Lys Glu Ile Ala Lys Ala Leu Glu
290                 295                 300

Ala Ser Gly Gln Arg Phe Leu Trp Val Val Lys Lys Pro Val Asp
305                 310                 315                 320

Glu Lys Thr Lys Gln Val Leu Gly Val Asp Phe Asp Leu Glu Gly
                325                 330                 335

Val Leu Pro Glu Gly Phe Leu Glu Arg Thr Lys Asp Arg Gly Met Val

```
      340                 345                 350
Val Lys Ser Trp Ala Pro Gln Ala Glu Val Lys Lys Glu Ser Val
                355                 360                 365

Gly Gly Phe Val Thr His Cys Gly Trp Asn Ser Val Leu Glu Ala Val
        370                 375                 380

Val Ala Gly Val Pro Met Ile Ala Trp Pro Leu Tyr Ala Glu Gln His
385                 390                 395                 400

Leu Asn Arg Asn Val Met Ala Thr Asp Met Glu Ile Ala Ile Ala Val
                405                 410                 415

Glu Gln Arg Asp Glu Asp Gly Phe Val Ser Gly Glu Glu Leu Glu
            420                 425                 430

Arg Arg Val Arg Glu Leu Met Glu Ser Glu Glu Gly Arg Val Leu Arg
                435                 440                 445

Glu Arg Ser Lys Lys Ile Gly Glu Met Ala Met Ala Ala Leu Gly Glu
            450                 455                 460

Asn Gly Ser Ser Thr Arg Asn Leu Val Asn Phe Val Asn Ser Leu Thr
465                 470                 475                 480

<210> SEQ ID NO 6
<211> LENGTH: 1696
<212> TYPE: DNA
<213> ORGANISM: Malus domestica

<400> SEQUENCE: 6
gtcgcagctg ccgccatggg agacgtcatt gtactgtacg catctccggg gatggggcat      60
atcgtctcca tggtggagct gggcaagttc attgtccacc gctacggccc ccacaaattc     120
tccatcacca ttctctacac ctgcggcagc attgtcgaca ccgctagcat ccccgtctac     180
atccgccgca tctcccactc ccacccttc atttccttcc gccaattccc tcgcgtcacc     240
aataatatta cccgaaacat aagcgtcccc gcaatcacgt tcgacttcat ccgccagaac     300
gatcctcatg tccgcagtgc cctccaagaa atctctaaat ccgccaccgt tcgcgccttc     360
atcatcgacc tcttctgcac ctccgctctt cccatagga aggaattcaa catcccaaca     420
tactacttct gcacttctgg tgccgcaatt cttgctgctt ttttgtattt gcccaagatc     480
gatgagcaaa ccaaaaccac cgagagtttc aaagacctcc gcgacaccgt tttcgaattc     540
cccggatgga gtctcctct gaaggctaca cacatggtcc aactggtgct cgaccggaac     600
gaccctgctt attcggacat gatctatttc tgctcacatc ttcccaaatc caacggaatc     660
atcgtcaaca cgttcgaaga gctcgagcca cctagcgtcc tccaggccat gctggaggc      720
ctgtgtgttc ctgatgggcc aactccgccc gtgtactacg ttggtccatt gattgaggaa     780
gagaaagaat tgagtaagga tgcagatgcg gccgagaagg aggactgctt gtcatggctc     840
gataagcagc caagtcgaag cgtgctgttt ctctgtttcg gaagcatggg atcattccg      900
gctgctcaac tgaaggagat agcgaacggg ttggaggcga gcgggcagag gttcctgtgg     960
gtggtgaaga agccgccggt tgaagagaaa tcaaagcagg tccatggagt tgacgacttt    1020
gatttgaagg gtgtgttgcc agaagggttt ttggagagga cggccgacag ggggatggta    1080
gtgaagtcat gggcgccgca ggtggtggtg ttgaagaagg agtcggttgg tgggttcgtg    1140
acacattgcg gatggaactc ggtactggaa gcagtggttg cggggtgcc gatgattgct    1200
tggccgcttt acgcggagca gcatatgaac aggaatgttc tagtgacgga catggaaatc    1260
gcgatcgggg tggagcagag agacgaggaa ggtgggttcg tgagcgggga agaagtggag    1320
aggagagtga gggagttgat ggagtcggaa ggaggaagag tgcttagaga gaggtgcaag    1380
```

```
aaacttgggg agatggcttc ggctgctttg ggagagaccg gttcgtccac cagaaacttg    1440
gtcaactttg ttagtagcat tacataaccg tgcaagtttt gggttcgcat ttcgcatttg    1500
gatttcgaga ggagtcgtgt gcaagaataa accctcttaa ccaactccgc gatatggttt    1560
tctgttactt agtttggcac ctcgtgggat tttggtgctc tcttttgaga gttttaagaa    1620
agcatcaaac tattcggatg taatgttgat gtaacgtcga ccatcagctt aattccaacc    1680
aataagatta tgtaaa                                                   1696

<210> SEQ ID NO 7
<211> LENGTH: 1452
<212> TYPE: DNA
<213> ORGANISM: Malus domestica

<400> SEQUENCE: 7
atgggagacg tcattgtact gtacgcatct ccggggatgg ggcatatcgt ctccatggtg      60
gagctgggca agttcattgt ccaccgctac ggccccaca  aattctccat caccattctc     120
tacacctgcg gcagcattgt cgacaccgct agcatccccg tctacatccg ccgcatctcc     180
cactcccacc ctttcatttc cttccgccaa ttccctcgcg tcaccaataa tattacccga     240
aacataagcg tccccgcaat cacgttcgac ttcatccgcc agaacgatcc tcatgtccgc     300
agtgccctcc aagaaatctc taaatccgcc accgttcgcg ccttcatcat cgacctcttc     360
tgcacctccg ctcttcccat agggaaggaa ttcaacatcc aacatacta  cttctgcact     420 tctggtgccg caattcttgc tgcttttttg tatttgccca agatcgatga gcaaaccaaa     480
accaccgaga gtttcaaaga cctccgcgac accgttttcg aattccccgg atggaagtct     540
cctctgaagg ctacacacat ggtccaactg gtgctcgacc ggaacgaccc tgcttattcg     600
gacatgatct atttctgctc acatcttccc aaatccaacg gaatcatcgt caacacgttc     660
gaagagctcg agccacctag cgtcctccag gccattgctg gaggcctgtg tgttcctgat     720
gggccaactc cgcccgtgta ctacgttggt ccattgattg aggaagagaa agaattgagt     780
aaggatgcag atgcggccga gaaggaggac tgcttgtcat ggctcgataa gcagccaagt     840
cgaagcgtgc tgtttctctg tttcggaagc atgggatcat ttccggctgc tcaactgaag     900
gagatagcga acgggttgga ggcgagcggg cagaggttcc tgtgggtggt gaagaagccg     960
ccggttgaag agaaatcaaa gcaggtccat ggagttgacg actttgattt gaagggtgtg    1020
ttgccagaag ggttttggga ggaacggcc  gacaggggga tggtagtgaa gtcatgggcg    1080
ccgcaggtgt tggtgttgaa gaaggagtcg gttggtgggt cgtgacaca  ttgcggatgg    1140 aactcggtac tggaagcagt ggttgcgggg gtgccgatga ttgcttggcc gctttacgcg    1200
gagcagcata tgaacaggaa tgttctagtg acggacatgg aaatcgcgat cggggtggag    1260
cagagagacg aggaaggtgg gttcgtgagc ggggaagaag tggagaggag agtgagggag    1320
ttgatggagt cggaaggagg aagagtgctt agagagaggt gcaagaaact tggggagatg    1380
gcttcggctg ctttgggaga gaccggttcg tccaccagaa acttggtcaa ctttgttagt    1440
agcattacat aa                                                       1452

<210> SEQ ID NO 8
<211> LENGTH: 1714
<212> TYPE: DNA
<213> ORGANISM: Malus sieboldii

<400> SEQUENCE: 8
```

```
cgcagctgcc gccatgggag acgtcattgt actgtacgca tctccaggga tggggcacat    60
cgtcgccatg gtggagctgg gcaagttcat tgtccaccgc tacggccccc acaaattctc   120
catcaccatt ctctacacct gcggcagcat tgtcgacacc gctagcatcc ccgtctacat   180
ccgccgcatc tcccactccc acccttttcat ttccttccgc caattccctc gcgtcaccaa   240
taatattacc cgaaacataa gcgtccccgc aatcacgttc gacttcatcc gccagaacga   300
tcctcatgtc cgcagtgccc tccaagaaat ctctaaatcc gccaccgttc gcgccttcat   360
catcgacctc ttctgcacct ccgctcttcc catagggaag gaattcaaca tcccaacata   420
ctacttctgc acttctggtg ccgcaattct tgctgctttt ttgtatttgc caagatcga    480
tgagcaaacc aaaaccaccg agagtttcaa agacctccgc gacaccgttt tcgaattccc   540
cggatggaag tctcctctga aggctacaca catggtccaa ctggtgctcg accgaacga    600
ccctgcttat tcggacatga tctatttctg ctcacatctt cccaaatcca acggaatcat   660
cgtcaacacg ttcgaagagc tcgagccacc tagcgtcctc caggccattg ctggaggcct   720
gtgtgttcct gatgggccaa ctccgcccgt gtactacgtt ggtccattga ttgaggaaga   780
gaaagaattg agtaaggatg cagatgcggc cgagaaggag gactgcttgt catggctcga   840
taagcagcca agtcgaagcg tgctgttttct ctgtttcgga agcatgggat catttccggc   900
tgctcaactg aaggagatag cgaacgggtt ggaggcgagc gggcagaggt tcctgtgggt   960
ggtgaagaag ccgccggttg aagagaaatc aaagcaggtc catggagttg acgactttga  1020
tttgaagggt gtgttgccag aagggttttt ggagaggacg gcagacaggg gatggtagt   1080
gaagtcatgg gcgccgcagg tggtggtgtt gaagaaggag tcggttggtg ggttcgtgac  1140
acattgcgga tggaactcgg tactggaagc agtggttgcg ggggtgccga tgattgcttg  1200
gccgctttac gcggagcagc atatgaacag gaatgttcta gtgacggaca tggaaatcgc  1260
gatcggggtg gagcagagag acgaggaagg tgggttcgtg agcggggaag aagtggagag  1320
gagagtgagg gagttgatgg agtcggaagg aggaagagcg cttagagaga ggtgcaagaa  1380
acttggggag atggcttcgg ctgctttggg agagaccggt tcgtccacca gaaacttggt  1440
caactttgtt agtagcatta cataaccgtg caagttttgg gttcgcattt cgcatttgga  1500
tttcgagagg agtcgtgtgc aagaataaac cctcttaacc aactccgcga tatggttttc  1560
tgttacttag tttggcacct cgtgggattt tggtgctctc ttttgagagt tttaagaaag  1620
catcaaacta ttcggatgta atgttgatgt aacgtcgacc atcagcttaa ttccaaccaa  1680
taagattatg tacttctttc ttaaaaaaaa aaaa                              1714

<210> SEQ ID NO 9
<211> LENGTH: 1452
<212> TYPE: DNA
<213> ORGANISM: Malus sieboldii

<400> SEQUENCE: 9
atgggagacg tcattgtact gtacgcatct ccaggatgg ggcacatcgt cgccatggtg    60
gagctgggca agttcattgt ccaccgctac ggcccccaca aattctccat caccattctc   120
tacacctgcg gcagcattgt cgacaccgct agcatcccg tctacatccg ccgcatctcc   180
cactcccacc ctttcatttc cttccgccaa ttccctcgcg tcaccaataa tattacccga   240
aacataagcg tccccgcaat cacgttcgac ttcatccgcc agaacgatcc tcatgtccgc   300
agtgccctcc aagaaatctc taaatccgcc accgttcgcg ccttcatcat cgacctcttc   360
tgcacctccg ctcttcccat agggaaggaa ttcaacatcc aacatacta cttctgcact   420
```

```
tctggtgccg caattcttgc tgcttttttg tatttgccca agatcgatga gcaaaccaaa    480
accaccgaga gtttcaaaga cctccgcgac accgttttcg aattccccgg atggaagtct    540
cctctgaagg ctacacacat ggtccaactg gtgctcgacc ggaacgaccc tgcttattcg    600
gacatgatct atttctgctc acatcttccc aaatccaacg gaatcatcgt caacacgttc    660
gaagagctcg agccacctag cgtcctccag gccattgctg gaggcctgtg tgttcctgat    720
gggccaactc cgcccgtgta ctacgttggt ccattgattg aggaagagaa agaattgagt    780
aaggatgcag atgcggccga gaaggaggac tgcttgtcat ggctcgataa gcagccaagt    840
cgaagcgtgc tgtttctctg tttcggaagc atgggatcat ttccggctgc tcaactgaag    900
gagatagcga acgggttgga ggcgagcggg cagaggttcc tgtgggtggt gaagaagccg    960
ccggttgaag agaaatcaaa gcaggtccat ggagttgacg actttgattt gaagggtgtg   1020
ttgccagaag ggttttttgga gaggacggca gacagggga tggtagtgaa gtcatgggcg    1080
ccgcaggtgg tggtgttgaa gaaggagtcg gttggtgggt cgtgacaca ttgcggatgg    1140
aactcggtac tggaagcagt ggttgcgggg gtgccgatga ttgcttggcc gctttacgcg    1200
gagcagcata tgaacaggaa tgttctagtg acggacatgg aaatcgcgat cggggtggag    1260
cagagagacg aggaaggtgg gttcgtgagc ggggaagaag tggagaggag agtgagggag    1320
ttgatggagt cggaaggagg aagagcgctt agagagaggt gcaagaaact ggggagatg    1380
gcttcggctg ctttgggaga gaccggttcg tccaccagaa acttggtcaa ctttgttagt    1440
agcattacat aa                                                       1452

<210> SEQ ID NO 10
<211> LENGTH: 1722
<212> TYPE: DNA
<213> ORGANISM: Malus domestica

<400> SEQUENCE: 10
ccaccagtcg cagctgccgc catgggagac gtcattgtac tgtacgcatc tccggggatg      60
gggcatatcg tctccatggt ggagctgggc aagttcattg tccaccgcta cggccccac    120
aaattctcca tcaccattct ctacacctgc ggcagcattg tcgacaccgc tagcatcccc    180
gtctacatcc gccgcatctc ccactccac cctttcattt ccttccgcca attccctcgc    240
gtcaccaata atattacccg aaacataagc gtccccgcaa tcacgttcga cttcatccgc    300
cagaacgatc ctcatgtccg cagtgccctc caagaaatct ctaaatccgc caccgttcgc    360
gccttcatca tcgacctctt ctgcacctcc gctcttccca tagggaagga attcaacatc    420
ccaacatact acttctgcac ttctggtgcc gcaattcttg ctgctttttt gtatttgccc    480
aagatcgatg agcaaaccaa aaccaccgag agtttcaaag acctccgcga caccgttttc    540
gaattccccg gatggaagtc tcctctgaag gctacacaca tggtccaact ggtgctcgac    600
cggaacgacc ctgcttattc ggacatgatc tatttctgct cacatcttcc caaatccaac    660
ggaatcatcg tcaacacgtt cgaagagctc gagccaccta gcgtcctcca ggccattgct    720
ggaggcctgt gtgttcctga tgggccaact ccgcccgtgt actacgttgg tccattgatt    780
gaggaagaga agaattgag taaggatgca gatgcggccg agaaggagga ctgcttgtca    840
tggctcgata gcagccaag tcgaagcgtg ctgtttctct gtttcggaag catgggatca    900
tttccggctg ctcaactgaa ggagatagcg aacgggttgg aggcgagcgg gcagaggttc    960
ctgtgggtgg tgaagaagcc gccggttgaa gagaaatcaa agcaggtcca tggagttgac   1020
```

-continued

```
gactttgatt tgaagggtgt gttgccagaa gggttttgg agaggacggc cgacagggggg    1080 atggtagtga agtcatgggc gccgcaggtg gtggtgttga agaaggagtc ggttggtggg    1140
ttcgtgacac attgcggatg gaactcggta ctggaagcag tggttgcggg ggtgccgatg    1200
attgcttggc cgctttacgc ggagcagcat atgaacagga atgttctagt gacggacatg    1260
gaactcgcga tcggggtgga gcagagagac gaggaaggtg ggttcgtgag cggggaagaa    1320
gtggagagga gagtgaggga gttgatggag tcggaaggag gaagagtgct tagagagagg    1380
tgcaagaaac ttggggagat ggcttcggct gctttgggag agaccggttc gtccaccaga    1440
aacttggtca actttgttag tagcattaca taaccgtgca agttttgggt tcgcatttcg    1500
catttggatt tcgagaggag tcgtgtgcaa gaataaaccc tcttaaccaa ctccgcgata    1560
tggttttctg ttacttagtt tggcacctcg tgggattttg gtgctctctt ttgagagttt    1620
taagaaagca tcaaactatt cggatgtaat gttgatgtaa cgtcgaccat cagcttaatt    1680
ccaaccaata agattatgta cttctttctt aaaaaaaaaa aa                       1722

<210> SEQ ID NO 11
<211> LENGTH: 1451
<212> TYPE: DNA
<213> ORGANISM: Malus domestica

<400> SEQUENCE: 11
tgggagacgt cattgtactg tacgcatctc cggggatggg gcatatcgtc tccatggtgg      60
agctgggcaa gttcattgtc caccgctacg gcccccacaa attctccatc accattctct     120
acacctgcgg cagcattgtc gacaccgcta gcatccccgt ctacatccgc cgcatctccc     180
actcccaccc tttcatttcc ttccgccaat ccctcgcgt caccaataat attacccgaa      240
acataagcgt ccccgcaatc acgttcgact tcatccgcca gaacgatcct catgtccgca     300
gtgccctcca agaaatctct aaatccgcca ccgttcgcgc cttcatcatc gacctcttct     360
gcacctccgc tcttcccata gggaaggaat tcaacatccc aacatactac ttctgcactt     420
ctggtgccgc aattcttgct gctttttgt atttgcccaa gatcgatgag caaaccaaaa      480
ccaccgagag tttcaaagac ctccgcgaca ccgttttcga attccccgga tggaagtctc     540
ctctgaaggc tacacacatg gtccaactgg tgctcgaccg gaacgaccct gcttattcgg     600
acatgatcta tttctgctca catcttccca atccaacgg aatcatcgtc aacacgttcg     660
aagagctcga gccacctagc gtcctccagg ccattgctgg aggcctgtgt gttcctgatg     720
ggccaactcc gcccgtgtac tacgttggtc cattgattga ggaagagaaa gaattgagta    780
aggatgcaga tgcggccgag aaggaggact gcttgtcatg gctcgataag cagccaagtc    840
gaagcgtgct gtttctctgt ttcggaagca tgggatcatt tccggctgct caactgaagg    900
agatagcgaa cggggttggag gcgagcgggc agaggttcct gtgggtggtg aagaagccgc    960
cggttgaaga gaaatcaaag caggtccatg gagttgacga ctttgatttg aagggtgtgt   1020
tgccagaagg gttttggag aggacggccg acagggggat ggtagtgaag tcatgggcgc    1080
cgcaggtggt ggtgttgaag aaggagtcgg ttggtgggtt cgtgacacat gcggatgga    1140 actcggtact ggaagcagtg gttgcggggg tgccgatgat tgcttggccg ctttacgcgg   1200
agcagcatat gaacaggaat gttctagtga cggacatgga actcgcgatc ggggtggagc   1260
agagagacga ggaaggtggg ttcgtgagcg ggaagaagt ggagaggaga gtgagggagt    1320
tgatggagtc ggaaggagga agagtgctta gagagaggtg caagaaactt ggggagatgg    1380
cttcggctgc tttgggagag accggttcgt ccaccagaaa cttggtcaac tttgttagta    1440
```

```
gcattacata a                                                           1451

<210> SEQ ID NO 12
<211> LENGTH: 1719
<212> TYPE: DNA
<213> ORGANISM: Malus domestica

<400> SEQUENCE: 12
gtcgcagctg ccgccatggg agacgtcatt gtactgtacg catctccggg gatggggcac         60
atcgtctcca tggtggagct gggcaagttc attgtccacc gctacggccc ccacaaattc        120
tccatcacca ttctctacac ctgcggcagc attgtcgaca ccgctagcat ccccgtctac        180
atccgccgca tctcccactc ccacccttc atttccttcc gccaattccc tcgcgtcacc        240
aataatatta cccgaaacat aagcgtcccc gcaatcacgt tcgacttcat ccgccagaac        300
gatcctcatg tccgcagtgc cctccaagaa atctctaaat ccgccaccgt tcgcgccttc        360
atcatcgacc tcttctgcac ctccgctctt cccataggga aggaattcaa catcccaaca        420
tactacttct gcacttctgg agccgcaatt cttgctgctt ttttgtattt gcccaagatc        480
gatgagcaaa ccaaaaccac cgagagtttc aaagacctcc gcgacaccgt tttcgaattc        540
cccggatgga agtctcctct gaaggctcca cacatggtcc aactggtgct cgaccggaac        600
gaccctgctt attcggacat gatctatttc tgctcacatc ttcccaaatc caacggaatc        660
atcgtcaaca cgttcgaaga gctcgagcca cctgccgtcc tccaggccat tgctggaggc        720
ctgtgtgttc ctgatgggcc aactccgccc gtgtactacg ttggtccatt gattgaggaa        780
gagaaagaat tgagtaagga tgcagatgcg gccggggagg aggactgctt gtcatggctc        840
gataagcagc caagtcgaag cgtgctgttt ctctgtttcg gaagcatggg atcatttccg        900
gctgctcaac tgaaggagat agcgaacggg ttggaggcga gcgggcagag gttcctgtgg        960
gtggtgaaga agccgccggt tgaagagaaa tcaaagcagg tccatggagt tgacgacttt       1020
gatttgaagg gtgtgttgcc agaagggttt ttggagagga cggccgacag ggggatggta       1080
gtgaagtcat gggcgccgca ggtggtggtg ttgaagaagg agtcggttgg tgggttcgtg       1140
acacattgcg gatggaactc ggtactgaa gcagtggttg cggggtgcc gatgattgct       1200 tggccgcttt acgcggagca gcatatgaac aggaatgttc tagtgacgga catggaaatc       1260
gcgatcgggg tggagcagag agacgaggaa ggtgggttcg tgagcgggga agaagtggag       1320
aggagagtga gggagttgat ggagtcggaa ggaggaagag cgcttagaga gaggtgcaag       1380
aaacttgggg agatggcttc ggctgctttg ggagagaccg ttcgtccac cagaaacttg       1440 gtcaactttg ttagtagcat tacataaccg tgcaagtttt gggttcgcat ttcgcatttg       1500
gatttcgaga ggagtcgtgt gcaagaataa accctcttaa ccaactccgc gatatggttt       1560
tctgttactt agtttggcac ctcgtgggat tttggtgctc tcttttgaga gttttaagaa       1620
agcatcaaac tattcggatg taatgttgat gtaacgtcga ccatcagctt aattccaacc       1680
aataagatta tctacttctt tcttaccaaa aaaaaaaaa                             1719

<210> SEQ ID NO 13
<211> LENGTH: 1452
<212> TYPE: DNA
<213> ORGANISM: Malus domestica

<400> SEQUENCE: 13
atgggagacg tcattgtact gtacgcatct ccggggatgg ggcacatcgt ctccatggtg         60
```

```
gagctgggca agttcattgt ccaccgctac ggcccccaca aattctccat caccattctc      120
tacacctgcg gcagcattgt cgacaccgct agcatcccg tctacatccg ccgcatctcc      180
cactcccacc ctttcatttc cttccgccaa ttccctcgcg tcaccaataa tattacccga      240
aacataagcg tccccgcaat cacgttcgac ttcatccgcc agaacgatcc tcatgtccgc      300
agtgccctcc aagaaatctc taaatccgcc accgttcgcg ccttcatcat cgacctcttc      360
tgcacctccg ctcttcccat agggaaggaa ttcaacatcc aacatacta cttctgcact      420 tctggagccg caattcttgc tgctttttg tatttgccca agatcgatga gcaaaccaaa      480
accaccgaga gtttcaaaga cctccgcgac accgttttcg aattccccgg atggaagtct      540
cctctgaagg ctccacacat ggtccaactg gtgctcgacc ggaacgaccc tgcttattcg      600
gacatgatct atttctgctc acatcttccc aaatccaacg gaatcatcgt caacacgttc      660
gaagagctcg agccacctgc cgtcctccag gccattgctg gaggcctgtg tgttcctgat      720
gggccaactc cgcccgtgta ctacgttggt ccattgattg aggaagagaa agaattgagt      780
aaggatgcag atgcggccgg ggaggaggac tgcttgtcat ggctcgataa gcagccaagt      840
cgaagcgtgc tgtttctctg tttcggaagc atgggatcat ttccggctgc tcaactgaag      900
gagatagcga acgggttgga ggcgagcggg cagaggttcc tgtgggtggt gaagaagccg      960
ccggttgaag agaaatcaaa gcaggtccat ggagttgacg actttgattt gaagggtgtg     1020
ttgccagaag ggttttttgga gaggacggcc gacaggggga tggtagtgaa gtcatgggcg     1080
ccgcaggtgg tggtgttgaa gaaggagtcg gttggtgggt tcgtgacaca ttgcggatgg     1140
aactcggtac tggaagcagt ggttgcgggg gtgccgatga ttgcttggcc gctttacgcg     1200
gagcagcata tgaacaggaa tgttctagtg acggacatgg aaatcgcgat cggggtggag     1260
cagagagacg aggaaggtgg gttcgtgagc ggggaagaag tggagaggag agtgagggag     1320
ttgatggagt cggaaggagg aagagcgctt agagagaggt gcaagaaact ggggagatg      1380 gcttcggctg cttgggaga gaccggttcg tccaccagaa acttggtcaa ctttgttagt     1440
agcattacat aa                                                        1452

<210> SEQ ID NO 14
<211> LENGTH: 1659
<212> TYPE: DNA
<213> ORGANISM: Malus domestica

<400> SEQUENCE: 14
ctcaaatcaa atcagataat ttcagcagaa aacacaacac acaaatcagc agcagcagct       60
gccatgggag acgtaatagt gctgtacgca gctccaggaa tggggcatgt catctccatg      120
gtggagctgg gcaagctcat cctccaccgc tacggccccc acaagttttc catcaccatt      180
ctctacacct gcggcagctt cttcgacacc cctagcatcc ccgcctacat ccgccgcatc      240
tcccactccc acccttccat ttccttccgc caattccctc gcgtcaccaa taaaattacc      300
caaaacatca gcggcaccgc aatcgtggtt gacttcgttc gccagaacga tccccacgtc      360
cgccgtgccc tccaagacat ctccaaatcc gccgtcgtcc gcgccttcat catcgacctc      420
gtctgcacct ccgcgatgac catcagcaag gaattcgaca ttcccacata ctacttctac      480
acttctggtg ccgcagctct gggtgctttt ttgtatttcc ctaagatcca tgaacaaacc      540
acccagagtt tcaaggacct caccgacacc gttatcgaat tcccggacg gaaatctcct      600 ctgaaggcta tacacatgat cgaaccgctg ctcgaccgag cgaccctgc ttattgggac       660 ttcctctcct tttgctccga tcttcccaaa tccaaaggaa tcatcgtcaa cacgttcgaa      720
```

```
gagctcgagc cgccagccgt cctccatgcc attgctgaag gcctgtgtgt tcctgatggg    780
ccaacttcgc ctgtgtacta cgttggacca ttgattgaca agaaaaagt atcgggtaat     840 gatgcagctg cggccgagga ggactgcttg tcatggctcg ataagcagcc aagtcgaagc    900 gtggttttc tctgtttcgg aagcagggga tcactccctg caattcaact gaaggagata    960
gcgaaagcgt tggaggcgag cgggcagagg ttcctgtggg tggtgaagaa gccgccggtt   1020
gatgagaaaa caaagcaggt ccttggagtt gacgactttg atttggaggg tgtgttgcca   1080
gaagggttct tggagaggac caaagacagg gggatggtag tgaagtcatg gcaccgcag    1140 gcagaggtgt tgaagaagga atcggttggt gggttcgtga cacattgcgg atggaactcg   1200
gtgctggaag cagtggttgc gggggtgccc atgattgctt ggccgttgta cgcggagcag   1260
catttgaaca ggaatgttat ggcgacggac atggaaatag cgattgcggt tgagcagaga   1320
gatgaggaag atgggttcgt gagtgggag gaattggaga ggagagtgag ggagttgatg    1380
gagtcggaag aagggagagt gcttagagag aggagcaaga aaattgggga gatggctatg   1440
gctgctttgg gagagaatgg ttcgtccacc agaaacttgg ttaactttgt taatagctta   1500
acataattat gcaagttctg gattttcatt tgcatttgga ttttggtgaa aaataaaata   1560
agaaaaattg tatctgtttg atgacaattg tattgtcttc ccatcaccat tttttttttt   1620
tataataaac tcctcgttct ttatattaaa aaaaaaaaa                          1659
```

<210> SEQ ID NO 15
<211> LENGTH: 1443
<212> TYPE: DNA
<213> ORGANISM: Malus domestica

<400> SEQUENCE: 15

```
atgggagacg taatagtgct gtacgcagct ccaggaatgg ggcatgtcat ctccatggtg    60
gagctgggca agctcatcct ccaccgctac ggccccaca agttttccat caccattctc    120
tacacctgcg gcagcttctt cgacacccct agcatcccg cctacatccg ccgcatctcc    180
cactcccacc cttccatttc cttccgccaa ttccctcgcg tcaccaataa aattacccaa    240
aacatcagcg gcaccgcaat cgtggttgac ttcgttcgcc agaacgatcc ccacgtccgc    300
cgtgccctcc aagacatctc caaatccgcc gtcgtccgcg ccttcatcat cgacctcgtc    360
tgcacctccg cgatgaccat cagcaaggaa ttcgacattc ccacatacta cttctacact    420
tctggtgccg cagctctggg tgcttttttg tatttcccta agatccatga acaaaccacc    480
cagagtttca aggacctcac cgacaccgtt atcgaattcc ccggacggaa atctcctctg    540
aaggctatac acatgatcga accgctgctc gaccgagacg accctgctta ttgggacttc    600
ctctcctttt gctccgatct tcccaaatcc aaggaatca tcgtcaacac gttcgaagag    660
ctcgagccgc cagccgtcct ccatgccatt gctgaaggcc tgtgtgttcc tgatgggcca    720
acttcgcctg tgtactacgt tggaccattg attgacgaag aaaaagtatc gggtaatgat    780
gcagctgcgg ccgaggagga ctgcttgtca tggctcgata agcagccaag tcgaagcgtg    840 gttttctct gtttcggaag caggggatca ctccctgcaa ttcaactgaa ggagatagcg    900 aaagcgttg aggcgagcgg gcagaggttc ctgtgggtgg tgaagaagcc gccggttgat    960
gagaaaacaa agcaggtcct tggagttgac gactttgatt tggagggtgt gttgccagaa   1020
gggttcttgg agaggaccaa agacaggggg atggtagtga agtcatggc accgcaggca    1080 gaggtgttga agaaggaatc ggttggtggg ttcgtgacac attgcggatg gaactcggtg   1140
```

-continued

```
ctggaagcag tggttgcggg ggtgcccatg attgcttggc cgttgtacgc ggagcagcat    1200
ttgaacagga atgttatggc gacggacatg gaaatagcga ttgcggttga gcagagagat    1260
gaggaagatg ggttcgtgag tggggaggaa ttgagagga gagtgaggga gttgatggag     1320
tcggaagaag ggagagtgct tagagagagg agcaagaaaa ttggggagat ggctatggct    1380
gctttgggag agaatggttc gtccaccaga aacttggtta actttgttaa tagcttaaca    1440
taa                                                                 1443
```

<210> SEQ ID NO 16
<211> LENGTH: 39
<212> TYPE: PRT
<213> ORGANISM: Artificial Sequence
<220> FEATURE:
<223> OTHER INFORMATION: Synthetic construct: consensus motif.

<400> SEQUENCE: 16

Val Leu Lys Lys Glu Ser Val Gly Gly Phe Val Thr His Cys Gly Trp
1               5                   10                  15

Asn Ser Val Leu Glu Ala Val Val Ala Gly Val Pro Met Ile Ala Trp
            20                  25                  30

Pro Leu Tyr Ala Glu Gln His
        35

<210> SEQ ID NO 17
<211> LENGTH: 30
<212> TYPE: DNA
<213> ORGANISM: Artificial Sequence
<220> FEATURE:
<223> OTHER INFORMATION: Synthetic construct: primer.

<400> SEQUENCE: 17

```
gactagttct agatcgcgag cggccgccct                                      30
```

<210> SEQ ID NO 18
<211> LENGTH: 25
<212> TYPE: DNA
<213> ORGANISM: Artificial Sequence
<220> FEATURE:
<223> OTHER INFORMATION: Synthetic construct: primer.

<400> SEQUENCE: 18

```
gaagggtgtg ttgccagaag ggtct                                           25
```

<210> SEQ ID NO 19
<211> LENGTH: 20
<212> TYPE: DNA
<213> ORGANISM: Artificial Sequence
<220> FEATURE:
<223> OTHER INFORMATION: Synthetic construct: primer.

<400> SEQUENCE: 19

```
gtcacgaacc caccaaccga                                                 20
```

<210> SEQ ID NO 20
<211> LENGTH: 30
<212> TYPE: DNA
<213> ORGANISM: Artificial Sequence
<220> FEATURE:
<223> OTHER INFORMATION: Synthetic construct: primer.

<400> SEQUENCE: 20

```
acgggatcca tgggagacgt cattgtactg                                      30
```

<210> SEQ ID NO 21
<211> LENGTH: 36
<212> TYPE: DNA
<213> ORGANISM: Artificial Sequence
<220> FEATURE:
<223> OTHER INFORMATION: Synthetic construct: primer.

<400> SEQUENCE: 21
cccaagcttt tatgtaatgc tactaacaaa gttgac                           36

<210> SEQ ID NO 22
<211> LENGTH: 484
<212> TYPE: PRT
<213> ORGANISM: Oryza sativa

<400> SEQUENCE: 22

```
Met Asp Ala Gly Asp Ala Ala Thr Thr Arg Ala Arg Lys Pro Val Val
1               5                   10                  15

Leu Tyr Pro Ser Pro Gly Met Gly Asn Leu Val Ser Met Ile Glu Leu
            20                  25                  30

Gly Lys Val Phe Ala Ala Arg Gly Leu Ala Val Thr Val Val Val
        35                  40                  45

Asp Pro Pro Tyr Gly Asn Thr Gly Ala Thr Gly Pro Phe Leu Ala Gly
    50                  55                  60

Val Thr Ala Ala Asn Pro Ala Met Thr Phe His Arg Leu Pro Lys Val
65                  70                  75                  80

Glu Val Pro Pro Val Ala Ser Lys His His Glu Ser Leu Thr Phe Glu
                85                  90                  95

Val Thr Arg Leu Ser Asn Pro Gly Leu Arg Asp Phe Leu Ala Gly Ala
            100                 105                 110

Ser Pro Val Val Leu Ile Ile Asp Phe Phe Cys Asn Ala Ala Leu Asp
        115                 120                 125

Val Ala Asp Glu Leu Gly Val Pro Ala Tyr Met Phe Tyr Thr Ser Gly
    130                 135                 140

Ala Glu Ile Leu Ala Phe Phe Leu Tyr Leu Pro Val Leu His Ala Gln
145                 150                 155                 160

Thr Thr Ala Asn Phe Gly Glu Met Gly Glu Glu Leu Val His Ala Pro
                165                 170                 175

Gly Ile Pro Ser Phe Pro Ala Thr His Ser Val Leu Pro Leu Met Glu
            180                 185                 190

Arg Asp Asp Pro Ala Tyr Ala Glu Phe Leu Lys Ala Ser Ala Asp Leu
        195                 200                 205

Cys Arg Thr Gln Gly Phe Leu Val Asn Thr Phe Arg Ser Leu Glu Pro
    210                 215                 220

Arg Ala Val Glu Thr Ile Ala Ala Gly Ser Cys Ala Pro Pro Gly Val
225                 230                 235                 240

Ser Thr Pro Pro Val Tyr Cys Ile Gly Pro Leu Ile Lys Ser Ala Glu
                245                 250                 255

Val Gly Glu Asn Arg Ser Glu Glu Cys Leu Ala Trp Leu Asp Thr Gln
            260                 265                 270

Pro Asn Gly Ser Val Val Phe Leu Cys Phe Gly Ser Ile Gly Leu Phe
        275                 280                 285

Ser Ala Glu Gln Ile Lys Glu Val Ala Ala Gly Leu Glu Ala Ser Gly
    290                 295                 300

Gln Arg Phe Leu Trp Val Val Arg Ser Pro Pro Ser Asp Asp Pro Ala
305                 310                 315                 320
```

Lys Lys Phe Asp Lys Pro Pro Glu Pro Asp Leu Asp Ala Leu Leu Pro
            325                 330                 335

Lys Gly Phe Leu Glu Arg Thr Lys Gly Arg Gly Leu Val Val Lys Ser
            340                 345                 350

Trp Ala Pro Gln Arg Asp Val Leu Ala His Ala Val Gly Gly Phe
            355                 360                 365

Val Thr His Cys Gly Trp Asn Ser Val Leu Glu Ser Ile Val Ala Gly
            370                 375                 380

Val Pro Met Leu Ala Trp Pro Leu Tyr Ala Glu Gln Arg Met Asn Arg
385                 390                 395                 400

Val Phe Leu Glu Lys Glu Met Arg Leu Ala Val Ala Val Glu Gly Tyr
            405                 410                 415

Asp Asp Asp Val Gly Glu Gly Thr Val Lys Ala Glu Val Ala Ala
            420                 425                 430

Lys Val Arg Trp Leu Met Glu Ser Asp Gly Gly Arg Ala Leu Leu Glu
            435                 440                 445

Arg Thr Leu Ala Ala Met Arg Arg Ala Lys Ala Ala Leu Arg Asp Gly
            450                 455                 460

Gly Glu Ser Glu Val Thr Leu Ala Arg Leu Val Glu Ser Trp Arg Glu
465                 470                 475                 480

Ala Ala Ser Ala

<210> SEQ ID NO 23
<211> LENGTH: 461
<212> TYPE: PRT
<213> ORGANISM: Stevia rebaudiana

<400> SEQUENCE: 23

Met Glu Ser Ser Lys Val Ile Leu Tyr Pro Ser Pro Gly Ile Gly His
1               5                   10                  15

Leu Val Ser Met Val Glu Leu Gly Lys Leu Ile His Thr His His Pro
            20                  25                  30

Ser Leu Ser Val Ile Ile Leu Val Leu Pro Ala Thr Tyr Glu Thr Gly
            35                  40                  45

Ser Thr Thr Thr Tyr Ile Asn Thr Val Ser Thr Thr Thr Pro Phe Ile
        50                  55                  60

Thr Phe His His Leu Pro Val Ile Pro Leu Pro Pro Asp Ser Ser Ser
65                  70                  75                  80

Glu Phe Ile Asp Leu Ala Phe Asp Ile Pro Gln Leu Tyr Asn Pro Val
                85                  90                  95

Val Tyr Asn Thr Leu Val Ala Ile Ser Glu Thr Ser Thr Ile Lys Ala
            100                 105                 110

Val Ile Leu Asp Phe Phe Val Asn Ala Ala Phe Gln Ile Ser Lys Ser
        115                 120                 125

Leu Asp Leu Pro Thr Tyr Tyr Phe Phe Thr Ser Gly Ala Ser Gly Leu
    130                 135                 140

Cys Ala Phe Leu His Leu Pro Thr Ile Tyr Lys Thr Tyr Ser Gly Asn
145                 150                 155                 160

Phe Lys Asp Leu Asp Thr Phe Ile Asn Ile Pro Gly Val Pro Pro Ile
                165                 170                 175

His Ser Ser Asp Met Pro Thr Val Leu Phe Asp Lys Glu Ser Asn Ser
            180                 185                 190

Tyr Lys Asn Phe Val Lys Thr Ser Asn Asn Met Ala Lys Ser Ser Gly
        195                 200                 205

Val Ile Ala Asn Ser Phe Leu Gln Leu Glu Glu Arg Ala Ala Gln Thr
210                 215                 220

Leu Arg Asp Gly Lys Ser Ile Thr Asp Gly Pro Ser Pro Ile Tyr
225                 230                 235                 240

Leu Ile Gly Pro Leu Ile Ala Ser Gly Asn Gln Val Asp His Asn Glu
            245                 250                 255

Asn Glu Cys Leu Lys Trp Leu Asn Thr Gln Pro Ser Lys Ser Val Val
            260                 265                 270

Phe Leu Cys Phe Gly Ser Gln Gly Val Phe Lys Lys Glu Gln Leu Lys
            275                 280                 285

Glu Ile Ala Val Gly Leu Glu Arg Ser Gly Gln Arg Phe Leu Trp Val
290                 295                 300

Val Arg Lys Pro Pro Ser Asp Gly Gly Lys Glu Phe Gly Leu Asp Asp
305                 310                 315                 320

Val Leu Pro Glu Gly Phe Val Ala Arg Thr Lys Glu Lys Gly Leu Val
                325                 330                 335

Val Lys Asn Trp Ala Pro Gln Pro Ala Ile Leu Gly His Glu Ser Val
                340                 345                 350

Gly Gly Phe Val Ser His Cys Gly Trp Asn Ser Ser Leu Glu Ala Val
            355                 360                 365

Val Phe Gly Val Pro Met Val Ala Trp Pro Leu Tyr Ala Glu Gln Lys
370                 375                 380

Met Asn Arg Val Tyr Leu Val Glu Glu Ile Lys Val Ala Leu Trp Leu
385                 390                 395                 400

Arg Met Ser Ala Asp Gly Phe Val Ser Ala Glu Ala Val Glu Glu Thr
                405                 410                 415

Val Arg Gln Leu Met Asp Gly Arg Arg Val Arg Glu Arg Ile Leu Glu
                420                 425                 430

Met Ser Thr Lys Ala Lys Ala Ala Val Glu Asp Gly Gly Ser Ser Arg
            435                 440                 445

Val Asp Phe Phe Lys Leu Thr Glu Ser Trp Thr His Lys
450                 455                 460

<210> SEQ ID NO 24
<211> LENGTH: 462
<212> TYPE: PRT
<213> ORGANISM: Arabidopsis thaliana

<400> SEQUENCE: 24

Met Gly Glu Glu Ala Ile Val Leu Tyr Pro Ala Pro Ile Gly His
1               5                   10                  15

Leu Val Ser Met Val Glu Leu Gly Lys Thr Ile Leu Ser Lys Asn Pro
            20                  25                  30

Ser Leu Ser Ile His Ile Ile Leu Val Pro Pro Tyr Gln Pro Glu
        35                  40                  45

Ser Thr Ala Thr Tyr Ile Ser Val Ser Ser Phe Pro Ser Ile
50                  55                  60

Thr Phe His His Leu Pro Ala Val Thr Pro Tyr Ser Ser Ser Phe Thr
65                  70                  75                  80

Ser Arg His His His Glu Ser Leu Leu Leu Glu Ile Leu Cys Phe Ser
                85                  90                  95

Asn Pro Ser Val His Arg Thr Leu Phe Ser Leu Ser Arg Asn Phe Asn
            100                 105                 110

Val Arg Ala Met Ile Ile Asp Phe Phe Cys Thr Ala Val Leu Asp Ile

```
            115                 120                 125
Thr Ala Asp Phe Thr Phe Pro Val Tyr Tyr Phe Phe Thr Ser Gly Ala
    130                 135                 140
Ala Cys Leu Ala Phe Ser Phe Tyr Leu Pro Thr Ile His Glu Thr Thr
145                 150                 155                 160
Pro Gly Lys Asn Leu Lys Asp Ile Pro Thr Leu Asn Ile Pro Gly Val
                165                 170                 175
Pro Pro Met Lys Gly Ser Asp Met Pro Lys Ala Val Leu Glu Arg Asp
            180                 185                 190
Asp Glu Val Tyr Asp Val Phe Ile Met Phe Gly Lys Gln Leu Pro Lys
        195                 200                 205
Ser Ser Gly Ile Ile Ile Asn Thr Phe Asp Ala Leu Glu Asn Arg Ala
    210                 215                 220
Ile Lys Ala Ile Thr Glu Glu Leu Cys Phe Arg Asn Ile Tyr Pro Ile
225                 230                 235                 240
Gly Pro Leu Ile Val Asn Gly Arg Thr Asp Asp Lys Asn Asp Asn Lys
                245                 250                 255
Thr Val Ser Cys Leu Asp Trp Leu Asp Ser Gln Pro Glu Lys Ser Val
            260                 265                 270
Val Phe Leu Cys Phe Gly Ser Leu Gly Leu Phe Ser Lys Glu Gln Leu
        275                 280                 285
Ile Glu Ile Ala Val Gly Leu Glu Lys Ser Gly Gln Arg Phe Leu Trp
    290                 295                 300
Val Val Arg Asn Pro Pro Glu Leu Glu Lys Ser Glu Leu Asp Leu Lys
305                 310                 315                 320
Ser Leu Leu Pro Glu Gly Phe Leu Ser Arg Thr Glu Asn Arg Gly Met
                325                 330                 335
Val Val Glu Ser Trp Ala Pro Gln Val Pro Val Leu Asn His Lys Ala
            340                 345                 350
Val Gly Gly Phe Val Thr His Cys Gly Trp Asn Ser Ile Leu Glu Ala
        355                 360                 365
Val Cys Ala Gly Val Pro Met Val Ala Trp Pro Leu Tyr Ala Glu Gln
    370                 375                 380
Arg Phe Asn Arg Val Met Ile Val Asp Glu Ile Lys Ile Ala Ile Ser
385                 390                 395                 400
Met Asn Glu Ser Glu Thr Gly Phe Val Ser Ser Thr Glu Val Glu Lys
                405                 410                 415
Arg Val Gln Glu Ile Ile Gly Glu Cys Pro Val Arg Glu Arg Thr Met
            420                 425                 430
Ala Met Lys Asn Ala Ala Glu Leu Ala Leu Thr Glu Thr Gly Ser Ser
        435                 440                 445
His Thr Ala Leu Thr Thr Leu Leu Gln Ser Trp Ser Pro Lys
    450                 455                 460

<210> SEQ ID NO 25
<211> LENGTH: 392
<212> TYPE: PRT
<213> ORGANISM: Vigna mungo

<400> SEQUENCE: 25

Phe Ala Arg Ala Gln Ile Ser Lys Thr Ala Ile Val Lys Ala Phe Val
1               5                   10                  15
Ile Asp Leu Phe Cys Ala Ser Thr Met Glu Ser Ala Ser Ser Met Gly
            20                  25                  30
```

Ile Pro Val Tyr Phe Phe Thr Ser Gly Ala Ala Ile Leu Ala Leu
                35                  40                  45

Tyr Ser Tyr Phe Pro Lys Leu His Gln Glu Cys Ile Val Ser Phe Lys
 50                  55                  60

Asn Met Val Gly Val Glu Leu Arg Val Pro Gly Asn Ala Thr Leu Lys
 65                  70                  75                  80

Ala Arg Gly Thr Ala Gly Thr His Leu Gly Gln Ala Arg Pro Cys Val
                 85                  90                  95

Leu Gly His Ala Pro Pro Glu Ala Arg Gly Val Ile Val Asn Ser Phe
            100                 105                 110

Glu Glu Leu Glu Pro Ala Ala Val Asn Ala Val Thr Gln Gly Ala Cys
        115                 120                 125

Phe Pro Asp Ala Thr His Val Pro Arg Val Tyr Tyr Ile Gly Pro Leu
    130                 135                 140

Ile Ala Glu Ser Gln Gln Ser Asp Ala Glu Gly Arg Glu Ser Lys Glu
145                 150                 155                 160

Cys Leu Arg Trp Leu Glu Glu Gln Pro Ser Arg Ser Val Val Tyr Leu
                165                 170                 175

Cys Phe Gly Ser Arg Gly Ser Phe Ser Val Ser Gln Leu Lys Glu Ile
            180                 185                 190

Ala Lys Gly Leu Glu Lys Ser Gly Lys Arg Phe Leu Trp Val Val Lys
        195                 200                 205

Arg Pro Leu Glu Glu Glu Gly Ala Lys His Glu Glu Ala Ala Lys Pro
    210                 215                 220

Gly Asp Glu Phe Asp Leu Ala Ser Met Leu Pro Asp Gly Phe Leu Glu
225                 230                 235                 240

Arg Thr Lys Asp Arg Gly Met Val Val Lys Ala Trp Ala Pro Gln Val
                245                 250                 255

Glu Val Leu Ser Arg Glu Ser Val Gly Gly Phe Val Ser His Cys Gly
            260                 265                 270

Trp Asn Ser Val Leu Glu Gly Val Ala Gly Val Pro Met Val Ala
        275                 280                 285

Trp Pro Leu Tyr Ala Glu Gln His Val Asn Arg Glu Val Met Val Ala
    290                 295                 300

Trp Pro Leu Tyr Ala Glu Gln His Val Asn Arg Glu Val Met Val Gly
305                 310                 315                 320

Glu Met Lys Val Ala Gly Val Asn Glu Arg Val Glu Asp Gly Phe
                325                 330                 335

Val Ser Ala Glu Glu Val Glu Lys Arg Val Arg Glu Val Met Glu Thr
            340                 345                 350

Lys Glu Ile Arg Gly Arg Ser Phe Lys Leu Lys Gln Met Ala Met Ala
        355                 360                 365

Ala Val Ala Glu Phe Gly Ser Ser Thr Thr Ala Ile Ala His Leu Leu
    370                 375                 380

His Ser Trp Thr Ser Phe Thr Ser
385                 390

<210> SEQ ID NO 26
<211> LENGTH: 483
<212> TYPE: PRT
<213> ORGANISM: Artificial Sequence
<220> FEATURE:
<223> OTHER INFORMATION: Synthetic construct: consensus sequence.
<220> FEATURE:
<221> NAME/KEY: MISC_FEATURE
<222> LOCATION: (1)..(482)

-continued

```
<223> OTHER INFORMATION: Where X is shown, the amino acid is not
      specified; but refer to Fig. 9 for relevant information as to
      sequences from which the consensus was designed.
<220> FEATURE:
<221> NAME/KEY: MISC_FEATURE
<222> LOCATION: (10)..(10)
<223> OTHER INFORMATION: X is A,S (ala,ser)
<220> FEATURE:
<221> NAME/KEY: MISC_FEATURE
<222> LOCATION: (16)..(16)
<223> OTHER INFORMATION: X is I,V (ile,val)
<220> FEATURE:
<221> NAME/KEY: MISC_FEATURE
<222> LOCATION: (17)..(17)
<223> OTHER INFORMATION: X is I,V (ile,val)
<220> FEATURE:
<221> NAME/KEY: MISC_FEATURE
<222> LOCATION: (18)..(18)
<223> OTHER INFORMATION: X is A,S (ala,ser)
<220> FEATURE:
<221> NAME/KEY: MISC_FEATURE
<222> LOCATION: (25)..(25)
<223> OTHER INFORMATION: X is F,L (phe,leu)
<220> FEATURE:
<221> NAME/KEY: MISC_FEATURE
<222> LOCATION: (27)..(27)
<223> OTHER INFORMATION: X is L,V (leu,val)
<220> FEATURE:
<221> NAME/KEY: MISC_FEATURE
<222> LOCATION: (46)..(46)
<223> OTHER INFORMATION: X is F,I (phe,ile)
<220> FEATURE:
<221> NAME/KEY: MISC_FEATURE
<222> LOCATION: (47)..(47)
<223> OTHER INFORMATION: X is F,V (phe,val)
<220> FEATURE:
<221> NAME/KEY: MISC_FEATURE
<222> LOCATION: (50)..(50)
<223> OTHER INFORMATION: X is A,P (ala,pro)
<220> FEATURE:
<221> NAME/KEY: MISC_FEATURE
<222> LOCATION: (54)..(54)
<223> OTHER INFORMATION: X is A,V (ala,val)
<220> FEATURE:
<221> NAME/KEY: MISC_FEATURE
<222> LOCATION: (65)..(65)
<223> OTHER INFORMATION: X is F,S (phe,ser)
<220> FEATURE:
<221> NAME/KEY: MISC_FEATURE
<222> LOCATION: (77)..(77)
<223> OTHER INFORMATION: X is K,N (lys,asn)
<220> FEATURE:
<221> NAME/KEY: MISC_FEATURE
<222> LOCATION: (80)..(80)
<223> OTHER INFORMATION: X is R,Q (arg,gln)
<220> FEATURE:
<221> NAME/KEY: MISC_FEATURE
<222> LOCATION: (84)..(84)
<223> OTHER INFORMATION: X is V,G (val,gly)
<220> FEATURE:
<221> NAME/KEY: MISC_FEATURE
<222> LOCATION: (85)..(85)
<223> OTHER INFORMATION: X is P,T (pro,thr)
<220> FEATURE:
<221> NAME/KEY: MISC_FEATURE
<222> LOCATION: (88)..(88)
<223> OTHER INFORMATION: X is T,V (thr,val)
<220> FEATURE:
<221> NAME/KEY: MISC_FEATURE
<222> LOCATION: (89)..(89)
<223> OTHER INFORMATION: X is F,V (phe,val)
<220> FEATURE:
<221> NAME/KEY: MISC_FEATURE
<222> LOCATION: (92)..(92)
<223> OTHER INFORMATION: X is I,V (ile,val)
<220> FEATURE:
<221> NAME/KEY: MISC_FEATURE
<222> LOCATION: (101)..(101)
<223> OTHER INFORMATION: X is S,R (ser,arg)
```

```
<220> FEATURE:
<221> NAME/KEY: MISC_FEATURE
<222> LOCATION: (105)..(105)
<223> OTHER INFORMATION: X is E,D (glu,asp)
<220> FEATURE:
<221> NAME/KEY: MISC_FEATURE
<222> LOCATION: (111)..(111)
<223> OTHER INFORMATION: X is T,V (thr,val)
<220> FEATURE:
<221> NAME/KEY: MISC_FEATURE
<222> LOCATION: (120)..(120)
<223> OTHER INFORMATION: X is F,V (phe,val)
<220> FEATURE:
<221> NAME/KEY: MISC_FEATURE
<222> LOCATION: (125)..(125)
<223> OTHER INFORMATION: X is L,M (leu,met)
<220> FEATURE:
<221> NAME/KEY: MISC_FEATURE
<222> LOCATION: (126)..(126)
<223> OTHER INFORMATION: X is P,T (pro,thr)
<220> FEATURE:
<221> NAME/KEY: MISC_FEATURE
<222> LOCATION: (128)..(128)
<223> OTHER INFORMATION: X is G,S (gly,ser)
<220> FEATURE:
<221> NAME/KEY: MISC_FEATURE
<222> LOCATION: (132)..(132)
<223> OTHER INFORMATION: X is N,D (asn,asp)
<220> FEATURE:
<221> NAME/KEY: MISC_FEATURE
<222> LOCATION: (139)..(139)
<223> OTHER INFORMATION: X is C,Y (cys,tyr)
<220> FEATURE:
<221> NAME/KEY: MISC_FEATURE
<222> LOCATION: (145)..(145)
<223> OTHER INFORMATION: X is I,A (ile,ala)
<220> FEATURE:
<221> NAME/KEY: MISC_FEATURE
<222> LOCATION: (147)..(147)
<223> OTHER INFORMATION: X is A,G (ala,gly)
<220> FEATURE:
<221> NAME/KEY: MISC_FEATURE
<222> LOCATION: (152)..(152)
<223> OTHER INFORMATION: X is L,F (leu,phe)
<220> FEATURE:
<221> NAME/KEY: MISC_FEATURE
<222> LOCATION: (156)..(156)
<223> OTHER INFORMATION: X is D,H (asp,his)
<220> FEATURE:
<221> NAME/KEY: MISC_FEATURE
<222> LOCATION: (160)..(160)
<223> OTHER INFORMATION: X is K (lys)
<220> FEATURE:
<221> NAME/KEY: MISC_FEATURE
<222> LOCATION: (161)..(161)
<223> OTHER INFORMATION: X is T (thr)
<220> FEATURE:
<221> NAME/KEY: MISC_FEATURE
<222> LOCATION: (163)..(163)
<223> OTHER INFORMATION: X is E,Q (glu,gln)
<220> FEATURE:
<221> NAME/KEY: MISC_FEATURE
<222> LOCATION: (169)..(169)
<223> OTHER INFORMATION: X is R,T (arg,thr)
<220> FEATURE:
<221> NAME/KEY: MISC_FEATURE
<222> LOCATION: (173)..(173)
<223> OTHER INFORMATION: X is F,I (phe,ile)
<220> FEATURE:
<221> NAME/KEY: MISC_FEATURE
<222> LOCATION: (178)..(178)
<223> OTHER INFORMATION: X is W,R (trp,arg)
<220> FEATURE:
<221> NAME/KEY: MISC_FEATURE
<222> LOCATION: (185)..(185)
<223> OTHER INFORMATION: X is T,P,I (thr,pro,ile)
<220> FEATURE:
<221> NAME/KEY: MISC_FEATURE
<222> LOCATION: (188)..(188)
```

```
<223> OTHER INFORMATION: X is V,I (val,ile)
<220> FEATURE:
<221> NAME/KEY: MISC_FEATURE
<222> LOCATION: (189)..(189)
<223> OTHER INFORMATION: X is Q,E (gln,glu)
<220> FEATURE:
<221> NAME/KEY: MISC_FEATURE
<222> LOCATION: (190)..(190)
<223> OTHER INFORMATION: X is L,P (leu,pro)
<220> FEATURE:
<221> NAME/KEY: MISC_FEATURE
<222> LOCATION: (191)..(191)
<223> OTHER INFORMATION: X is V,L (val,leu)
<220> FEATURE:
<221> NAME/KEY: MISC_FEATURE
<222> LOCATION: (195)..(195)
<223> OTHER INFORMATION: X is N,D (asn,asp)
<220> FEATURE:
<221> NAME/KEY: MISC_FEATURE
<222> LOCATION: (200)..(200)
<223> OTHER INFORMATION: X is S,W (ser,trp)
<220> FEATURE:
<221> NAME/KEY: MISC_FEATURE
<222> LOCATION: (202)..(202)
<223> OTHER INFORMATION: X is M,F (met,phe)
<220> FEATURE:
<221> NAME/KEY: MISC_FEATURE
<222> LOCATION: (203)..(203)
<223> OTHER INFORMATION: X is I,L (ile,leu)
<220> FEATURE:
<221> NAME/KEY: MISC_FEATURE
<222> LOCATION: (204)..(204)
<223> OTHER INFORMATION: X is Y,S (tyr,ser)
<220> FEATURE:
<221> NAME/KEY: MISC_FEATURE
<222> LOCATION: (208)..(208)
<223> OTHER INFORMATION: X is H,D (his,asp)
<220> FEATURE:
<221> NAME/KEY: MISC_FEATURE
<222> LOCATION: (213)..(213)
<223> OTHER INFORMATION: X is N,K (asn,lys)
<220> FEATURE:
<221> NAME/KEY: MISC_FEATURE
<222> LOCATION: (227)..(227)
<223> OTHER INFORMATION: X is S,A (ser,ala)
<220> FEATURE:
<221> NAME/KEY: MISC_FEATURE
<222> LOCATION: (230)..(230)
<223> OTHER INFORMATION: X is Q,H (gln,his)
<220> FEATURE:
<221> NAME/KEY: MISC_FEATURE
<222> LOCATION: (234)..(234)
<223> OTHER INFORMATION: X is G,E (gly,glu)
<220> FEATURE:
<221> NAME/KEY: MISC_FEATURE
<222> LOCATION: (244)..(244)
<223> OTHER INFORMATION: X is P,S (pro,ser)
<220> FEATURE:
<221> NAME/KEY: MISC_FEATURE
<222> LOCATION: (254)..(254)
<223> OTHER INFORMATION: X is E,D (glu,asp)
<220> FEATURE:
<221> NAME/KEY: MISC_FEATURE
<222> LOCATION: (258)..(258)
<223> OTHER INFORMATION: X is E,V (glu,val)
<220> FEATURE:
<221> NAME/KEY: MISC_FEATURE
<222> LOCATION: (259)..(259)
<223> OTHER INFORMATION: X is L,S (leu,ser)
<220> FEATURE:
<221> NAME/KEY: MISC_FEATURE
<222> LOCATION: (260)..(260)
<223> OTHER INFORMATION: X is S,G (ser,gly)
<220> FEATURE:
<221> NAME/KEY: MISC_FEATURE
<222> LOCATION: (261)..(261)
<223> OTHER INFORMATION: X is K,N (lys,asn)
<220> FEATURE:
<221> NAME/KEY: MISC_FEATURE
```

```
<222> LOCATION: (264)..(264)
<223> OTHER INFORMATION: X is D,A (asp,ala)
<220> FEATURE:
<221> NAME/KEY: MISC_FEATURE
<222> LOCATION: (267)..(267)
<223> OTHER INFORMATION: X is E,G (glu,gly)
<220> FEATURE:
<221> NAME/KEY: MISC_FEATURE
<222> LOCATION: (268)..(268)
<223> OTHER INFORMATION: X is K,E (lys,glu)
<220> FEATURE:
<221> NAME/KEY: MISC_FEATURE
<222> LOCATION: (269)..(269)
<223> OTHER INFORMATION: X is E,D (glu,asp)
<220> FEATURE:
<221> NAME/KEY: MISC_FEATURE
<222> LOCATION: (270)..(270)
<223> OTHER INFORMATION: X is D (asp)
<220> FEATURE:
<221> NAME/KEY: MISC_FEATURE
<222> LOCATION: (284)..(284)
<223> OTHER INFORMATION: X is L,V (leu,val)
<220> FEATURE:
<221> NAME/KEY: MISC_FEATURE
<222> LOCATION: (291)..(291)
<223> OTHER INFORMATION: X is M,R (met,arg)
<220> FEATURE:
<221> NAME/KEY: MISC_FEATURE
<222> LOCATION: (294)..(294)
<223> OTHER INFORMATION: X is F,L (phe,leu)
<220> FEATURE:
<221> NAME/KEY: MISC_FEATURE
<222> LOCATION: (297)..(297)
<223> OTHER INFORMATION: X is A,I (ala,ile)
<220> FEATURE:
<221> NAME/KEY: MISC_FEATURE
<222> LOCATION: (304)..(304)
<223> OTHER INFORMATION: X is N,K (asn,lys)
<220> FEATURE:
<221> NAME/KEY: MISC_FEATURE
<222> LOCATION: (305)..(305)
<223> OTHER INFORMATION: X is G,A (gly,ala)
<220> FEATURE:
<221> NAME/KEY: MISC_FEATURE
<222> LOCATION: (323)..(323)
<223> OTHER INFORMATION: X is E,D (glu,asp)
<220> FEATURE:
<221> NAME/KEY: MISC_FEATURE
<222> LOCATION: (326)..(326)
<223> OTHER INFORMATION: X is S,T (ser,thr)
<220> FEATURE:
<221> NAME/KEY: MISC_FEATURE
<222> LOCATION: (330)..(330)
<223> OTHER INFORMATION: X is H,L (his,leu)
<220> FEATURE:
<221> NAME/KEY: MISC_FEATURE
<222> LOCATION: (338)..(338)
<223> OTHER INFORMATION: X is K,E (lys,glu)
<220> FEATURE:
<221> NAME/KEY: MISC_FEATURE
<222> LOCATION: (350)..(350)
<223> OTHER INFORMATION: X is A,K (ala,lys)
<220> FEATURE:
<221> NAME/KEY: MISC_FEATURE
<222> LOCATION: (363)..(363)
<223> OTHER INFORMATION: X is V,A (val,ala)
<220> FEATURE:
<221> NAME/KEY: MISC_FEATURE
<222> LOCATION: (364)..(364)
<223> OTHER INFORMATION: X is V,E (val,glu)
<220> FEATURE:
<221> NAME/KEY: MISC_FEATURE
<222> LOCATION: (404)..(404)
<223> OTHER INFORMATION: X is M,L (met,leu)
<220> FEATURE:
<221> NAME/KEY: MISC_FEATURE
<222> LOCATION: (409)..(409)
<223> OTHER INFORMATION: X is L,M (leu,met)
<220> FEATURE:
```

```
<221> NAME/KEY: MISC_FEATURE
<222> LOCATION: (410)..(410)
<223> OTHER INFORMATION: X is V,A (val,ala)
<220> FEATURE:
<221> NAME/KEY: MISC_FEATURE
<222> LOCATION: (415)..(415)
<223> OTHER INFORMATION: X is I,L (ile,leu)
<220> FEATURE:
<221> NAME/KEY: MISC_FEATURE
<222> LOCATION: (418)..(418)
<223> OTHER INFORMATION: X is A,G (ala,gly)
<220> FEATURE:
<221> NAME/KEY: MISC_FEATURE
<222> LOCATION: (426)..(426)
<223> OTHER INFORMATION: X is G,D (gly,asp)
<220> FEATURE:
<221> NAME/KEY: MISC_FEATURE
<222> LOCATION: (434)..(434)
<223> OTHER INFORMATION: X is V,L (val,leu)
<220> FEATURE:
<221> NAME/KEY: MISC_FEATURE
<222> LOCATION: (446)..(446)
<223> OTHER INFORMATION: X is G,E (gly,glu)
<220> FEATURE:
<221> NAME/KEY: MISC_FEATURE
<222> LOCATION: (449)..(449)
<223> OTHER INFORMATION: X is V,A (val,ala)
<220> FEATURE:
<221> NAME/KEY: MISC_FEATURE
<222> LOCATION: (454)..(454)
<223> OTHER INFORMATION: X is C,S (cys,ser)
<220> FEATURE:
<221> NAME/KEY: MISC_FEATURE
<222> LOCATION: (457)..(457)
<223> OTHER INFORMATION: X is L,I (leu,ile)
<220> FEATURE:
<221> NAME/KEY: MISC_FEATURE
<222> LOCATION: (462)..(462)
<223> OTHER INFORMATION: X is S,M (ser,met)
<220> FEATURE:
<221> NAME/KEY: MISC_FEATURE
<222> LOCATION: (468)..(468)
<223> OTHER INFORMATION: X is T,N (thr,asn)
<220> FEATURE:
<221> NAME/KEY: MISC_FEATURE
<222> LOCATION: (480)..(480)
<223> OTHER INFORMATION: X is S,N (ser,asn)
<220> FEATURE:
<221> NAME/KEY: MISC_FEATURE
<222> LOCATION: (482)..(482)
<223> OTHER INFORMATION: X is I,L (ile,leu)

<400> SEQUENCE: 26

Met Gly Asp Val Ile Val Leu Tyr Ala Xaa Pro Gly Met Gly His Xaa
1               5                   10                  15

Xaa Xaa Met Val Glu Leu Gly Lys Xaa Ile Xaa His Arg Tyr Gly Pro
            20                  25                  30

His Lys Phe Ser Ile Thr Ile Leu Tyr Thr Cys Gly Ser Xaa Xaa Asp
        35                  40                  45

Thr Xaa Ser Ile Pro Xaa Tyr Ile Arg Arg Ile Ser His Ser His Pro
    50                  55                  60

Xaa Ile Ser Phe Arg Gln Phe Pro Arg Val Thr Asn Xaa Ile Thr Xaa
65                  70                  75                  80

Asn Ile Ser Xaa Xaa Ala Ile Xaa Xaa Asp Phe Xaa Arg Gln Asn Asp
                85                  90                  95

Pro His Val Arg Xaa Ala Leu Gln Xaa Ile Ser Lys Ser Ala Xaa Val
            100                 105                 110

Arg Ala Phe Ile Ile Asp Leu Xaa Cys Thr Ser Ala Xaa Xaa Ile Xaa
        115                 120                 125

Lys Glu Phe Xaa Ile Pro Thr Tyr Tyr Phe Xaa Thr Ser Gly Ala Ala
```

-continued

```
    130                 135                 140

Xaa Leu Xaa Ala Phe Leu Tyr Xaa Pro Lys Ile Xaa Glu Gln Thr Xaa
145                 150                 155                 160

Xaa Thr Xaa Ser Phe Lys Asp Leu Xaa Asp Thr Val Xaa Glu Phe Pro
                165                 170                 175

Gly Xaa Lys Ser Pro Leu Lys Ala Xaa His Met Xaa Xaa Xaa Xaa Leu
            180                 185                 190

Asp Arg Xaa Asp Pro Ala Tyr Xaa Asp Xaa Xaa Xaa Phe Cys Ser Xaa
        195                 200                 205

Leu Pro Lys Ser Xaa Gly Ile Ile Val Asn Thr Phe Glu Glu Leu Glu
    210                 215                 220

Pro Pro Xaa Val Leu Xaa Ala Ile Ala Xaa Gly Leu Cys Val Pro Asp
225                 230                 235                 240

Gly Pro Thr Xaa Pro Val Tyr Tyr Val Gly Pro Leu Ile Xaa Glu Glu
                245                 250                 255

Lys Xaa Xaa Xaa Xaa Asp Ala Xaa Ala Ala Xaa Xaa Xaa Xaa Cys Leu
            260                 265                 270

Ser Trp Leu Asp Lys Gln Pro Ser Arg Ser Val Xaa Phe Leu Cys Phe
        275                 280                 285

Gly Ser Xaa Gly Ser Xaa Pro Ala Xaa Gln Leu Lys Glu Ile Ala Xaa
    290                 295                 300

Xaa Leu Glu Ala Ser Gly Gln Arg Phe Leu Trp Val Val Lys Lys Pro
305                 310                 315                 320

Pro Val Xaa Glu Lys Xaa Lys Gln Val Xaa Gly Val Asp Asp Phe Asp
                325                 330                 335

Leu Xaa Gly Val Leu Pro Glu Gly Phe Leu Glu Arg Thr Xaa Asp Arg
            340                 345                 350

Gly Met Val Val Lys Ser Trp Ala Pro Gln Xaa Xaa Val Leu Lys Lys
        355                 360                 365

Glu Ser Val Gly Gly Phe Val Thr His Cys Gly Trp Asn Ser Val Leu
    370                 375                 380

Glu Ala Val Val Ala Gly Val Pro Met Ile Ala Trp Pro Leu Tyr Ala
385                 390                 395                 400

Glu Gln His Xaa Asn Arg Asn Val Xaa Xaa Thr Asp Met Glu Xaa Ala
                405                 410                 415

Ile Xaa Val Glu Gln Arg Asp Glu Glu Xaa Gly Phe Val Ser Gly Glu
            420                 425                 430

Glu Xaa Glu Arg Arg Val Arg Glu Leu Met Glu Ser Glu Xaa Gly Arg
        435                 440                 445

Xaa Leu Arg Glu Arg Xaa Lys Lys Xaa Gly Glu Met Ala Xaa Ala Ala
    450                 455                 460

Leu Gly Glu Ser Gly Ser Ser Thr Arg Asn Leu Val Asn Phe Val Xaa
465                 470                 475                 480

Ser Xaa Thr
```

PHLORETIN GLYCOSYLTRANSFERASES, POLYNUCLEOTIDES ENCODING THESE AND METHODS OF USE

CROSS-REFERENCE TO RELATED APPLICATIONS

This application is a Continuation of International Application No. PCT/NZ2008/000341, filed Dec. 19, 2008, which claims the benefit of New Zealand Patent Application No. 564691, filed Dec. 21, 2007, which is hereby incorporated by reference to the extent there is no inconsistency with the present disclosure.

TECHNICAL FIELD

The present invention relates to compositions and methods for producing plants with altered phloretin glycosyltransferase activity and/or altered phlorizin content.

BACKGROUND ART

The dihydrochalcone phlorizin (phloretin 2'-glucoside, see FIG. 1) is the major phenolic glucoside found in apple trees. Phlorizin has a bitter taste that contributes to the characteristic flavour of cider (Whiting and Coggins 1975), and its dimerised oxidation products contribute to the colour of apple juices (Ridgway and Tucker 1997). However, since it was isolated from the bark of the apple tree in 1835 (Petersen 1835), phlorizin has attracted most scientific interest through its use as a pharmaceutical and tool for physiology research. Its principal pharmacological action is to produce renal glycosuria and block glucose transportation by inhibition of the sodium-linked glucose transporters (reviewed in Ehrenkranz et al. 2005). Phlorizin and its derivatives have also been shown to be an extremely effective antioxidants in vitro (Ridgway et al. 1996), and to have a range of bioactive functions such as inhibition of lipid peroxidation (Ridgway et al. 1997; Rezk et al. 2002), prevention of bone loss (Puel et al. 2005), enhancement of memory (Boccia et al. 1999), and inhibition of cancer cell growth (Veeriah et al. 2006).

Until recently phlorizin was believed to exist only in Malus species. However phloretin glycosides have been reported in the leaves of Australian native sarsaparilla (Smilax glyciphylla, Cox et al. 2005), sweet tea (Lithocarpus polystachyus, Dong et al. 2007) and at very low levels in strawberry fruit (Hilt et al. 2003). In apple trees, phlorizin is found primarily in the young shoots, roots, leaves and bark. In fruit, phlorizin is most abundant in the seeds, with intermediate levels in both the core and the skin, and the lowest level in the cortex. Variation has been assessed within apple trees, between orchards, between different cultivars and among mutants (Hunter and Hull 1993, Awad et al. 2000). Despite this information, little is known of the in planta function of phlorizin in apple tree physiology, although it has been suggested that it might act in apple tree growth and development (Zhang et al. 2007) or be an inhibitor of bacterial (MacDonald and Bishop 1952) or fungal growth (Gessler et al. 2006).

The molecular basis for production of phlorizin in planta has not been described. Phloretin is a product of the phenylpropanoid pathway (Watts et al. 2004), with conversion to its glucoside, phlorizin, likely to be catalysed by the action of a uridine diphosphate (UDP) glycosyltransferase (UGT). UGTs mediate the transfer of a sugar residue from an activated nucleotide sugar to acceptor molecules (aglycones). Plants contain large families of UGTs with over 100 genes being described in Arabidopsis. These genes have a common signature motif of 44 amino acids thought to be involved in binding of the UDP moiety of the activated sugar (Li et al. 2001). A phylogenetic analysis established the presence of distinct Groups (A-N) and Families (UGT71-92) of UGT genes in Arabidopsis (Ross et al. 2001) and this facilitated the characterisation of many new activities (Jackson et al. 2001; Lim et al. 2002; Jones et al. 2003; Messner et al. 2003; Lim et al. 2004; Lim et al. 2005). Although initially thought to be promiscuous enzymes, recent evidence suggests that their broad substrate specificity is limited by regio-specificity (Hansen et al. 2003; Lim et al. 2003), and in some cases UGTS have been shown to be highly specific (Fukuchi-Mizutani et al. 2003). Using a functional genomics approach we have identified and characterised a UGT from apple belonging to the previously uncharacterised UGT Family 88. We establish that MpUGT88A1 mediates the glycosylation of the dihydrochalcone phloretin to phlorizin which may indicate that other members of UGT Family 88 utilise similar substrates.

It would be beneficial to have a means to increase phlorizin levels in plants.

It is an object of the invention to provide improved compositions and methods for modulating activity and/or phlorizin content in plants or at least to provide the public with a useful choice.

SUMMARY OF THE INVENTION

In a first aspect the invention provides a method for producing a plant cell or plant with increased phlorizin content, the method comprising transformation of a plant cell or plant with a polynucleotide encoding a polypeptide with the amino acid sequence of any one of SEQ ID NO: 1 to 5 or a variant of the polypeptide.

Preferably the variant has phloretin glycosyltransferase activity.

In a further aspect the invention provides a method for producing a plant cell or plant with increased phloretin glycosyltransferase activity, the method comprising transformation of a plant cell or plant with a polynucleotide encoding a polypeptide with the amino acid sequence of any one of SEQ ID NO: 1 to 5, or a variant of the polypeptide.

Preferably the variant has the activity of phloretin glycosyltransferase activity.

Preferably the variant comprises the sequence of SEQ ID NO: 16.

In one embodiment the variant has at least 70% sequence identity to a polypeptide with the amino acid sequence of any one of SEQ ID NO: 1 to 5.

In a further embodiment the polynucleotide encodes a polypeptide with an amino acid sequence that has at least 70% identity to the sequence of SEQ ID NO: 1.

In a further embodiment the polynucleotide encodes a polypeptide with the amino acid sequence of SEQ ID NO: 1.

In a further embodiment the polynucleotide encodes a polypeptide with an amino acid sequence that has at least 70% identity to the sequence of SEQ ID NO: 2.

In a further embodiment the polynucleotide encodes a polypeptide with the amino acid sequence of SEQ ID NO: 2.

In a further embodiment the polynucleotide encodes a polypeptide with an amino acid sequence that has at least 70% identity to the sequence of SEQ ID NO: 3.

In a further embodiment the polynucleotide encodes a polypeptide with the amino acid sequence of SEQ ID NO: 3.

In a further embodiment the polynucleotide encodes a polypeptide with an amino acid sequence that has at least 70% identity to the sequence of SEQ ID NO: 4.

In a further embodiment the polynucleotide encodes a polypeptide with the amino acid sequence of SEQ ID NO: 4.

In a further embodiment the polynucleotide encodes a polypeptide with an amino acid sequence that has at least 70% identity to the sequence of SEQ ID NO: 5.

In a further embodiment the polynucleotide encodes a polypeptide with the amino acid sequence of SEQ ID NO: 5.

In a preferred embodiment of the method for producing a plant cell or plant with increased phlorizin content, the plant cell or plant is also transformed with a polynucleotide encoding a phloretin synthase.

Transformation with the phloretin glycosyltransferase and synthase may be sequential, in either order. Alternatively transformation with the phloretin glycosyltransferase and synthase may be simultaneous. When simultaneous, sequences encoding the phloretin glycosyltransferase and synthase may be on the same or separate constructs or vectors.

In a further aspect the invention provides a method of producing a plant cell or plant with increased phlorizin content, the method comprising transformation of a plant cell or plant with a polynucleotide comprising a nucleotide sequence selected from any one the sequences of SEQ ID NO: 7 to 18, or a variant thereof.

Preferably the variant encodes a polypeptide with phloretin glycosyltransferase activity.

Preferably the variant encodes a polypeptide comprising the sequence of SEQ ID NO: 16.

In a further aspect the invention provides a method of producing a plant cell or plant with increased phloretin glycosyltransferase activity, the method comprising transformation of a plant cell or plant with a polynucleotide comprising a nucleotide sequence selected from any one the sequences of SEQ ID NO: 6 to 15, or a variant thereof.

Preferably the variant encodes a polypeptide which has phloretin glycosyltransferase activity.

Preferably the variant encodes a polypeptide comprising the sequence of SEQ ID NO: 16.

In one embodiment the variant comprises a sequence with at least 70% sequence identity to any one of the sequences of SEQ ID NO: 6 to 15.

In a further embodiment the polynucleotide comprises a sequence with at least 70% identity to any one the sequences of SEQ ID NO: 6 to 15.

In a further embodiment the polynucleotide comprises a sequence with at least 70% sequence identity to the sequence of SEQ ID NO: 6.

In a further embodiment the polynucleotide comprises the sequence of SEQ ID NO: 7.

In a further embodiment the polynucleotide comprises a sequence with at least 70% sequence identity to the sequence of SEQ ID NO: 7.

In a further embodiment the polynucleotide comprises the sequence of SEQ ID NO: 7.

In a further embodiment the polynucleotide comprises a sequence with at least 70% sequence identity to the sequence of SEQ ID NO: 8.

In a further embodiment the polynucleotide comprises the sequence of SEQ ID NO: 8.

In a further embodiment the polynucleotide comprises a sequence with at least 70% sequence identity to the sequence of SEQ ID NO: 9.

In a further embodiment the polynucleotide comprises the sequence of SEQ ID NO: 9.

In a further embodiment the polynucleotide comprises a sequence with at least 70% sequence identity to the sequence of SEQ ID NO: 10.

In a further embodiment the polynucleotide comprises the sequence of SEQ ID NO: 10.

In a further embodiment the polynucleotide comprises a sequence with at least 70% sequence identity to the sequence of SEQ ID NO: 11.

In a further embodiment the polynucleotide comprises the sequence of SEQ ID NO: 11.

In a further embodiment the polynucleotide comprises a sequence with at least 70% sequence identity to the sequence of SEQ ID NO: 12.

In a further embodiment the polynucleotide comprises the sequence of SEQ ID NO: 12.

In a further embodiment the polynucleotide comprises a sequence with at least 70% sequence identity to the sequence of SEQ ID NO: 13.

In a further embodiment the polynucleotide comprises the sequence of SEQ ID NO: 13.

In a further embodiment the polynucleotide comprises a sequence with at least 70% sequence identity to the sequence of SEQ ID NO: 14.

In a further embodiment the polynucleotide comprises the sequence of SEQ ID NO: 14.

In a further embodiment the polynucleotide comprises a sequence with at least 70% sequence identity to the sequence of SEQ ID NO: 15.

In a further embodiment the polynucleotide comprises the sequence of SEQ ID NO: 15.

In a preferred embodiment of the method of producing a plant cell or plant with increased phlorizin content, the plant cell or plant is also transformed with a polynucleotide encoding a phloretin synthase.

Transformation with the phloretin glycosyltransferase and synthase may be sequential, in either order. Alternatively transformation with the phloretin glycosyltransferase and synthase may be simultaneous. When simultaneous, sequences encoding the glycosyltransferase and synthase may be on the same or separate constructs or vectors.

In a further aspect the invention provides an isolated polynucleotide encoding a polypeptide comprising a sequence selected any one of SEQ ID NO: 2 to 5 or a variant thereof.

Preferably the variant has phloretin glycosyltransferase activity.

Preferably the variant comprises the sequence of SEQ ID NO: 16.

In one embodiment the variant comprises a sequence with at least 80% identity to SEQ ID NO: 2:

In a further embodiment the polypeptide comprises the sequence of SEQ ID NO: 2.

In one embodiment the variant comprises a sequence with at least 80% identity to SEQ ID NO: 3:

In a further embodiment the polypeptide comprises the sequence of SEQ ID NO: 3.

In one embodiment the variant comprises a sequence with at least 80% identity to SEQ ID NO: 4:

In a further embodiment the polypeptide comprises the sequence of SEQ ID NO: 4.

In one embodiment the variant comprises a sequence with at least 80% identity to SEQ ID NO: 5:

In a further embodiment the polypeptide comprises the sequence of SEQ ID NO: 5.

In a further aspect the invention provides an isolated polynucleotide comprising the sequence of any one of SEQ ID NO: 8 to 15, or a variant thereof.

Preferably the variant encodes a phloretin glycosyltransferase.

Preferably the variant encodes a polypeptide comprising the sequence of SEQ ID NO: 16.

In one embodiment the variant comprises a sequence with at least 70% sequence identity to the sequence of SEQ ID NO: 8.

In one embodiment the polynucleotide comprises the sequence of any one of SEQ ID NO: 8.

In one embodiment the variant comprises a sequence with at least 70% sequence identity to the sequence of SEQ ID NO: 9.

In one embodiment the polynucleotide comprises the sequence of any one of SEQ ID NO: 9.

In one embodiment the variant comprises a sequence with at least 70% sequence identity to the sequence of SEQ ID NO: 10.

In one embodiment the polynucleotide comprises the sequence of any one of SEQ ID NO: 10.

In one embodiment the variant comprises a sequence with at least 70% sequence identity to the sequence of SEQ ID NO: 11.

In one embodiment the polynucleotide comprises the sequence of any one of SEQ ID NO: 11.

In one embodiment the variant comprises a sequence with at least 70% sequence identity to the sequence of SEQ ID NO: 12.

In one embodiment the polynucleotide comprises the sequence of any one of SEQ ID NO: 12.

In one embodiment the variant comprises a sequence with at least 70% sequence identity to the sequence of SEQ ID NO: 13.

In one embodiment the polynucleotide comprises the sequence of any one of SEQ ID NO: 13.

In one embodiment the variant comprises a sequence with at least 70% sequence identity to the sequence of SEQ ID NO: 14.

In one embodiment the polynucleotide comprises the sequence of any one of SEQ ID NO: 14.

In one embodiment the variant comprises a sequence with at least 70% sequence identity to the sequence of SEQ ID NO: 15.

In one embodiment the polynucleotide comprises the sequence of any one of SEQ ID NO: 15.

In a further aspect the invention provides an isolated polypeptide comprising the amino acid sequence of SEQ ID NO: 2 to 5, or a variant thereof.

Preferably the variant has phloretin glycosyltransferase activity.

Preferably the variant comprises the sequence of SEQ ID NO: 16.

In one embodiment the variant polypeptide has at least 80% sequence identity to an amino acid sequence selected from any one of SEQ ID NO: 2 to 5.

In a further embodiment the isolated polypeptide has at least 80% sequence identity to the amino acid sequence of SEQ ID NO: 2.

In a further embodiment the isolated polypeptide comprises the amino acid sequence of SEQ ID NO: 2.

In a further embodiment the isolated polypeptide has at least 80% sequence identity to the amino acid sequence of SEQ ID NO: 3.

In a further embodiment the isolated polypeptide comprises the amino acid sequence of SEQ ID NO: 3.

In a further embodiment the isolated polypeptide has at least 80% sequence identity to the amino acid sequence of SEQ ID NO: 4.

In a further embodiment the isolated polypeptide comprises the amino acid sequence of SEQ ID NO: 4.

In a further embodiment the isolated polypeptide has at least 80% sequence identity to the amino acid sequence of SEQ ID NO: 5.

In a further aspect the invention provides an isolated polynucleotide encoding a polypeptide of the invention.

In a further aspect the invention provides an isolated polynucleotide comprising:
 a) a polynucleotide comprising a fragment, of at at least 15 nucleotides in length, of a polynucleotide of the invention;
 b) a polynucleotide comprising a complement, of at at least 15 nucleotides in length, of the polynucleotide of the invention; or
 d) a polynucleotide comprising a sequence, of at at least 15 nucleotides in length, capable of hybridising to the polynucleotide of the invention.

In a further aspect the invention provides a genetic construct which comprises a polynucleotide of the invention.

In a further aspect the invention provides an expression construct which comprises a polynucleotide of the invention.

In a further aspect the invention provides an RNAi construct which comprises a polynucleotide of the invention.

In a further aspect the invention provides a vector comprising an expression construct, genetic construct or RNAi construct of the invention.

In a further aspect the invention provides a host cell genetically modified to express a polynucleotide of the invention, or a polypeptide of the invention.

Preferably the host cell is also genetically modified to express a polynucleotide encoding phloretin synthase.

In a further aspect the invention provides a host cell comprising an expression construct or genetic construct of the invention.

Preferably the host cell is also comprises an expression construct or genetic construct including a polynucleotide encoding phloretin synthase.

In a further aspect the invention provides a method for producing a phloretin glycosyltransferase polypeptide, the method comprising culturing a host cell comprising an expression construct of the invention or a genetic construct of the invention, capable of expressing a phloretin glycosyltransferase polypeptide.

In a further aspect the invention provides a method for producing the enzymic product of a phloretin glycosyltransferase, the method comprising culturing a host cell including an expression construct of the invention or an genetic construct of the invention, capable of expressing a phloretin glycosyltransferase polypeptide, in the presence of enzymic substrate which may be supplied to, or may be naturally present within the host cell.

In a further aspect the invention provides a method for the biosynthesis of phlorizin comprising the steps of culturing a host cell comprising an expression construct of the invention or a genetic construct of the invention, capable of expressing a phloretin glycosyltransferase, in the presence of a phloretin which may be supplied to, or may be naturally present within the host cell.

Preferably the host cell is also genetically modified to express a polynucleotide encoding phloretin synthase.

Preferably the host cell is a plant cell. Preferably the plant cell is part of a plant.

In a further aspect the invention provides a plant cell genetically modified to express a polynucleotide of the invention, or a polypeptide of the invention.

In a further aspect the invention provides a plant cell which comprises an expression construct of the invention or the genetic construct of the invention.

In a further aspect the invention provides a plant which comprises a plant cell of the invention.

Preferably the plant cells or plants of the invention are also genetically modified to express a polynucleotide encoding a phloretin synthase.

Preferably the host cell is also genetically modified to express a polynucleotide encoding a phloretin synthase.

It may be desirable, in some cases, to reduce phloretin glycosyltransferase activity and/or phlorizin content in a plant. This can be achieved by down-regulating expression of endogenous phloretin glycosyltransferase genes using the phloretin glycosyltransferase sequences, or fragments thereof, disclosed herein. Methods for down-regulation or silencing endogenous genes in plants are well known to those skilled in the the art and described herein.

In a further aspect the invention provides a method for selecting a plant altered in phloretin glycosyltransferase activity, the method comprising testing of a plant for altered expression of a polynucleotide of the invention.

In a further aspect the invention provides a method for selecting a plant altered in phloretin glycosyltransferase activity, the method comprising testing of a plant for altered expression of a polypeptide of the invention.

In a further aspect the invention provides a method for selecting a plant with altered phlorizin content; the method comprising testing of a plant for altered expression of a polynucleotide or polypeptide of the invention.

In a further aspect the invention provides a method for selecting a plant with altered phlorizin content; the method comprising testing of a plant for altered expression of a polypeptide or polypeptide of the invention.

In a further aspect the invention provides a plant cell or plant produced by the method of the invention. Preferably the plant is genetically modified to include a polynucleotide or polypeptide of the invention.

In a preferred embodiment of the method the plant cell or plant is also transformed with a polynucleotide encoding a phloretin synthase.

In a further aspect the invention provides a group or population of plants selected by the method of the invention.

In a further aspect the invention provides a method of producing phlorizin, the method comprising extracting phlorizin from a plant cell or plant of the invention.

In a further aspect the invention provides an antibody raised against a polypeptide of the invention.

In a further aspect the invention provides method of producing phlorizin, the method comprising contacting phloretin with the expression product of an expression construct comprising a polynucleotide of the invention or a polypeptide of the invention to obtain phlorizin.

The polynucleotides and variants of polynucleotides, of the invention may be derived from any species. The polynucleotides and variants may also be recombinantly produced and also may be the products of "gene shuffling' approaches.

In one embodiment the polynucleotide or variant, is derived from a plant species.

In a further embodiment the polynucleotide or variant, is derived from a *gymnosperm* plant species.

In a further embodiment the polynucleotide or variant, is derived from an *angiosperm* plant species.

In a further embodiment the polynucleotide or variant, is derived from a from *dicotyledonuous* plant species.

The polypeptides and variants of polypeptides of the invention may be derived from any species. The polypeptides and variants may also be recombinantly produced and also may also be expressed from the products of "gene shuffling' approaches.

In one embodiment the polypeptides or variants of the invention are derived from plant species.

In a further embodiment the polypeptides or variants of the invention are derived from gymnosperm plant species.

In a further embodiment the polypeptides or variants of the invention are derived from angiosperm plant species.

In a further embodiment the polypeptides or variants of the invention are derived from dicotyledonous plant species.

The plant cells and plants of the invention, including those from which the polynucleotides, variant polynucleotides, polypeptide and variant polypeptides are derived, may be from any species.

In one embodiment the plants cells and plants are from *gymnosperm* species.

In a further embodiment the plants cells and plants are from *angiosperm* species.

In a further embodiment the plants cells and plants are from *dicotyledonuous* species.

In a further embodiment the plants cells and plants of the invention are from *monocotyledonous* species.

In a preferred embodiment the plants cells and plants are from a species selected from a group comprising but not limited to the following genera: *Smilax, Lithocarpus, Fragaria* and *Malus*.

Preferred plant species are: *Smilax glyciphylla, Lithocarpus polystachyus, Fragaria, Malus domestica* and *Malus sieboldii*.

A particularly preferred genus is *Malus*.

Preferred *Malus* species include: *Malus aldenhamii Malus angustifolia, Malus asiatica, Malus baccata, Malus coronaria, Malus domestica, Malus doumeri, Malus florentina, Malus floribunda, Malus fusca, Malus halliana, Malus honanensis, Malus hupehensis, Malus ioensis, Malus kansuensis, Malus mandshurica, Malus micromalus, Malus niedzwetzkyana, Malus ombrophilia, Malus orientalis, Malus prattii, Malus prunifolia, Malus pumila, Malus sargentii, Malus sieboldii, Malus sieversii, Malus sylvestris, Malus toringoides, Malus transitoria, Malus trilobata, Malus tschonoskii, Malus×domestica, Malus×domestica×Malus sieversii, Malus sylvestris, Malus×domestica×Pyrus communis, Malus xiaojinensis, Malus yunnanensis, Malus* sp., *Mespilus germanica,*

A particularly preferred plant species is *Malus domestica*.

DETAILED DESCRIPTION

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

Polynucleotides and Fragments

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

A "fragment" of a polynucleotide sequence provided herein is a subsequence of contiguous nucleotides that is capable of specific hybridization to a target of interest, e.g., a sequence that is at least 15 nucleotides in length. The fragments of the invention comprise 15 nucleotides, preferably at least 20 nucleotides, more preferably at least 30 nucleotides, more preferably at least 50 nucleotides, more preferably at least 50 nucleotides and most preferably at least 60 nucleotides of contiguous nucleotides of a polynucleotide of the invention. A fragment of a polynucleotide sequence can be used in antisense, gene silencing, triple helix or ribozyme technology, or as a primer, a probe, included in a microarray, or used in polynucleotide-based selection methods of the invention.

The term "primer" refers to a short polynucleotide, usually having a free 3'OH group, that is hybridized to a template and used for priming polymerization of a polynucleotide complementary to the target.

The term "probe" refers to a short polynucleotide that is used to detect a polynucleotide sequence, that is complementary to the probe, in a hybridization-based assay. The probe may consist of a "fragment" of a polynucleotide as defined herein.

Polypeptides and Fragments

The term "polypeptide", as used herein, encompasses amino acid chains of any length but preferably at least 5 amino acids, including full-length proteins, in which amino acid residues are linked by covalent peptide bonds. Polypeptides of the present invention may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof A "fragment" of a polypeptide is a subsequence of the polypeptide that performs a function that is required for the biological activity and/or provides three dimensional structure of the polypeptide. The term may refer to a polypeptide, an aggregate of a polypeptide such as a dimer or other multimer, a fusion polypeptide, a polypeptide fragment, a polypeptide variant, or derivative thereof capable of performing the above enzymatic activity.

The term "isolated" as applied to the polynucleotide or polypeptide sequences disclosed herein is used to refer to sequences that are removed from their natural cellular environment. An isolated molecule may be obtained by any method or combination of methods including biochemical, recombinant, and synthetic techniques.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

The term "derived from" with respect to polynucleotides or polypeptides of the invention being derived from a particular genera or species, means that the polynucleotide or polypeptide has the same sequence as a polynucleotide or polypeptide found naturally in that genera or species. The polynucleotide or polypeptide, derived from a particular genera or species, may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occuring allelic variants, or non-naturally occurring variants. Variants may be from the same or from other species and may encompass homologues, paralogues and orthologues. In certain embodiments, variants of the inventive polypeptides and polypeptides possess biological activities that are the same or similar to those of the inventive polypeptides or polypeptides. The term "variant" with reference to polypeptides and polypeptides encompasses all forms of polypeptides and polypeptides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequence of the present invention. Identity is found over a comparison window of at least 20 nucleotide positions, preferably at least 50 nucleotide positions, more preferably at least 100 nucleotide positions, and most preferably over the entire length of a polynucleotide of the invention.

Polynucleotide sequence identity can be determined in the following manner. The subject polynucleotide sequence is compared to a candidate polynucleotide sequence using BLASTN (from the BLAST suite of programs, version 2.2.5 [November 2002]) in bl2seq (Tatiana A. Tatusova, Thomas L. Madden (1999), "Blast 2 sequences—a new tool for comparing protein and nucleotide sequences", FEMS Microbiol Lett. 174:247-250), which is publicly available from NCBI (ftp:// ftp.ncbi.nih.gov/blast/). The default parameters of bl2seq are utilized except that filtering of low complexity parts should be turned off.

The identity of polynucleotide sequences may be examined using the following unix command line parameters:

bl2seq -i nucleotideseq1 -j nucleotideseq2 -F F -p blastn

The parameter -F F turns off filtering of low complexity sections. The parameter -p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which can be obtained from http://www.hgmp.mrc.ac.uk/Software/EMBOSS/. The European Bioinformatics Institute server also provides the facility to perform EMBOSS-needle global alignments between two sequences on line at http:/www.ebi.ac.uk/emboss/align/.

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

A preferred method for calculating polynucleotide % sequence identity is based on aligning sequences to be compared using Clustal X (Jeanmougin et al., 1998, *Trends Biochem. Sci.* 23, 403-5.)

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI (ftp://ftp.ncbi.nih.gov/blast/).

The similarity of polynucleotide sequences may be examined using the following unix command line parameters:

bl2seq -i nucleotideseq1 -j nucleotideseq2 -F F -p tblastx

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1\times10^{-6}$ more preferably less than $1\times10^{-9}$, more preferably less than $1\times10^{-12}$, more preferably less than $1\times10^{-15}$, more preferably less than $1\times10^{-18}$, more preferably less than $1\times10^{-21}$, more preferably less than $1\times10^{-30}$, more preferably less than $1\times10^{-40}$, more preferably less than $1\times10^{-50}$, more preferably less than $1\times10^{-60}$, more preferably less than $1\times10^{-70}$, more preferably less than $1\times10^{-80}$, more preferably less than $1\times10^{-90}$ and most preferably less than $1\times10^{-100}$ when compared with any one of the specifically identified sequences.

Alternatively, variant polynucleotides of the present invention hybridize to the specified polynucleotide sequences, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing). Tm for polynucleotide molecules greater than about 100 bases can be calculated by the formula Tm=81.5+0.41% (G+C-log (Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides of the present invention also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [November 2002]) from NCBI (ftp://ftp.ncbi.nih.gov/blast/) via the tblastx algorithm as previously described.

The function of a variant polynucleotide of the invention as a phloretin glycosyltransferase may be assessed for example by expressing such a sequence in bacteria and testing activity of the encoded protein as described in the Example section. Function of a variant may also be tested for it ability to alter phloretin glycosyltransferase activity or phloretin content in plants, also as described in the Examples section herein.

Polypeptide Variants

The term "variant" with reference to polypeptides encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 50 amino acid positions, more preferably at least 100 amino acid positions, and most preferably over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available from NCBI (ftp://ftp.ncbi.nih.gov/blast/). The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available at http://www.ebi.ac.uk/emboss/align/) and GAP (Huang, X. (1994) On Global Sequence Alignment. Computer Applications in the Biosciences 10, 227-235.) as discussed above are also suitable global sequence alignment programs for calculating polypeptide sequence identity.

A preferred method for calculating polypeptide % sequence identity is based on aligning sequences to be compared using Clustal X (Jeanmougin et al., 1998, *Trends Biochem. Sci.* 23, 403-5.)

Polypeptide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI (ftp://ftp.ncbi.nih.gov/blast/).

The similarity of polypeptide sequences may be examined using the following unix command line parameters:

bl2seq -i peptideseq1 -j peptideseq2 -F F -p blastp

Variant polypeptide sequences preferably exhibit an E value of less than $1\times10^{-6}$ more preferably less than $1\times10^{-9}$, more preferably less than $1\times10^{-12}$, more preferably less than $1\times10^{-15}$, more preferably less than $1\times10^{-18}$, more preferably less than $1\times10^{-21}$, more preferably less than $1\times10^{-30}$, more preferably less than $1\times10^{-40}$, more preferably less than $1\times10^{-50}$, more preferably less than $1\times10^{-60}$, more preferably less than $1\times10^{-70}$, more preferably less than $1\times10^{-80}$, more preferably less than $1\times10^{-90}$ and most preferably $1\times10^{-100}$ when compared with any one of the specifically identified sequences.

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

The function of a polypeptide variant as a phloretin glycosyltransferase may be assessed by the methods described in the Example section herein.

Constructs, Vectors and Components Thereof

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as *E. coli*.

The term "expression construct" refers to a genetic construct that includes the necessary elements that permit transcribing the insert polynucleotide molecule, and, optionally, translating the transcript into a polypeptide. An expression construct typically comprises in a 5' to 3' direction:

a) a promoter functional in the host cell into which the construct will be transformed,
b) the polynucleotide to be expressed, and
c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a "coding sequence" is capable of being expressed when it is operably linked to promoter and terminator sequences.

"Operably-linked" means that the sequenced to be expressed is placed under the control of regulatory elements that include promoters, tissue-specific regulatory elements, temporal regulatory elements, enhancers, repressors and terminators.

The term "noncoding region" refers to untranslated sequences that are upstream of the translational start site and downstream of the translational stop site. These sequences are also referred to respectively as the 5' UTR and the 3' UTR. These regions include elements required for transcription initiation and termination and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate gene transcription. Promoters comprise cis-initiator elements which specify the transcription initiation site and conserved boxes such as the TATA box, and motifs that are bound by transcription factors.

A "transgene" is a polynucleotide that is taken from one organism and introduced into a different organism by transformation. The transgene may be derived from the same species or from a different species as the species of the organism into which the transgene is introduced.

An "inverted repeat" is a sequence that is repeated, where the second half of the repeat is in the complementary strand, e.g.,

```
(5')GATCTA.......TAGATC(3')

(3')CTAGAT.......ATCTAG(5')
```

Read-through transcription will produce a transcript that undergoes complementary base-pairing to form a hairpin structure provided that there is a 3-5 bp spacer between the repeated regions.

Host Cells

Host cells may be derived from, for example, bacterial, fungal, insect, mammalian or plant organisms.

A "transgenic plant" refers to a plant which contains new genetic material as a result of genetic manipulation or transformation. The new genetic material may be derived from a plant of the same species as the resulting transgenic plant or from a different species.

The applicants have identified novel polynucleotides (SEQ ID NO: 6 to 15) that encode novel polypeptides (SEQ ID NO: 2 to 5) that have phloretin glycosyltransferase activity, as summarised in Table 1.

The applicants have shown that all of the phloretin glycosyltransferase polypeptides sequences disclosed (SEQ ID NO: 1 to 5) show significant sequence conservation and are variants of one another.

Similarly the applicants have shown that all of the disclosed phloretin glycosyltransferase polynucleotides sequences (SEQ ID NO: 6 to 15) show significant sequence conservation and are variants of one another.

The invention provides genetic constructs, vectors and plants containing the novel polynucleotide sequences (SEQ ID NO: 6 to 15) or sequences encoding the novel polypeptide sequences (SEQ ID NO: 2 to 5). The invention also provides plants comprising the genetic construct and vectors of the invention.

The invention provides plants altered in phloretin glycosyltransferase activity, relative to suitable control plants, and plants altered in phlorizin content relative to suitable control plants. The invention provides plants with increased phloretin glycosyltransferase activity and increased phlorizin.

The invention also provides methods for the production of such plants and methods of selection of such plants.

Suitable control plants include non-transformed plants of the same species or variety or plants transformed with control constructs.

Methods for Isolating or Producing Polynucleotides

The polynucleotide molecules of the invention can be isolated by using a variety of techniques known to those of ordinary skill in the art. By way of example, such polypeptides can be isolated through use of the polymerase chain reaction (PCR) described in Mullis et al., Eds. 1994 The Polymerase Chain Reaction, Birkhauser, incorporated herein by reference. The polypeptides of the invention can be amplified using primers, as defined herein, derived from the polynucleotide sequences of the invention.

Further methods for isolating polynucleotides of the invention include use of all, or portions of, the polypeptides having the sequence set forth herein as hybridization probes. The technique of hybridizing labelled polynucleotide probes to polynucleotides immobilized on solid supports such as nitrocellulose filters or nylon membranes, can be used to screen the genomic or cDNA libraries. Exemplary hybridization and wash conditions are: hybridization for 20 hours at 65° C. in 5.0×SSC, 0.5% sodium dodecyl sulfate, 1×Denhardt's solution; washing (three washes of twenty minutes each at 55° C.) in 1.0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1× SSC, 1% (w/v) sodium dodecyl sulfate, at 60° C.

The polynucleotide fragments of the invention may be produced by techniques well-known in the art such as restriction endonuclease digestion, oligonucleotide synthesis and PCR amplification.

A partial polynucleotide sequence may be used, in methods well-known in the art to identify the corresponding full length polynucleotide sequence. Such methods include PCR-based methods, 5'RACE (Frohman Mass., 1993, Methods Enzymol. 218: 340-56) and hybridization-based method, computer/database—based methods. Further, by way of example, inverse PCR permits acquisition of unknown sequences, flanking the polynucleotide sequences disclosed herein, starting with primers based on a known region (Triglia et al., 1998, *Nucleic Acids Res* 16, 8186, incorporated herein by reference). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. Additionally when down-regulation of a gene is the desired result, it may be necessary to utilise a sequence identical (or at least highly similar) to that in the plant, for which reduced expression is desired. For these reasons among others, it is desirable to be able to identify and isolate orthologues of a particular gene in several different plant species.

Variants (including orthologues) may be identified by the methods described.

Methods for Identifying Variants

Physical Methods

Variant polypeptides may be identified using PCR-based methods (Mullis et al., Eds. 1994 The Polymerase Chain Reaction, Birkhauser). Typically, the polynucleotide sequence of a primer, useful to amplify variants of polynucleotide molecules of the invention by PCR, may be based on a sequence encoding a conserved region of the corresponding amino acid sequence.

Alternatively library screening methods, well known to those skilled in the art, may be employed (Sambrook et al., Molecular Cloning: A Laboratory Manual, 2nd Ed. Cold Spring. Harbor Press, 1987). When identifying variants of the probe sequence, hybridization and/or wash stringency will typically be reduced relatively to when exact sequence matches are sought.

Polypeptide variants may also be identified by physical methods, for example by screening expression libraries using antibodies raised against polypeptides of the invention (Sambrook et al., Molecular Cloning: A Laboratory Manual, 2nd Ed. Cold Spring Harbor Press, 1987) or by identifying polypeptides from natural sources with the aid of such antibodies.

Computer Based Methods

The variant sequences of the invention, including both polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which are publicly available from (ftp://ftp.ncbi.nih.gov/blast/) or from the National Center for Biotechnology Information (NCBI), National Library of Medicine, Building 38A, Room 8N805, Bethesda, Md. 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673-4680, http://www-igbmc.u-strasbg.fr/BioInfo/ClustalW/Top.html) or T-COFFEE (Cedric Notredame, Desmond G. Higgins, Jaap Heringa, T-Coffee: A novel method for fast and accurate multiple sequence alignment, J. Mol. Biol. (2000) 302: 205-217)) or PILEUP, which uses progressive, pairwise alignments. (Feng and Doolittle, 1987, J. Mol. Evol. 25, 351). Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (www.expasy.org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

The function of a variant polynucleotide of the invention as encoding phloretin glycosyltransferases can be tested for the activity, or can be tested for their capability to alter phlorizin content in plants by methods described in the examples section herein.

Methods for Isolating Polypeptides

The polypeptides of the invention, including variant polypeptides, may be prepared using peptide synthesis methods well known in the art such as direct peptide synthesis using solid phase techniques (e.g. Stewart et al., 1969, in Solid-Phase Peptide Synthesis, WH Freeman Co, San Francisco Calif., or automated synthesis, for example using an Applied Biosystems 431A Peptide Synthesizer (Foster City, Calif.). Mutated forms of the polypeptides may also be produced during such syntheses.

The polypeptides and variant polypeptides of the invention may also be purified from natural sources using a variety of techniques that are well known in the art (e.g. Deutscher, 1990, Ed, Methods in Enzymology, Vol. 182, *Guide to Protein Purification*).

Alternatively the polypeptides and variant polypeptides of the invention may be expressed recombinantly in suitable host cells and separated from the cells as discussed below.

Methods for Producing Constructs and Vectors

The genetic constructs of the present invention comprise one or more polynucleotide sequences of the invention and/or polynucleotides encoding polypeptides of the invention, and may be useful for transforming, for example, bacterial, fungal, insect, mammalian or plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Polynucleotides, Constructs or Vectors The invention provides a host cell which comprises a genetic construct or vector of the invention.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides of the invention. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Methods for Producing Plant Cells and Plants Comprising Constructs and Vectors

The invention further provides plant cells which comprise a genetic construct of the invention, and plant cells modified to alter expression of a polynucleotide or polypeptide of the invention. Plants comprising such cells also form an aspect of the invention.

Alteration of phloretin glycosyltransferase activity may be altered in a plant through methods of the invention. Such methods may involve the transformation of plant cells and plants, with a construct designed to alter expression of a polynucleotide or polypeptide which modulates phloretin glycosyltransferase activity, or phlorizin content in such plant cells and plants. Such methods also include the transformation of plant cells and plants with a combination of the construct of the invention and one or more other constructs designed to alter expression of one or more polynucleotides or polypeptides which modulate phloretin glycosyltransferase activity and/or phlorizin content in such plant cells and plants.

Methods for transforming plant cells, plants and portions thereof with polypeptides are described in Draper et al., 1988, Plant Genetic Transformation and Gene Expression. A Laboratory Manual. Blackwell Sci. Pub. Oxford, p. 365; Potrykus and Spangenburg, 1995, Gene Transfer to Plants. Springer-Verlag, Berlin.; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

Methods for Genetic Manipulation of Plants

A number of plant transformation strategies are available (e.g. Birch, 1997, Ann Rev Plant Phys Plant Mol Biol, 48, 297, Hellens R P, et al (2000) Plant Mol Biol 42: 819-32, Hellens R et al Plant Meth 1: 13). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed. Such strategies are known as gene silencing strategies.

Genetic constructs for expression of genes in transgenic plants typically include promoters for driving the expression of one or more cloned polynucleotide, terminators and selectable marker sequences to detest presence of the genetic construct in the transformed plant.

The promoters suitable for use in the constructs of this invention are functional in a cell, tissue or organ of a monocot or dicot plant and include cell-, tissue- and organ-specific promoters, cell cycle specific promoters, temporal promoters, inducible promoters, constitutive promoters that are active in most plant tissues, and recombinant promoters. Choice of promoter will depend upon the temporal and spatial expression of the cloned polynucleotide, so desired. The promoters may be those normally associated with a transgene of interest, or promoters which are derived from genes of other plants, viruses, and plant pathogenic bacteria and fungi. Those skilled in the art will, without undue experimentation, be able to select promoters that are suitable for use in modifying and modulating plant traits using genetic constructs comprising the polynucleotide sequences of the invention. Examples of constitutive plant promoters include the CaMV 35S promoter, the nopaline synthase promoter and the octopine synthase promoter, and the Ubi 1 promoter from maize. Plant promoters which are active in specific tissues, respond to internal developmental signals or external abiotic or biotic stresses are described in the scientific literature. Exemplary promoters are described, e.g., in WO 02/00894, which is herein incorporated by reference.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zein gene terminator, the *Oryza sativa*

ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenberg. Eds) Springer Verlag. Berline, pp. 325-336.

Gene silencing strategies may be focused on the gene itself or regulatory elements which effect expression of the encoded polypeptide. "Regulatory elements" is used here in the widest possible sense and includes other genes which interact with the gene of interest.

Genetic constructs designed to decrease or silence the expression of a polynucleotide/polypeptide of the invention may include an antisense copy of a polynucleotide of the invention. In such constructs the polynucleotide is placed in an antisense orientation with respect to the promoter and terminator.

An "antisense" polynucleotide is obtained by inverting a polynucleotide or a segment of the polynucleotide so that the transcript produced will be complementary to the mRNA transcript of the gene, e.g.,

```
5'GATCTA 3'          3'CTAGAT 5'
(coding strand)      (antisense strand)

3'CUAGAU 5' mRNA     5'GAUCUCG 3' antisense RNA
```

Genetic constructs designed for gene silencing may also include an inverted repeat. An 'inverted repeat' is a sequence that is repeated where the second half of the repeat is in the complementary strand, e.g.,

```
        5'-GATCTA.........TAGATC-3'

3'-CTAGAT.........ATCTAG-5'
```

The transcript formed may undergo complementary base pairing to form a hairpin structure. Usually a spacer of at least 3-5 bp between the repeated region is required to allow hairpin formation.

Another silencing approach involves the use of a small antisense RNA targeted to the transcript equivalent to an miRNA (Llave et al., 2002, Science 297, 2053). Use of such small antisense RNA corresponding to polynucleotide of the invention is expressly contemplated.

The term genetic construct as used herein also includes small antisense RNAs and other such polypeptides effecting gene silencing.

Transformation with an expression construct, as herein defined, may also result in gene silencing through a process known as sense suppression (e.g. Napoli et al., 1990, Plant Cell 2, 279; de Carvalho Niebel et al., 1995, Plant Cell, 7, 347). In some cases sense suppression may involve over-expression of the whole or a partial coding sequence but may also involve expression of non-coding region of the gene, such as an intron or a 5' or 3' untranslated region (UTR). Chimeric partial sense constructs can be used to coordinately silence multiple genes (Abbott et al., 2002, Plant Physiol. 128(3): 844-53; Jones et al., 1998, Planta 204: 499-505). The use of such sense suppression strategies to silence the expression of a polynucleotide of the invention is also contemplated.

The polynucleotide inserts in genetic constructs designed for gene silencing may correspond to coding sequence and/or non-coding sequence, such as promoter and/or intron and/or 5' or 3' UTR sequence, or the corresponding gene.

Other gene silencing strategies include dominant negative approaches and the use of ribozyme constructs (McIntyre, 1996, Transgenic Res, 5, 257)

Pre-transcriptional silencing may be brought about through mutation of the gene itself or its regulatory elements. Such mutations may include point mutations, frameshifts, insertions, deletions and substitutions.

The following are representative publications disclosing genetic transformation protocols that can be used to genetically transform the following plant species: Rice (Alam et al., 1999, Plant Cell Rep. 18, 572); apple (Yao et al., 1995, Plant Cell Reports 14, 407-412); maize (U.S. Pat. Nos. 5,177,010 and 5,981,840); wheat (Ortiz et al., 1996, Plant Cell Rep. 15, 1996, 877); tomato (U.S. Pat. No. 5,159,135); potato (Kumar et al., 1996 Plant J. 9, 821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); grasses (U.S. Pat. Nos. 5,187,073 and 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. No. 5,792, 935); soybean (U.S. Pat. Nos. 5,416,011; 5,569,834; 5,824, 877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037,522); brassica (U.S. Pat. Nos. 5,188,958; 5,463,174 and 5,750,871); cereals (U.S. Pat. No. 6,074,877); pear (Matsuda et al., 2005, Plant Cell Rep. 24(1):45-51); Prunus (Ramesh et al., 2006 Plant Cell Rep. 25(8):821-8; Song and Sink 2005 Plant Cell Rep. 2006; 25(2):117-23; Gonzalez Padilla et al., 2003 Plant Cell Rep. 22(1):38-45); strawberry (Oosumi et al., 2006 Planta. 223(6):1219-30; Folta et al., 2006 Planta Apr. 14; PMID: 16614818), rose (Li et al., 2003), Rubus (Graham et al., 1995 Methods Mol Biol. 1995; 44:129-33), tomato (Dan et al., 2006, Plant Cell Reports V25:432-441), apple (Yao et al., 1995, *Plant Cell Rep.* 14, 407-412) and *Actinidia eriantha* (Wang et al., 2006, Plant Cell Rep. 25, 5: 425-31). Transformation of other species is also contemplated by the invention. Suitable methods and protocols are available in the scientific literature.

Several further methods known in the art may be employed to alter expression of a nucleotide and/or polypeptide of the invention. Such methods include but are not limited to Tilling (Till et al., 2003, Methods Mol Biol, 2%, 205), so called "Deletagene" technology (Li et al., 2001, Plant Journal 27(3), 235) and the use of artificial transcription factors such as synthetic zinc finger transcription factors. (e.g. Jouvenot et al., 2003, Gene Therapy 10, 513). Additionally antibodies or fragments thereof, targeted to a particular polypeptide may also be expressed in plants to modulate the activity of that polypeptide (Jobling et al., 2003, Nat. Biotechnol., 21(1), 35). Transposon tagging approaches may also be applied. Additionally peptides interacting with a polypeptide of the invention may be identified through technologies such as phage-display (Dyax Corporation). Such interacting peptides may be expressed in or applied to a plant to affect activity of a polypeptide of the invention. Use of each of the above approaches in alteration of expression of a nucleotide and/or polypeptide of the invention is specifically contemplated.

The terms "to alter expression of" and "altered expression" of a polynucleotide or polypeptide of the invention, are intended to encompass the situation where genomic DNA corresponding to a polynucleotide of the invention is modified thus leading to altered expression of a polynucleotide or polypeptide of the invention. Modification of the genomic DNA may be through genetic transformation or other methods known in the art for inducing mutations. The "altered expression" can be related to an increase or decrease in the amount of messenger RNA and/or polypeptide produced and may also result in altered activity of a polypeptide due to alterations in the sequence of a polynucleotide and polypeptide produced.

Methods of Selecting Plants

Methods are also provided for selecting plants with altered phloretin glycosyltransferase or phlorizin content. Such methods involve testing of plants for altered for the expression of a polynucleotide or polypeptide of the invention. Such methods may be applied at a young age or early developmental stage when the altered phloretin glycosyltransferase activity or phlorizin content may not necessarily be easily measurable.

The expression of a polynucleotide, such as a messenger RNA, is often used as an indicator of expression of a corresponding polypeptide. Exemplary methods for measuring the expression of a polynucleotide include but are not limited to Northern analysis, RT-PCR and dot-blot analysis (Sambrook et al., Molecular Cloning: A Laboratory Manual, 2nd Ed. Cold Spring Harbor Press, 1987). Polynucleotides or portions of the polynucleotides of the invention are thus useful as probes or primers, as herein defined, in methods for the identification of plants with altered levels of phloretin glycosyltransferase or phlorizin. The polynucleotides of the invention may be used as probes in hybridization experiments, or as primers in PCR based experiments, designed to identify such plants.

Alternatively antibodies may be raised against polypeptides of the invention. Methods for raising and using antibodies are standard in the art (see for example: Antibodies, A Laboratory Manual, Harlow A Lane, Eds, Cold Spring Harbour Laboratory, 1998). Such antibodies may be used in methods to detect altered expression of polypeptides which modulate flower size in plants. Such methods may include ELISA (Kemeny, 1991, A Practical Guide to ELISA, NY Pergamon Press) and Western analysis (Towbin & Gordon, 1994, J Immunol Methods, 72, 313).

These approaches for analysis of polynucleotide or polypeptide expression and the selection of plants with altered phloretin glycosyltransferase or altered phlorizin content are useful in conventional breeding programs designed to produce varieties with altered phloretin glycosyltransferase activity or phlorizin content.

Plants

The term "plant" is intended to include a whole plant, any part of a plant, propagules and progeny of a plant.

The term 'propagule' means any part of a plant that may be used in reproduction or propagation, either sexual or asexual, including seeds and cuttings.

The plants of the invention may be grown and either self-ed or crossed with a different plant strain and the resulting hybrids, with the desired phenotypic characteristics, may be identified. Two or more generations may be grown to ensure that the subject phenotypic characteristics are stably maintained and inherited. Plants resulting from such standard breeding approaches also form an aspect of the present invention.

The function of a variant polynucleotide of the invention as encoding a phloretin glycosyltransferase may be assessed for example by expressing such a sequence in bacteria and testing activity of the encoded protein as described in the example sections herein.

Alteration of phloretin glycosyltransferase activity and/or phlorizin content may also be altered in a plant through methods of the invention. Such methods may involve the transformation of plant cells and plants, with a construct of the invention designed to alter expression of a polynucleotide or polypeptide which modulates phloretin glycosyltransferase activity and/or phlorizin content in such plant cells and plants. Such methods preferably also include the transformation of plant cells and plants with a combination of the construct of the invention and one or more other constructs designed to alter expression of one or more other polynucleotides or polypeptides which modulate ascorbic acid content in such plant cells and plants. Preferably a combination of phloretin glycosyltransferase and a phloretin synthase is expressed in the plant cells or plants.

Methods for Extracting Phlorizin from Plants

Methods are also provided for the production of phlorizin by extraction of phlorizin from a plant of the invention. Phlorizin may be extracted from plants by many different methods known to those skilled in the art.

Ridgway and Tucker 1997 extract phlorizin from young apple leaves and twigs (containing up to 10% dry weight of phlorizin). They showed that the most important determinant in a given tissue's phlorizin content is its period of development, and that cultivar, including rootstock type, had a much less pronounced effect. They recommend that production of phlorizin is best carried out by the coppicing of fast growing rootstocks, such as M25 or MM106, this being akin to the production of willow or poplar for biomass; for which mechanical harvesting has already been developed. Yields of 250 kg of phlorizin per hectare should then be readily obtained. Yields could be improved by genetic engineering. (Ridgway T & Tucker G (1997) Apple: a new agrochemical crop. Biochemical Society Transactions 25, 110S)

Hunter and Hull (1993) also provide a method for apple. Dong, H. et al (2007) provide a preparative separation of phlorhizin from the crude extract of *Lithocarpus polystachyus*. Cox et al., provide a method of extraction from *Smilax*.

These methods may be up-scaled for larger scale phlorizin extraction using approaches well-known to those skilled in the art.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

BRIEF DESCRIPTION OF THE DRAWINGS

The present invention will be better understood with reference to the accompanying drawings in which:

FIG. 9-1 through 9-2 shows a CLUSTALX alignment of the MpUGT88A1 (111441) polypeptide (SEQ ID NO:1) and variants thereof (297292, SEQ ID NO:2; 88077, SEQ ID NO:3; 87623, SEQ ID NO:4; 138221, SEQ ID NO:5), and shows the position of a completely conserved motif (SEQ ID NO: 16) present in all five sequences. The consensus sequence is presented in SEQ ID NO:26.

FIG. 10 shows the % identity between each of the sequences aligned in FIG. 9-1 through 9-2.

EXAMPLES

The invention will now be illustrated with reference to the following non-limiting example.

Example 1

Identification of a Phloretin Glycosyltransferase Sequence from Apple

Sequence Identification and Phylogenetics

GenBank apple EST sequences were BLAST searched (expect value of $exp^{-05}$) using previously published UGT genes from GenBank. EST sequences were automatically parsed through two rounds of contig building and a set of "non-redundant contig" sequences was derived. Amino acid alignments of predicted proteins were constructed using ClustalX (version 1.8). All proteins were checked for the presence of the common signature motif of 44 amino acids found in plant UGTs (Li et al. 2001). A full-length sequence in each contig was selected for complete sequencing.

For phylogenetic analysis all amino acid sequences were initially aligned using ClustalX then manually edited. *Arabidopsis* UGT sequences were obtained from the following website http://www.p450.kvl.dk/UGT.shtml. Confidence values for groupings in phylogenetic trees were obtained using BOOTSTRAP N-J TREE using 1,000 bootstrap trials. Trees were visualised in TREEVIEW (v.1.6.6).

The MpUGT88A Gene and its Predicted Protein

Figure 1:
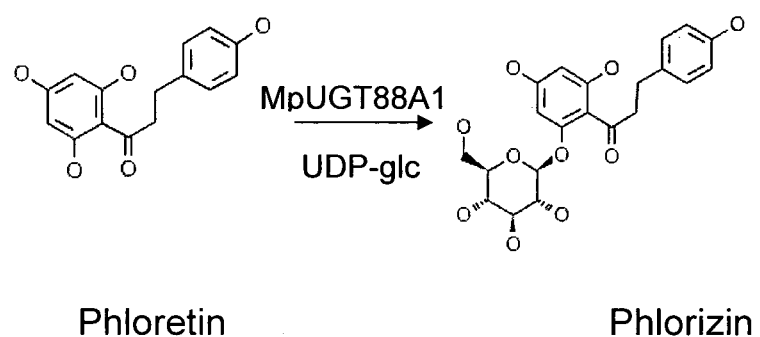
FIG. 1 shows the structure of phlorizin and its aglycone phloretin. The conversion of phloretin to phlorizin (phloretin 2'-glucoside) is mediated by *Malus domestica* uridine diphosphate glycosyltransferase (MpUGT88A1, SEQ ID NO:1) in the presence of uridine diphosphate glucose (UDP-glc).
Figure 2:
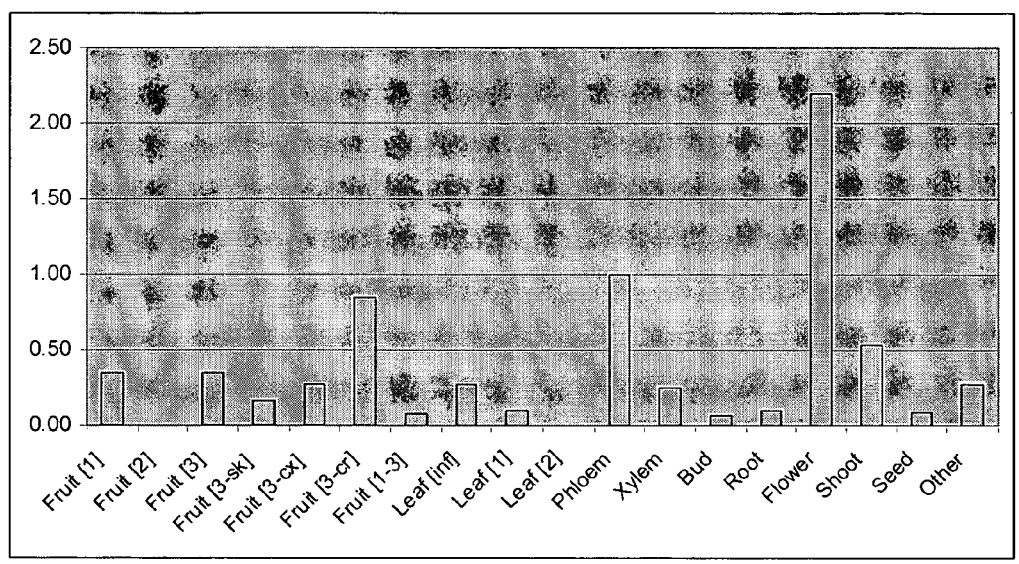
FIG. 2 shows the relative expression of MpUGT88A1 (SEQ ID NO:7) in silico. Data is based on the distribution of MpUGT88A1 ESTs by apple library in GenBank is compared. The number of MpUGT88A1 ESTs in each tissue was divided by the total number of ESTs sequenced for that tissue and expressed relative to the phloem sample. Tissue types: Fruit [1]=small fruit harvested 10 DAFB [days after full bloom]; Fruit [2]=developing fruit harvested 24-87 DAFB; Fruit [3]=ripe fruit harvested 126-150 DAFB; Fruit [3-sk]= ripe fruit skin; Fruit [3-cr]=ripe fruit cortex; Fruit [3-cr]=ripe fruit core; Fruit [1-3]=ripe fruit combining skin, cortex and core; Leaf [inf]=leaf tissue pathogen challenged; Leaf [1]=young and expanding leaf; Leaf [2]=senescing leaf, phloem; xylem; bud; root, flower, shoot, seed and other tissues.

Gene mining identified over 60 UDP-glycosyltransferase-encoding genes amongst the ~270,000 apple EST sequences in GenBank. In silico expression profiling of the apple UGT ESTs identified the gene 'MpUGT88A1' that was highly expressed (represented by 255 ESTs) in all tissues known to produce phlorizin including leaf, seed and fruit (FIG. 2). The cDNA clone (SEQ ID NO:6) for MpUGT88A1 is 1745 nucleotides in length and contains an open reading frame (SEQ ID NO:7) of 483 amino acids with 64 nucleotides of 5' UTR and 232 nucleotides of 3' UTR. The predicted MpUGT88A1 protein (SEQ ID NO:1) has a mass of 53.5 kDa and a pI of 5.8 and contains the 'PSPG' consensus sequence of 44 amino acids found in all UGTs and thought to be involved in binding of the UDP moiety of the activated sugar (Li et al. 2001). Within this consensus sequence, MpUGT88A1 contains two highly conserved motifs 'WXPQ" and "HCGWNS" (amino acids 377-382) found in 95% of UGT sequences, and an absolutely conserved glutamine at the $42^{nd}$ amino acid in the PSPG box (Vogt 2000).

Figure 3:
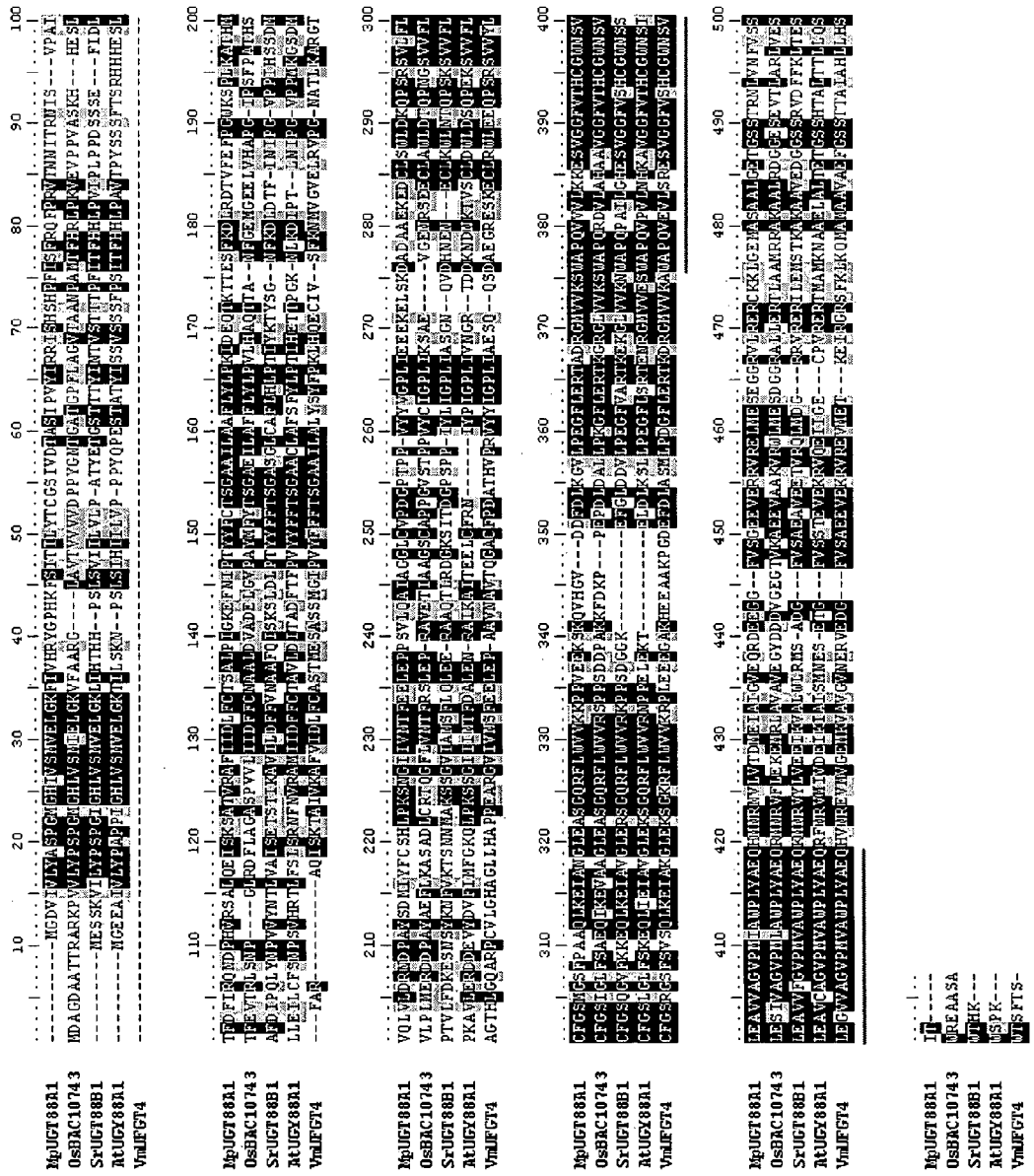
FIG. 3 shows an alignment of the MpUGT88A1 polypeptide (SEQ ID NO: 1) and other plant UGT glycosyltransferases. MpUGT88A1 (*Malus domestica*; apple, EU246349, SEQ ID NO:1); OsBAC10743 (*Oryza sativa*, rice, BAC10743 SEQ ID NO:22), SrUGT88B1 (*Stevia rebaudiana*, sweetleaf, AAR06919, SEQ ID NO:23), AtUGT88A1 (*Arabidopsis thaliana*, At3g16520, SEQ ID NO:24) and VmUFGT4 (*Vigna mungo*, black gram, BAA36412, SEQ ID NO:25). Black and grey boxes contain residues that are identical and similar, respectively. The underlined region indicates the 'PSPG' motif (amino acids 352-402 of SEQ ID NO:1) conserved in all plant glycosyltransferases.
Figure 4:
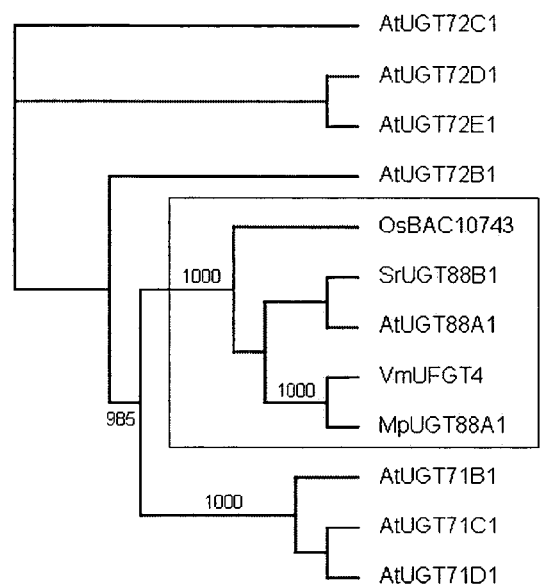
FIG. 4 shows a phylogenetic comparison of MpUGT88A1 (SEQ ID NO:1) and other plant glycosyltransferase sequences. Bootstrap values of >80% (1000 bootstrap replicates) are given. The gene identifiers are as in FIG. 3 plus *Arabidopsis thaliana* AtUGT72B1 (At4g01070); AtUGT72C1 (At4g36770); AtUGT72D1 (At2g18570); AtUGT72E1 (At3g50740); AtUGT71 B1 (At3g21750); AtUGT71 C1 (At2g29750) and AtUGT71 D1 (At2g29730). Members of UGT Family 88 are boxed.

A framework phylogenetic tree was constructed using MpUGT88A1 and representative members of the *Arabidopsis* UGT tree published by Ross et al. (2001). This framework tree indicated that MpUGT88A1 clustered with the sole *Arabidopsis* Family 88 UGT sequence AtUGT88A1 (data not shown). The apple clone was therefore designated MpUGT88A1 according the nomenclature described in Ross et al. (2001). MpUGT88A1 showed 42.5% amino acid identity with AtUGT88A1, and significant homology with two full length UGTs sequences from rice (*Oryza sativa*, BAC10743) and sweetleaf (*Stevia rebaudiana*, AAR06919) and a partial sequence from black gram (*Vigna mungo*, BAA36412, 52% amino acid identity in the region of overlap). MpUGT88A1 and these four sequences are shown aligned in FIG. 3. A more detailed phylogenetic tree was then constructed using these sequences aligned with selected members of *Arabidopsis* UGT Families 71 and 72 (the UGT Families most similar to UGT Family 88). This tree indicates that apple MpUGT88A1 and the related rice, *S. rebaudiana* and black gram sequences given in FIG. 3, clearly separate with AtUGT88A1 as part of UGT Family 88 and are distinct from other *Arabidopsis* UGT sequences (FIG. 4).

Example 2

Analysis of the Expression Profile of the Phloretin Glycosyltransferase in Plants Plant Material, RNA Extraction and qPCR Total RNA was isolated from apple tissues by a modified silica RNA extraction method (Nieuwenhuizen et al. 2007). The RNA concentration of each sample was measured using a NanoDrop® ND-1000 spectrophotometer (NanoDrop Technologies, Inc., Wilmington, Del., USA). RNA samples (~3 μg in 30 μl reactions) were treated for 30 min at 37° C. with DNase I (Ambion, Inc., Austin, Tex., USA) to remove any minor genomic DNA contamination. The DNase was heat inactivated for 30 min at 50° C. Reverse transcription was performed in 20 μl reactions as per manufacturer's instructions using SuperScript III™ RNase H-reverse transcriptase (Invitrogen, Auckland, NZ), 500 ng of RNA and the primer. NotI-PA 5'-GACTAGTTCT AGATCGCGAG CGGCCGCCCT$_{(15)}$-3' (SEQ ID NO:17).

Quantitative PCR reactions (20 μL) were repeated four times on an ABI Prism 7900HT (Applied Biosystems, Foster City, Calif., USA) using 3 μL of diluted cDNA, 0.5 μM MpUGT88A1-specific primers (Fwd 5'-GAAGGGTGTG TTGCCAGAAG GGT-3' (SEQ ID NO:18); Rev 5'-GTCAC-GAACC CACCAACCGA CT-3' [SEQ ID NO:19]), and 5 μL of Lightcycler 480 SYBR Green Master (Roche Diagnostics) following the manufacturer's instructions. Cycling conditions included an initial hot start at 95° C. for 5 min, followed by 45 cycles of 95° C. for 10 s, 60° C. for 10 s and 72° C. for 12 s. Fluorescence was measured at the end of each annealing step. Each PCR reaction was followed by a melting curve program to check that only single products were amplified, starting with denaturation at 95° C. for 5 s before cooling to 65° C. for 1 min then increasing at 0.1° C.s$^{-1}$ with continuous fluorescence measurement until 97° C. was reached. Negative controls consisted of water in place of cDNA and were run with all reactions. Data were analysed using LightCycler 480 software version 1.2.0.169. For each gene, a standard curve was generated using a cDNA serial dilution, and the resultant efficiencies were used to calculate expression relative to apple actin (CN938023), to minimise variation in cDNA template levels.

Expression of MpUGT88A1

Figure 5:
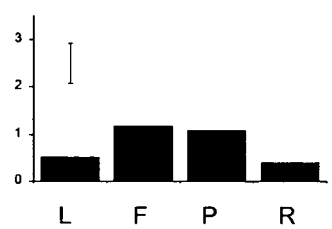
FIG. 5 shows relative expression of the MpUGT88A1 (SEQ ID NO:1) gene in different plant tissues. Quantitative RT-PCR using MpUGT88A1-specific primers was used to measure transcript levels in four apple tissues: L=expanding leaf, F=ripe fruit (150 DAFB), P=open flower and R=root tip. Expression is given relative to the root sample.

In silico expression profiling of MpUGT88A1 indicated that ESTs were represented in libraries made from all apple tissues except senescing leaf and developing fruit harvested 24-87 DAFB (FIG. 2). ESTs were most abundant in libraries constructed from flower, phloem and shoot tissue. In ripe fruit, expression was highest in core tissue, although expression was also detected in cortex and skin. As in silico expression profiling can be influenced by library sampling depth and cloning bias, MpUGT88A1 gene expression was also measured by qPCR in four apple tissues: expanding leaf, ripe fruit (150 DAFB), open flower and root tip (FIG. 5). The qPCR expression data confirmed the in silico expression profiling results. MpUGT88A1 was expressed in all four tissues, with highest expression being detected in open flower and ripe fruit. Together the expression data indicate that in apple MpUGT88A1 is a highly abundant transcript (0.1% of total transcripts), is expressed in a wide range of tissues, and the transcript is found in all tissues where phlorizin has been reported.

Example 3

Expression of the Phloretin Glycosyltransferase in *E. coli* and Characterization of Enzymic Activity Expression of MpUGT88A1 in *E. coli*

The open reading frame of EST111441 (MpUGT88A1) was amplified using primers RA335 5'-ACGGGATCCA TGGGAGACGT CATTGTACTG-3' (SEQ ID NO:20) and RA336 5'-CCCAAGCTTT TATGTAATGC TACTAACAAA GTTGAC-3'(SEQ ID NO:21). Amplified bands were purified using Qiaquick® PCR cleanup columns (Qiagen GmbH, Hilden, Germany), digested with BamHI and HindIII (underlined in the primers above), and ligated into the corresponding sites of the pET30a(+) vector (Novagen, Madison, Wis., USA). The clone was sequence verified against the original EST. Recombinant N-terminal His$_6$-tagged protein was expressed from pET-30a(+) plasmids in *E. coli* BL21-Codon-Plus™-RIL cells. Cultures were grown in a ZYM-5052 auto-inducible media (Studier 2005) at 37° C. for 4 h at 300 rpm. The temperature was then lowered to 16° C. and incubation continued for a further 60 h. Recombinant proteins were purified on 5 ml His-Trap chelating HP columns (Amersham Biosciences, Buckinghamshire, UK) and eluted using a continuous 0-250 mM imidazole gradient as described in Green et al (2007). The concentrate was then applied to a 1.6 times 40 cm G200 Superdex gel filtration column (Pharmacia Biotech, Auckland, NZ) pre-equilibrated with 50 mM Tris-HCl pH 7.5, 500 mM NaCl, 5 mM DTT at a flow rate of 1 ml·min$^{-1}$. Highest purity fractions were pooled, adjusted to 15% glycerol and stored at −80° C. A pET-30(+) vector-only control was expressed and purified as above.

Recombinant protein was analysed on 12% (w/v) SDS-Tris-Tricine gels, electroblotted onto polyvinyldifluoride membrane, and blocked as described in (Nieuwenhuizen et al. 2007). Proteins were immunolocalised with a His$_6$ monoclonal antibody (Roche, Mannheim, Germany), 1:1000, (w/v), diluted in TBS buffer containing milk powder. Membranes were incubated with an anti-rabbit alkaline phosphatase conjugated secondary antibody (Sigma-Aldrich, St. Louis, Mo., USA) and binding visualised using BCIP®NBT (nitro-blue tetrazolium) Liquid Substrate System (Sigma-Aldrich).

UGT Activity Assays

UGT activity assays were performed in triplicate in 50 μl reactions using ~1-2 μg of recombinant protein purified on His-Trap and G200 Superdex columns. Reactions were performed in glycosyltransferase assay buffer (50 mM TrisHCl, pH 7.5, 2 mM DTT) with 2 mM substrate and 1 μl [$^3$H]-UDP-glucose (uridine diphospho-D-[6-$^3$H] glucose, 13.6 Ci/mmol, GE Heathcare Buckinghamshire UK). Reactions were performed at 30° C. for 30 min and terminated by addition of 10 μL of 2 M HCl. The reaction mixtures were extracted twice with 100 µL of ethyl acetate and 20 µl of the organic phase were combined with 1 ml of non-aqueous scintillation fluid and analysed by liquid scintillation counting (Tri-Carb 2900TR, PerkinElmer, Boston, Mass., USA). Boiled enzyme and pET30a(+) vector controls were run in parallel with all enzyme reactions.

The effect on UGT activity of different pH (5-10), temperature (15-50° C.) and ionic strength of monovalent (Na$^+$, 0-100 mM; K$^+$, 0-10 mM) and divalent ions (Mg$^+$ or Mn$^{2+}$, 0-25 mM) was determined as described above using 2 µM phloretin. Reactions were shown to be linear over 1 h under standard conditions. The apparent Km value for phloretin was determined by varying the phloretin concentration from 4 µM to 0.01 µM with a fixed [$^3$H]-UDP-glucose concentration of 27 uM. The Km value for UDP-glucose was determined by varying ([$^3$H]-UDP-glucose concentration from 27 uM to 0.135 Um and by mixing ([$^3$H]-UDP-glucose (13.5 uM) with cold UDP-glucose (10-100 uM) at a fixed phloretin concentration of 2 µM.

For LC-MS analysis, reactions contained ~10 µg enzyme, 10 µM phloretin and UDP-glucose (Sigma Aldrich), UDP-galactose or UDP-xylose (CarboSource Services, University of Georgia, Ga., USA) at a final concentration of 250 µM. Reactions were performed for 16 h, and stopped by addition of 10 µl of 10% glacial acetic acid. The products of 3×100 µL reactions were combined for LC-MS analysis.

Substrate Preference of MpUGT88A1

Figure 6:
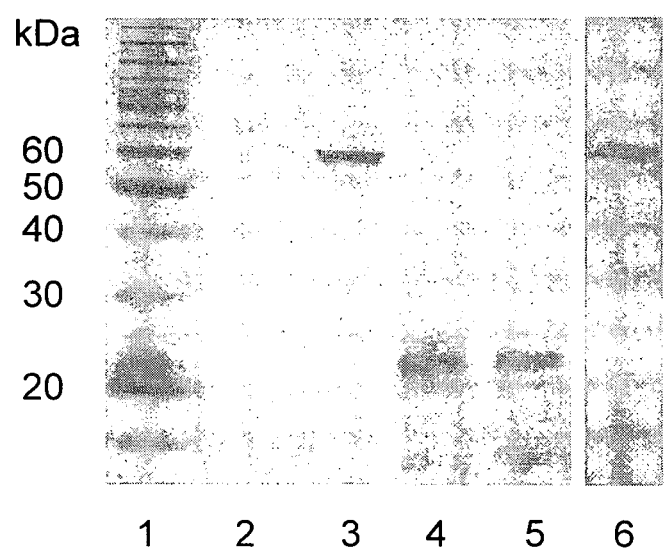
FIG. 6 shows purification of recombinant MpUGT88A1 (SEQ ID NO:1) produced in *Escherichia coli*. SDS-PAGE separation of proteins purified by $Ni^{2+}$ affinity chromatography (His-Trap) and gel filtration (G200 Superdex). 1) Benchmark ladder (Invitrogen, Auckland, NZ); 2 and 3) fractions of purified MpUGT88A1; 4 and 5) equivalent fractions of purified pET30a(+) vector control; 6, immunodetection of MpUGT88A1 using a $His_6$ monoclonal antibody.

The entire coding region of the MpUGT88A1 cDNA was cloned in frame into the expression vector pET30a(+) for the production of His$_6$-tagged recombinant protein in *Escherichia coli*. The recombinant protein was isolated by Ni$^{2+}$ affinity and gel filtration chromatography. Successful expression of the fusion protein was indicated in SDS-PAGE by the appearance of a protein of the expected 58 kDa size (53.5 kDa for MpUGT88A1+4.5 kDa for the His$_6$ tag and associated residues) in MpUGT88A1 extracts but not in equivalent vector control extracts (FIG. 6, Lanes 2-5). Western analysis using His$_6$ monoclonal antibodies confirmed the 58 kDa was a His-labelled recombinant protein (FIG. 6, Lane 6).

For functional characterisation of MpUGT88A1 aliquots of the purified recombinant protein were assayed for glycosyltransferase activity using [$^3$H]-UDP-glucose as the sugar donor. Fifteen substrates (caffeic acid, catechin, chlorogenic acid, 2-coumaric acid, 3-coumaric acid, 4-coumaric acid, cyanidin, 3-(3,4 dihydroxyphenyl) propionic acid, epicatechin, 3-hydroxybenzoic acid, naringenin, phloretin, protocatechuic acid, quercetin and rutin) that are natural constituents of apple fruit or commonly available phenolic compounds were screened for activity. Of these substrates, only phloretin was utilised by MpUGT88A1 as an acceptor. The vector control showed no activity towards phloretin, indicating the glycosylation reaction was specific to the MpUGT88A1 enzyme.

Kinetic parameters were determined for MpUGT88A1 with respect to phloretin and UDP-glucose. The enzyme showed a $K_m$ of 0.62 uM±0.1 µM for phloretin with a turnover rate of 9.72×10$^{-4}$ mol/sec/mol. The observed $K_m$ for UDP-glucose was ~13 uM which is consistent with that observed for other UGT enzymes.

Figure 8:
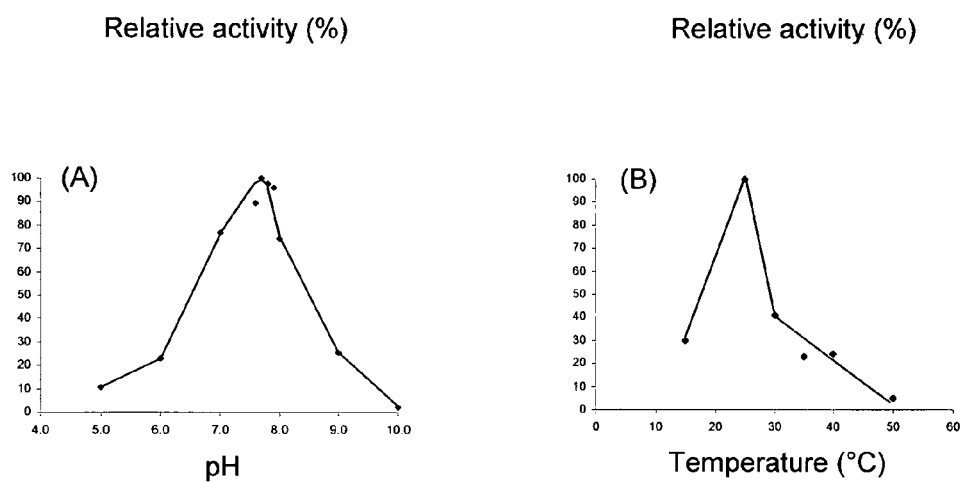
FIG. 8 shows (A) the activity of MdPGT1 towards phloretin (2 µM), assayed in reaction mixtures containing 50 mM Tris-HCl at the pH indicated; and (B) the activity of MdPGT1 towards phloretin (2 µM), assayed under standard conditions at the indicated temperatures.

MpUGT88A1 protein was tested over a pH range of 5-10. The enzyme showed significant activity from pH 7-8 with maximum activity at pH 7.7 (FIG. 8A). Activity decreased to 20% at pH 6 and 9 and less than 5% at pH 5 and 10. The enzyme showed a broad temperature range from 15-50° C. with maximum activity at 25° C. (FIG. 8B). Enzyme activity was not inhibited by the addition of divalent cations (Mg$^{2+}$ or Mn$^{2+}$, 25 mM) or monovalent cations (Na$^+$, 100 mM or K$^+$, 10 mM).

LC-MS Analysis of in vitro Reaction Mixtures

LC-MS employed an LTQ linear ion trap mass spectrometer fitted with an ESI interface (ThermoQuest, Finnigan, San Jose, Calif., USA) coupled to an Ettan™ MDLC (GE Healthcare Bio-Sciences, Uppsala, Sweden).

Phenolic compound separation was achieved using a Prodigy 5 µm ODS(3) 100 Å (Phenomenex, Torrance, Calif., USA), 150×2 mm analytical column maintained at 35° C. A 0.2 µm in-line filter (Alltech, Deerfield, Ill., USA) was installed before the column. Solvents were (A) acetonitrile+ 0.1% formic acid and (B) water+0.1% formic acid and the flow rate was 200 µL·min$^{-1}$. The initial mobile phase, 5% A/95% B, was held for 5 min then ramped linearly to 10% A at 10 min, 17% A at 25 min, 23% A at 30 min, 30% A at 40 min, 97% A between 48-53 min before resetting to the original conditions. Sample injection volume was 50 µL.

MS data was acquired in the negative mode using a data-dependent LC-MS$^3$ method. This method isolates and fragments the most intense parent ion to give MS$^2$ data, then isolates and fragments the most intense daughter ion (MS$^3$ data). To maximise sensitivity, the full scan range was set to m/z 420-490 from 0-42.9 min for the detection of phloretin glycosides and then to m/z 270-280 from 43 min for the detection of unreacted phloretin. The ESI voltage, capillary temperature, sheath gas pressure and sweep gas were set at −10 V, 275° C., 40 psi, and 5 psi, respectively.

LC-MS Analysis

Figure 7:
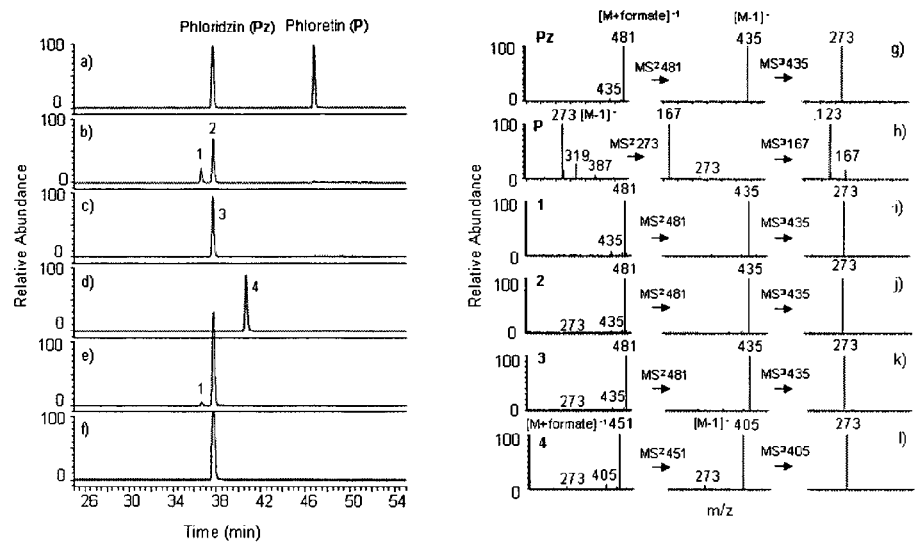
FIG. 7 shows LC-MS analysis of the products of the reaction between MpUGT88A1 (SEQ ID NO:1), phloretin and UDP-sugars. HPLC chromatograms: a) mixed standard of phlorizin and phloretin; b) phloretin+UDP-galactose; c) phloretin+UDP-glucose; d) phloretin+UDP-xylose; e) phloretin+UDP-galactose spiked with phlorizin; f) phloretin+ UDP-glucose spiked with phlorizin; MS spectra: g) fullscan, $MS^2$ and $MS^3$ data for phlorizin; h) fullscan, $MS^2$ and $MS^3$ data for phloretin; i) fullscan, $MS^2$ and $MS^3$ data for peak 1; j) fullscan, $MS^2$ and $MS^3$ data for peak 2; k) fullscan, $MS^2$ and $MS^3$ data for peak 3; and 1) fullscan, $MS^2$ and $MS^3$ data for peak 4.

Products of the reaction between MpUGT88A1, phloretin and UDP-glucose were analysed by HPLC (FIG. 7c) and compared to chromatograms of phloretin and phlorizin standards (FIG. 7a). The product of the MpUGT88A1 enzyme reaction ran at 38 min—the same retention time as the phlorizin standard. No phloretin was observed at 47 min, indicating the reaction had run to completion (FIG. 7c). An HPLC run where the phlorizin standard was spiked into the MpUGT88A1 reaction mixture further confirmed that that the products of the reaction had identical retention times (FIG. 7f).

The MpUGT88A1 enzyme was tested with phloretin in the presence of two additional activated sugar donors—UDP-xylose and UDP-galactose. HPLC chromatograms indicated that a single glycosylated product was formed with UDP-xylose with a retention time of 40.5 min (FIG. 7d). Two peaks were observed in the presence of UDP-galactose—a small peak at 36.5 min and a larger peak at 38 min (FIG. 7b). The larger peak co-eluted with the phlorizin standard at 38 min when the products of the UDP-galactose reaction were spiked with authentic phlorizin (FIG. 7e).

Mass spectrometry was used to further characterise the products of the MpUGT88A1 reactions. Phloretin (FIG. 7h) was detected as its pseudo-molecular ion m/z 273 [M-1]$^-$, while phlorizin (FIG. 7g) and the phloretin glycoside reaction products were detected predominately as the corresponding formate adducts, m/z 481 [M+formate]$^{-1}$ for the glucoside (Peak 3; FIG. 7c) and the galactosides (Peaks 1 and 2; FIG. 7b) and m/z 451 [M+formate]$^{-1}$ for the xyloside (Peak 4; FIG. 7d). MS$^2$ on the formate adducts, identified the expected pseudo-molecular ion at m/z 435 [M-1]$^-$ for the glucoside (FIG. 7k) and galactosides (FIGS. 7i and 7j) and m/z 405 [M-1]$^-$ for the xyloside (FIG. 7l). MS$^3$ on the m/z 435 [M-1]$^-$ glucoside and galactoside ions and the m/z 405 [M-1]$^-$ xyloside ion, all identified the m/z 273 [M-1]$^-$ of the phloretin aglycone.

Expression of Md_138221 in *E. coli*

The Md_138221 sequence (SEQ ID NO: 14) was also amplified and cloned into pET30a(+) by standard techniques as described above for MpUGT88A1.

The cloned sequence was confirmed by sequencing before transfer into RIL cells as described above. Assays for phloretin glycosyl transferase activity were then completed as described above. Md_138221 also showed phloretin glycosyltransferase activity at approximately 3% of that shown for MpUGT88A1.

Discussion

A genomics approach was used to identify the gene MpUGT88A1 in apple (cv. Royal Gala) with homology to Family 88 UGTs of unknown function from *Arabidopsis*, rice and sweetleaf (*S. rebaudiana*). Glycosyltransferase assays and LC-MS revealed that the recombinant MpUGT88A1 enzyme could specifically glycosylate phloretin in the presence of UDP-glucose, UDP-xylose and UDP-galactose. This is the first report of functional characterisation of a UGT that utilises a dihydrochalcone as its primary substrate.

The glycosylated product of phloretin and UDP-glucose co-migrated with a known phlorizin standard, indicating that MpUGT88A1 is likely to be the enzyme that glycosylates phloretin to phlorizin in planta. This assertion is supported by other lines of evidence. Expression data indicated that the MpUGT88A1 gene was highly expressed in leaf, root, flower and fruit, which is consistent with the presence of phlorizin in these apple tissues. The recombinant MpUGT88A1 protein also produced glycosides with UDP-xylose and UDP-galactose (with one of the products glycosylated with UDP-galactose having the same retention time as phlorizin). Apples have been reported to produce two phloretin glycosides in addition to phloretin 2'-glucoside (phlorizin), namely phloretin 2'-galactoside (Barth et al. 2005) and phloretin 2'-xyloglucoside (Lommen et al. 2000). Although the exact nature of the glycosylation in these reactions has not been determined (as no authentic apple compounds were available for comparison), the MS spectra clearly indicated that the sugar molecules were attached to phloretin. It seems likely the regio-specificity of MpUGT88A1 is to the 2'-hydroxyl position, as substrates (e.g. naringenin and quercetin) with hydroxyl groups in alternative positions were not utilised as substrates.

No sequences within UGT Family 88 have been ascribed a definitive function to date. SvUGT88B1 from *S. rebaudiana* is reported to show trace activity with kaempferol (Richman et al. 2005), whilst VmUFGT4, a partial clone isolated from *V. mungo* seedling tissue (Mato et al. 1998) and OsBAC10743 from rice, are completely uncharacterised. Although UGT sequences from *Arabidopsis* have been extensively characterised in vitro (e.g. Lim et al. 2002), no function has been ascribed to AtUGT88A1. AtUGT88A1 is moderately expressed in a number of *Arabidopsis* tissues but especially in cauline leaves (*Arabidopsis* eFP browser; http://www.bar.utoronto.ca).

Family 88 UGTs are classified as belonging to the larger Group E UGTs, which also contains UGT Families 71 and 72. Some enzymes in these families have been functionally characterised and show activity towards a wide range of substrates including: phenylpropanoids, benzoates chlorinated phenols and anilines (AtUGT71C1, Lim and Bowles 2004; AtUGT72E2, Lim and Bowles 2004; AtUGT72B, Loutre et al. 2003); coumarins, flavonoids and naphthols (NtGT1a, NtGT3, *Nicotiana tabacum*, Taguchi et al. 2003); quercetin, isoflavones and triterpene saponins (UGT71G1, *Medicago truncatula*, Achnine et al. 2005) and hydroxyquinone (arbutin synthase, *Rauvolfia serpentina*, Hefner and Stockigt 2003). It is possible that some of these enzymes also accept dihydrochalcones as substrates, but this has not been reported. Other Family 88 UGTs may be specific for dihydrochalcones, but this is unlikely given that dihydrochalcone glycosides are found almost exclusively in *Malus* (and have been used as markers for the detection of apple admixtures in other fruit juices and purees, Dragovic-Uzelac et al. 2005). Family 88 UGTs are most likely to show as yet undetermined stereospecificity represented by the 2' hydroxyl position in phloretin.

In conclusion, our results have identified a key enzyme in the biochemical pathway to phlorizin production in apples. The ability to manipulate phlorizin levels in fruit is an important target in apple breeding programmes as "the use of phlorizin may provide the molecular basis for the clinical observation that an apple a day keeps the doctor away" (Ehrenkranz et al. 2005).

Example 4

Increasing Phloretin Glycosyltransferase Activity in Plants by Expression of a Phloretin Glycosyltransferase Polynucleotide of the Invention in Plants Transient Transformation of Tobacco Leaves.

Tobacco (*Nicotiana benthamiana*) is transiently transformed with *Agrobacterium* cultures containing a gene/polynucleotide (e.g. SEQ ID NO:6-15) encoding phloretin glycosyltransferase (e.g. SEQ ID NO: 1-5) cloned in pGreen (Hellens et al., 2000) mixed with *Agrobacterium* containing the gene for the silencing suppressor P19 as previously described (Hellens et al., 2005). Controls are run using *Agrobacterium* containing P19 in pGreen alone. Tobacco leaves were harvested 9 days after transformation and frozen in liquid nitrogen.

Stable Transformation of Apple Plants

Two constructs containing MdPGT1 (EST111441) were produced, in pHEX2 (Hellens et al., 2005) by standard techniques, to characterise the role of the MdPGT1 gene in transgenic apple plants.

An RNAi knockout construct was produced. This construct contained 455 nucleotides of the EST111441 gene (nucleotides 473-928 of SEQ ID NO: 6) in sense orientation and the same 455 nucleotides oriented in the antisense direction to form an inverted repeat. Constitutive expression of the hairpin dsRNA was driven by a cauliflower mosaic virus (CaMV) 35S promoter.

An over-expression construct was produced. This construct contained the full length EST111441 (SEQ ID NO: 6) driven by a CaMV 35S promoter.

Transgenic apple plants were regenerated as described in Yao et al., (1995) Plant cell Reports 14: 407-412.

Fourteen apple lines containing the EST111441 knockout construct were regenerated on kanamycin-containing medium. Eleven of the lines were confirmed by PCR to contain the EST111441 knockout construct. Five lines that showed the most significant decrease in expression of EST111441 RNA (compared to EST111441 expression in wild type leaves) were transferred to the containment greenhouse for further analysis (including analysis of phloretin and phlorizin levels).

Eight apple lines containing the EST111441 over-expression construct were regenerated on kanamycin-containing medium. These lines will be characterised in the same way as the knockout lines to choose the best plants for transfer into the containment greenhouse.

Phlorizin Measurement

Collected leaves are immediately flash-frozen in liquid $N_2$, in the field, stored at −40° C., lyophilized and ground to a fine powder. Extracts are prepared by pre-washing 200 mg of powder in diethylether and extracting at 40° C. for 3 hr in 70% acetone-8.6 mM ascorbic acid. Acetone is removed by evaporation under pressure and distilled $H_2O$ added to a constant 5 ml vol. Concentrations of phloridzin and phloretin are estimated by reverse phase HPLC against commercial standards, with a 45:55 MeOH:$H_2O$ solvent, buffered with PIC-A reagent (Supelco, column 25 cm×4.6 mm containing a 5 pm $C_{18}$ bonded phase, preceded by a 2 cm guard column packed with 37-75 um Porasil B, flow rate 0.9 ml $min^{-1}$) and detected at 254 nm with a UV detector. Hunter and Hull 1993

These experiments can show that over-expression of the phloretin glycosyltransferase sequence of the invention can increase phloretin glycosyltransferase activity or phlorizin production in plants.

Example 5

Identification of Variant Phloretin Glycosyltransferase Sequences

The Md_111441 sequence was used to identify orthologous phloretin glycosyltransferase genes from HortResearch proprietary sequence data bases.

Four variant sequences were identified as summarised in Table 1 below.

TABLE 1

| Phloretin glycosyltransferase reference | Malus species | Polynucleotide SEQ ID NO: cDNA | Polynucleotide SEQ ID NO: Open reading frame (ORF) | Polypeptide SEQ ID NO: |
|---|---|---|---|---|
| Md_111441 | x domestica | 6 | 7 | 1 |
| Ms_297292 | sieboldii | 8 | 9 | 2 |
| Md_88077 | x domestica | 10 | 11 | 3 |
| Md_87623 | x domestica | 12 | 13 | 4 |
| Md_138221 | x domestica | 14 | 15 | 5 |

An ClustalX (Version 1.8) alignment (Hall, 1999) of the polypeptide sequences of Md_111441 and all of the four variants is shown in FIG. 9. Also illustrated is completely conserved region (SEQ ID NO: 16) present in Md_111441 and all other variants. The function of these variants as phloretin glycosyltransferases can be confirmed using the methods described in the examples above.

REFERENCES

Achnine, L., Huhman, D. V., Farag, M. A., Sumner, L. W., Blount, J. W. and Dixon, R. A. (2005). Genomics-based selection and functional characterization of triterpene glycosyltransferases from the model legume *Medicago truncatula*. Plant Journal 41: 875-887.

Awad, M. A., de Jager, A. and van Westing, L. M. (2000). Flavonoid and chlorogenic acid levels in apple fruit: characterisation of variation. Scientia Horticulturae 83: 249-263.

Barth, S. W., Fahndrich, C., Bub, A., Dietrich, H., Watzl, B., Will, F., Briviba, K. and Rechkemmer, G. (2005). Cloudy apple juice decreases DNA damage, hyperproliferation and aberrant crypt foci development in the distal colon of DMH-initiated rats. Carcinogenesis 26: 1414-1421.

Boccia, M. M., Kopf, S. R. and Baratti, C. M. (1999). Phlorizin, a competitive inhibitor of glucose transport, facilitates memory storage in mice. Neurobiology of Learning and Memory 71: 104-112.

Cox, S. D., Jayasinghe, K. C. and Markham, J. L. (2005). Antioxidant activity in Australian native sarsaparilla (*Smilax glyciphylla*). Journal of Ethnopharmacology 101: 162-168.

Dong, H., Ning, Z., Yu, L., Li, L., Lin, L. and Huang, J. (2007). Preparative separation and identification of the flavonoid phlorhizin from the crude extract of *Lithocarpus polystachyus* Rehd. Molecules 12: 552-62.

Dragovic-Uzelac, V., Pospisil, J., Levaj, B. and Delonga, K. (2005). The study of phenolic profiles of raw apricots and apples and their purees by HPLC for the evaluation of apricot nectars and jams authenticity. Food Chemistry 91: 373-383.

Ehrenkranz, J. R., Lewis, N. G., Kahn, C. R. and Roth, J. (2005). Phlorizin: a review. Diabetes/Metabolism Research and Reviews 21: 31-38.

Fukuchi-Mizutani, M., Okuhara, H., Fukui, Y., Nakao, M., Katsumoto, Y., Yonekura-Sakakibara, K., Kusumi, T., Hase, T. and Tanaka, Y. (2003). Biochemical and molecular characterization of a novel UDP-glucose:anthocyanin 3'-O-glucosyltransferase, a key enzyme for blue anthocyanin biosynthesis, from gentian. Plant Physiology 132: 1652-1663.

Gessler, C., Patocchi, A., Sansavini, S., Tartarini, S. and Gianfranceschi, L. (2006). *Venturia inaequalis* resistance in apple. Critical Reviews in Plant Sciences 25: 473-503.

Green, S., Friel, E. N., Matich, A., Beuning, L. L., Cooney, J. M., Rowan, D. D. and MacRae, E. (2007). Unusual features of a recombinant apple alpha-farnesene synthase. Phytochemistry 68: 176-188.

Hall, T. A. 1999. BioEdit: a user-friendly biological sequence alignment editor and analysis program for Windows 95/98/NT. Nucl. Acids. Symp. Ser. 41:95-98.

Hansen, K. S., Kristensen, C., Tattersall, D. B., Jones, P. R., Olsen, C. E., Bak, S. and Moller, B. L. (2003). The in vitro substrate regiospecificity of recombinant UGT85B1, the cyanohydrin glucosyltransferase from *Sorghum bicolor*. Phytochemistry 64: 143-151.

Hefner, T. and Stockigt, J. (2003). Probing suggested catalytic domains of glycosyltransferases by site-directed mutagenesis. European Journal of Biochemistry 270: 533-538.

Hellens, R. P., Allan, A. C., Friel, E. N., Bolitho, K., Grafton, K., Templeton, M. D., Karunairetnam, S. and Laing, W. A. (2005) Transient plant expression vectors for functional genomics, quantification of promoter activity and RNA silencing. *Plant Methods*, 1:13

Hilt, P., Schieber, A., Yildirim, C., Arnold, G., Klaiber, I., Conrad, J., Beifuss, U. and Carle, R. (2003). Detection of phloridzin in strawberries (*Fragaria×ananassa* Duch.) by HPLC-PDA-MS/MS and NMR spectroscopy. Journal of Agricultural and Food Chemistry 51: 2896-2899.

Hunter, M. D. and Hull, L. A. (1993). Variation in concentrations of phlorhizin and phloretin in apple foliage. Phytochemistry 34: 1251-1254.

Jackson, R. G., Lim, E. K., Li, Y., Kowalczyk, M., Sandberg, G., Hoggett, J., Ashford, D. A. and Bowles, D. J. (2001). Identification and biochemical characterization of an *Arabidopsis* indole-3-acetic acid glucosyltransferase. Journal of Biological Chemistry 276: 4350-4356.

Jones, P., Messner, B., Nakajima, J., Schaffner, A. R. and Saito, K. (2003). UGT73C6 and UGT78D1, glycosyltransferases involved in flavonol glycoside biosynthesis in *Arabidopsis thaliana*. Journal of Biological Chemistry 278: 43910-43918.

Li, Y., Baldauf, S., Lim, E. K. and Bowles, D. J. (2001). Phylogenetic analysis of the UDP-glycosyltransferase multigene family of *Arabidopsis thaliana*. Journal of Biological Chemistry 276: 4338-4343.

Lim, E. K., Ashford, D. A., Hou, B., Jackson, R. G. and Bowles, D. J. (2004). *Arabidopsis* glycosyltransferases as biocatalysts in fermentation for regioselective synthesis of diverse quercetin glucosides. Biotechnology and Bioengineering 87: 623-631.

Lim, E. K. and Bowles, D. J. (2004). A class of plant glycosyltransferases involved in cellular homeostasis. EMBO Journal 23: 2915-2922.

Lim, E. K., Doucet, C. J., Li, Y., Elias, L., Worrall, D., Spencer, S. P., Ross, J. and Bowles, D. J. (2002). The activity of *Arabidopsis* glycosyltransferases toward salicylic acid, 4-hydroxybenzoic acid, and other benzoates. Journal of Biological Chemistry 277: 586-592.

Lim, E. K., Higgins, G. S., Li, Y. and Bowles, D. J. (2003). Regioselectivity of glucosylation of caffeic acid by a UDP-glucose:glucosyltransferase is maintained in planta. Biochemical Journal 373: 987-992.

Lim, E. K., Jackson, R. G. and Bowles, D. J. (2005). Identification and characterisation of *Arabidopsis* glycosyltransferases capable of glucosylating coniferyl aldehyde and sinapyl aldehyde. FEBS Letters 579: 2802-2806.

Lommen, A., Godejohann, M., Venema, D. P., Hollman, P. C. and Spraul, M. (2000). Application of directly coupled HPLC-NMR-MS to the identification and confirmation of quercetin glycosides and phloretin glycosides in apple peel. Analytical Chemistry 72: 1793-1797.

Loutre, C., Dixon, D. P., Brazier, M., Slater, M., Cole, D. J. and Edwards, R. (2003). Isolation of a glucosyltransferase from *Arabidopsis thaliana* active in the metabolism of the persistent pollutant 3,4-dichloroaniline. Plant Journal 34: 485-493.

MacDonald, R. E. and Bishop, C. J. (1952). Phloretin: An antibacterial substance obtained from apple leaves. Canadian Journal of Botany 30: 486-89.

Mato, M., Ozeki, Y., Itoh, Y., Higeta, D., Yoshitama, K., Teramoto, S., Aida, R., Ishikura, N. and Shibata, M. (1998). Isolation and characterization of a cDNA clone of UDP-galactose: flavonoid 3-O-galactosyltransferase (UF3GaT) expressed in *Vigna mungo* seedlings. Plant and Cell Physiology 39: 1145-1155.

Messner, B., Thulke, O. and Schaffner, A. R. (2003). *Arabidopsis* glucosyltransferases with activities toward both endogenous and xenobiotic substrates. Planta 217: 138-146.

Newcomb, R. D., Crowhurst, R. N., Gleave, A. P., Rikkerink, E. H. A., Allan, A. C., Beuning, L. L., Bowen, J. H., Gera, E., Jamieson, K. R., Janssen, B. J., Laing, W. A., McArtney, S., Nain, B., Ross, G. S., Snowden, K. C., Souleyre, E. J. F., Walton, E. F. and Yauk, Y.-K. (2006). Analyses of expressed sequence tags from apple. Plant Physiology 141: 147-166.

Nieuwenhuizen, N. J., Beuning, L. L., Sutherland, P. W., Sharma, N. N., Cooney, J. M., Bieleski, L. R. F., Schröder, R., MacRae, E. A. and Atkinson, R. G. (2007). Identification and characterisation of acidic and novel basic forms of actinidin, the highly abundant cysteine protease from kiwifruit. Functional Plant Biology 34: 946-961.

Petersen, C. (1835). Analyse des phloridzins. Annales Academie Science Francaise 15: 178.

Puel, C., Quintin, A., Mathey, J., Obled, C., Davicco, M. J., Lebecque, P., Kati-Coulibaly, S., Horcajada, M. N. and Coxam, V. (2005). Prevention of bone loss by phloridzin, an apple polyphenol, in ovariectomized rats under inflammation conditions. Calcified Tissue International 77: 311-318.

Rezk, B. M., Haenen, G. R., van der Vijgh, W. J. and Bast, A. (2002). The antioxidant activity of phloretin: the disclosure of a new antioxidant pharmacophore in flavonoids. Biochemical and Biophysical Research Communications 295: 9-13.

Richman, A., Swanson, A., Humphrey, T., Chapman, R., McGarvey, B., Pocs, R. and Brandle, J. (2005). Functional genomics uncovers three glucosyltransferases involved in the synthesis of the major sweet glucosides of *Stevia rebaudiana*. Plant Journal 41: 56-67.

Ridgway, T., O'Reilly, J., West, G., Tucker, G. and Wiseman, H. (1996). Potent antioxidant properties of novel apple-derived flavonoids with commercial potential as food additives. Biochemical Society Transactions 24: 391S.

Ridgway, T., O'Reilly, J., West, G., Tucker, G. and Wiseman, H. (1997). Antioxidant action of novel derivatives of the apple-derived flavonoid phloridzin compared to oestrogen: relevance to potential cardioprotective action. Biochemical Society Transactions 25: 106S.

Ridgway, T. and Tucker, G. (1997). Phloridzin derivatives; food additives/chemopreventative drugs of the future. Biochemical Society Transactions 25: 109S.

Ross, J., Li, Y., Lim, E. and Bowles, D. J. (2001). Higher plant glycosyltransferases. Genome Biology 2: 3004.1-3004.6.

Schaffer, R. J., Friel, E. N., Souleyre, E. J., Bolitho, K., Thodey, K., Ledger, S., Bowen, J. H., Ma, J. H., Nain, B., Cohen, D., Gleave, A. P., Crowhurst, R. N., Janssen, B. J., Yao, J. L. and Newcomb, R. D. (2007). A genomics approach reveals that aroma production in apple is controlled by ethylene predominantly at the final step in each biosynthetic pathway. Plant Physiology 144: 1899-912.

Studier, F. W. (2005). Protein production by auto-induction in high-density shaking cultures. Protein Expression and Purification 41: 207-234.

Taguchi, G., Nakamura, M., Hayashida, N. and Okazaki, M. (2003). Exogenously added naphthols induce three glucosyltransferases, and are accumulated as glucosides in tobacco cells. Plant Science 164: 231-240.

Veeriah, S., Kautenburger, T., Habermann, N., Sauer, J., Dietrich, H., Will, F. and Pool-Zobel, B. L. (2006). Apple flavonoids inhibit growth of HT29 human colon cancer cells and modulate expression of genes involved in the biotransformation of xenobiotics. Molecular Carcinogenesis 45: 164-174.

Vogt, T. (2000). Glycosyltransferases involved in plant secondary metabolism. Evolution of Metabolic Pathways. J. T. Romeo, R. Ibrahim, L. Varin and V. De Luca. Oxford, Elsevier Science Ltd.: 317-347.

Watts, K. T., Lee, P. C. and Schmidt-Dannert, C. (2004). Exploring recombinant flavonoid biosynthesis in metabolically engineered *Escherichia coli*. Chembiochem 5: 500-507.

Whiting, G. C. and Coggins, R. A. (1975). Estimation of the monomeric phenolics from ciders. Journal of the Science of Food and Agriculture 26: 1833-1838.

Zhang, X. Z., Zhao, Y. B., Li, C. M., Chen, D. M., Wang, G. P., Chang, R. F. and Shu, H. R. (2007). Potential polyphenol markers of phase change in apple (*Malus domestica*). Journal of Plant Physiology 164: 574-580.

The invention claimed is:

1. A method for producing a plant cell or plant with at least one of a) increased phlorizin content, and b) increased phloretin glycosyltransferase activity, the method comprising transformation of a plant cell or plant with a polynucleotide encoding a polypeptide with at least 95% sequence identity to the amino acid sequence of any one of SEQ ID NOs: 1 to 5, wherein in order to increase phlorizin content as in a) the plant cell or plant contains phloretin.

2. The method of claim 1, wherein the polynucleotide encodes a polypeptide with phloretin glycosyltransferase activity.

3. The method of claim 1, wherein the polynucleotide encodes a polypeptide with the amino acid sequence of SEQ ID NO: 1.

4. The method of claim 1, wherein the polynucleotide comprises a nucleotide sequence selected from the group consisting of the sequences SEQ ID NOs: 6, 7, 8, 9, 10, 11, 12, 13, 14 and 15, and sequences with at least 95% identity to the nucleotide sequences selected from the group consisting of SEQ ID NOs: 6, 7, 8, 9, 10, 11, 12, 13, 14 and 15.

5. The method of claim 1, wherein the polynucleotide comprises a nucleotide sequence with at least 95% identity to the sequence of SEQ ID NO: 6.

6. The method of claim 1, wherein the polynucleotide comprises the nucleotide sequence of SEQ ID NO: 6.

7. The method of claim 1, wherein the polynucleotide comprises a nucleotide sequence with at least 95% identity to the sequence of SEQ ID NO: 7.

8. The method of claim 1, wherein the polynucleotide comprises the nucleotide sequence of SEQ ID NO: 7.

9. The method of claim 1 wherein the polynucleotide encodes a polypeptide with the amino acid sequence of any one of SEQ ID NOs: 1 to 5.

10. The method of claim 1, wherein the polynucleotide comprises a nucleotide sequence selected from the group consisting of the sequences of SEQ ID NOs: 6, 7, 8, 9, 10, 11, 12, 13, 14 and 15.

11. A plant cell or plant produced by the method of claim 1.

12. A method of producing phlorizin, the method comprising extracting phlorizin from the plant cell or plant of claim 11.

13. A host cell, plant cell or plant wherein the host cell, plant cell or plant comprises a transgene including a polynucleotide encoding polypeptide comprising the sequence of any one of SEQ ID NOs: 1-5, or a polypeptide with at least 95% identity to the sequence of any one of SEQ ID NOs: 1-5, wherein percent identity is calculated over the entire length of SEQ ID NOs: 1-5.

14. The host cell, plant cell or plant of claim 13, wherein the polynucleotide encodes a polypeptide with phloretin glycosyltransferase activity.

15. The host cell, plant cell or plant of claim 13, wherein the polynucleotide encodes a polypeptide comprising a sequence with at least 95% identity to SEQ ID NO: 5.

16. The host cell, plant cell or plant of claim 13, wherein the polynucleotide encodes a polypeptide comprising the sequence of SEQ ID NO: 5.

17. The hose cell, plant cell or plant of claim 13 comprising the sequence of any one of SEQ ID NOs: 6 to 15, or a sequence with at least 95% identity to the sequence of any one of SEQ ID NOs: 6 to 15, wherein percent identity is calculated over the entire length of SEQ ID NOs: 6 to 15.

18. The host cell, plant cell or plant of claim 17 comprising the sequence of any one of SEQ ID NOs: 6 to 15.

19. The host cell, plant cell or plant of claim 17 comprising the sequence of any one of SEQ ID NOs: 8 to 15, or a sequence with at least 95% identity to the sequence of any one of SEQ ID NOs: 8 to 15, wherein percent identity is calculated over the entire length of SEQ ID NOs: 8 to 15.

20. The host cell, plant cell or plant of claim 19 comprising the sequence of any one of SEQ ID NOs: 8 to 15.

21. The host cell, plant cell or plant of claim 13, wherein the polynucleotide comprises a sequence with at least 95% sequence identity to the sequence of SEQ ID NO: 14.

22. The host cell, plant cell or plant of claim 13, wherein the polynucleotide comprises the sequence of SEQ ID NO: 14.

23. The host cell, plant cell or plant of claim 13, wherein the polynucleotide comprises a sequence with at least 95% sequence identity to the sequence of SEQ ID NO: 15, wherein percent identity is calculated over the entire length of SEQ ID NO: 15.

24. The host cell, plant cell or plant of claim 13, wherein the polynucleotide comprises the sequence of SEQ ID NO: 15.

25. The host cell, plant cell or plant of claim 13 which comprises a transgene including a polynucleotide encoding a polypeptide comprising the sequence of any one of SEQ ID NOs: 1-5.

26. The host cell, plant cell or plant of claim 13 which comprises a transgene including a polynucleotide encoding a polypeptide comprising the sequence of any one of SEQ ID NOs: 2 to 5, or a polypeptide with at least 95% identity to the sequence of any one of SEQ ID NOs: 2 to 5, wherein percent identity is calculated over the entire length of SEQ ID NOs: 2 to 5.

27. The host cell, plant cell or plant of claim 13 which comprises a transgene including a polynucleotide encoding a polypeptide comprising the sequence of any one of SEQ ID NOs: 2-5.

28. A genetic construct that comprises a polynucleotide encoding a polypeptide comprising the sequence of any one of SEQ ID NOs: 1 to 5, or a polypeptide with at least 95% identity to the sequence of any one of SEQ ID NOs: 1 to 5, wherein percent identity is calculated over the entire length of SEQ ID NOs: 1 to 5; and wherein the polynucleotide is operably linked to a promoter that is at least one of:

a) not normally associated with the polynucleotide in nature,
b) derived from the gene of a plant other than that from which the polynucleotide is derived,
c) derived from a virus,
d) derived from a plant pathogenic bacterium, or
e) derived from a fungus.

29. A host cell comprising the genetic construct of claim 28.

30. A method for the biosynthesis of phlorizin comprising the steps of culturing a plant host-cell comprising the genetic construct of claim 28, capable of expressing a phloretin glycosyltransferase, in the presence of a phloretin which may be supplied to, or may be naturally present within the plant host cell.

31. A plant cell which comprises the genetic construct of claim 28.

32. A plant which comprises the plant cell of claim 31.

* * * * *